(12) United States Patent
Rodi

(10) Patent No.: US 10,619,163 B2
(45) Date of Patent: Apr. 14, 2020

(54) TAGGING AND ASSESSING A TARGET SEQUENCE

(71) Applicant: RHODX, Inc., Del Mar, CA (US)

(72) Inventor: Charles Rodi, Del Mar, CA (US)

(73) Assignee: RHODX, Inc., Del Mar, CA (US)

( * ) Notice: Subject to any disclaimer, the term of this patent is extended or adjusted under 35 U.S.C. 154(b) by 202 days.

(21) Appl. No.: 15/320,204

(22) PCT Filed: Jul. 2, 2015

(86) PCT No.: PCT/US2015/039080
§ 371 (c)(1),
(2) Date: Dec. 19, 2016

(87) PCT Pub. No.: WO2016/004368
PCT Pub. Date: Jan. 7, 2016

(65) Prior Publication Data
US 2017/0121716 A1    May 4, 2017

Related U.S. Application Data

(60) Provisional application No. 62/020,823, filed on Jul. 3, 2014, provisional application No. 62/151,320, filed on Apr. 22, 2015.

(51) Int. Cl.
*C12Q 1/68* (2018.01)
*C07H 21/00* (2006.01)
*C12N 15/66* (2006.01)
*C12N 15/10* (2006.01)
*C12Q 1/6816* (2018.01)

(52) U.S. Cl.
CPC .......... *C12N 15/66* (2013.01); *C12N 15/10* (2013.01); *C12N 15/1096* (2013.01); *C12Q 1/6816* (2013.01)

(58) Field of Classification Search
CPC ................................. C12Q 1/68; C07H 21/00
See application file for complete search history.

(56) References Cited

U.S. PATENT DOCUMENTS

| | | | | | |
|---|---|---|---|---|---|
| 5,162,209 | A | * | 11/1992 | Scheele | C12N 15/1096 435/320.1 |
| 5,215,899 | A | * | 6/1993 | Dattagupta | C12O 1/682 435/320.1 |
| 6,114,149 | A | * | 9/2000 | Fry | C12N 15/1096 435/6.16 |
| 2001/0019716 | A1 | * | 9/2001 | Riley | C07K 14/35 424/190.1 |
| 2001/0051340 | A1 | * | 12/2001 | Singh | C07H 19/06 435/6.16 |
| 2002/0055109 | A1 | * | 5/2002 | Thill | C12Q 1/6809 435/6.15 |
| 2003/0082536 | A1 | * | 5/2003 | Delagrave | C07H 21/00 435/6.12 |
| 2004/0185477 | A1 | * | 9/2004 | Slepnev | C12Q 1/6809 435/5 |
| 2006/0216816 | A1 | * | 9/2006 | Ohnishi | B01L 3/502715 435/287.2 |
| 2007/0111216 | A1 | * | 5/2007 | Jendrisak | C12Q 1/48 435/6.18 |
| 2014/0147840 | A1 | * | 5/2014 | Kim | C12Q 1/6844 435/6.11 |
| 2016/0265027 | A1 | * | 9/2016 | Sanches-Kuiper | C12Q 1/6806 |
| 2016/0340746 | A1 | * | 11/2016 | Makarov | C12O 1/6855 |
| 2018/0230533 | A1 | * | 8/2018 | Church | C12Q 1/6874 |

FOREIGN PATENT DOCUMENTS

| | | |
|---|---|---|
| EP | 1314783 A1 | 5/2003 |
| WO | 200140516 A2 | 6/2001 |

OTHER PUBLICATIONS

Beaucage et al., Tetrahedron 48(12) : 2223 (Year: 1992).*
Cushman et al.J. of Med. Chem 39 :3217 (Year: 1996).*
Daubendiek et al., JACS 117 :7818 (Year: 1995).*
Desai et al., Single-strand-specific nucleases. FEMNS Microbiology Reviews 26 :457 (Year: 2003).*
Edwards et al., Nucleiuc Acids Research 19(19) : 5227 (Year: 1991).*
Hiatt et al., Single molecule molecular inversion probes for targeted, high-accuracy detection of low-frequency variation. Genome Research 23:843 (Year: 2013).*
Kwok et al., Analytical Biochemistry 435 :181-186 (Year: 2013).*
Lizardi et al., Mutation detection and single-molecule counting using isothermal rolling-circle amplification. Nature Genetics 19:225 (Year: 1998).*
Polidoras et al.Biotechniques 41 (1) :35 (Year: 2006).*
Tessier et al. Analytical Biochemistry 158: 171 (Year: 1986).*
Product Insert for GeneAmp DNA amplification Reagent kit 2 pages (Year: 1988).*

(Continued)

*Primary Examiner* — Ethan C Whisenant
(74) *Attorney, Agent, or Firm* — Greer, Burns & Crain, Ltd.; Gregory P. Einhorn

(57) ABSTRACT

Provided in certain aspects are methods for dynamically adding molecular indexes to nucleic acid, and optionally analyzing the tagged nucleic acid. Also provided in certain aspects are methods for producing a single-stranded nucleic acid molecule from two molecules. The first molecule typically is a single-stranded nucleic acid (ssNA) containing a target sequence with optional linked nucleic acid sequences. The second molecule typically is a ssNA containing a target binding sequence and a nucleic acid sequence "tag" that is not complementary to the target sequence. The first and second ssNA molecules can be hybridized or annealed under conditions in which the target sequence and target binding sequence hybridize or anneal to each other by base pair complementarity, followed by contact of the hybridized or annealed molecules with a single-stranded nucleic acid ligase activity that ligates the 3'-end of the first ssNA molecule with the 5'phosphate (optionally adenylated) moiety of the second ssNA molecule to produce one product, a ligated ssNA molecule.

23 Claims, 22 Drawing Sheets

(56) References Cited

OTHER PUBLICATIONS

Ahern, Holly the Scientist 9(15) : 20 (Year: 1995).*
Damiani, G., et al. "Sequence analysis of heteropolymeric DNA synthesized in vitro by the enzyme terminal deoxynucleotidyl transferase and cloned in *Escherichia coli*.", Nucleic Acids Research, vol. 10, No. 20, Oct. 25, 1982, pp. 6401-6410.
Horning, Horst, "Written Opinion and International Search Report", Patent Cooperation Treaty Application No. PCT/US2015/039080, European Patent Office as International Search Authority, dated Jan. 5, 2016, 18 pages.

* cited by examiner

TAGGING AND ASSESSING A TARGET SEQUENCE

This application is a national phase application claiming benefit of priority under U.S.C. § 371 to International (PCT) Patent Application serial number PCT/US2015/039080, filed Jul. 2, 2015, which claims the benefit of priority under 35 U.S.C. § 119(e) of U.S. Provisional Application Ser. No. 62/020,823, filed Jul. 3, 2014, and U.S. Ser. No. 62/151,320, filed Apr. 22, 2015. The aforementioned applications are expressly incorporated herein by reference their entirety and for all purposes.

RELATED PATENT APPLICATION

This patent application claims the benefit of U.S. provisional patent application No. 62/151,320 filed on Apr. 22, 2015, entitled TAGGING AND ASSESSING A TARGET SEQUENCE, naming Charles Rodi as inventor, and U.S. provisional patent application No. 62/020,823 filed on Jul. 3, 2014, entitled TAGGING AND ASSESSING A TARGET SEQUENCE, naming Charles Rodi as inventor. The entire content of the foregoing patent applications, including all text, tables, figures and drawings, is incorporated herein by reference for all purposes.

FIELD

This disclosure relates to the field of genetic engineering techniques and the use of a unique identifier to label a target nucleic acid sequence for analysis and measurement.

BACKGROUND

Dawson et al, 2013, NEJM "Analysis of Circulating Tumor DNA to Monitor Metastatic Breast Cancer" reported that circulating tumor DNA levels showed a greater dynamic range, and greater correlation with changes in tumor burden, than did CA 15-3 or circulating tumor cells. Among the measures tested, circulating tumor DNA provided the earliest measure of treatment response in 10 of 19 women (53%). These observations are consistent with the view that circulating tumor DNA is an informative, inherently specific, and highly sensitive biomarker of metastatic breast cancer.

But cell-free DNA is very short, which greatly affects sensitivity. Tsui et al, 2012, PLOS ONE, "High Resolution Size Analysis of Fetal DNA in the Urine of Pregnant Women by Paired-End Massively Parallel Sequencing" reported that the median DNA target size in plasma is 168 base pairs (bp). The median DNA target sizes in urine were 29 by to 45 base pairs.

Additionally, next generation sequencing (NGS) has an accuracy rate of 99.7%, and so an error rate of 0.3% which greatly affects sensitivity and specificity, especially for biological samples wherein a mutant nucleic acid sequence of interest is present with a much higher number of non-mutant (wild type) sequences. For example, there are reports that even using hybridization-based enrichment, the best sensitivity is 1 mutant per 2500 wild type molecules (0.04%) which is difficult to reach in practice and still too high if combined with an error rate of 0.3%.

SUMMARY

The disclosure relates to the attachment of a nucleic acid sequence "tag" to a target sequence of interest. The sequence "tag" is present on a singled-stranded oligonucleotide containing a target binding sequence region that is complementary to a target sequence. Hybridization of the target binding sequence to the target sequence brings the detectable sequence "tag" into proximity of the target sequence for formation of a covalent bond between the "tag" and the target sequence.

The "tag" is optionally present with other sequences that facilitate the amplification, detection, identification, measurement, analysis and/or assessment of the target sequence and/or one or more nucleic acid sequence site(s) linked to the target sequence.

In a first aspect, the disclosure includes a method for producing a single-stranded nucleic acid molecule from two molecules. The first molecule contains a target sequence, with optional linked nucleic acid sequences, and the second molecule contains a nucleic acid sequence "tag". The first single-stranded nucleic acid (ssNA) molecule may comprise a dephosphorylated 5'-end, a target sequence and one or more optional nucleic acid sequences linked to the target sequence, and a 3'-end with optional 3'-tail sequence(s), while the second ssNA molecule comprises a 5'-phosphate moiety which is optionally adenylated, a 5' leader sequence, a target binding sequence that is sufficiently complementary to a part of the target sequence to permit hybridization thereto, and an optional 3' tail and an optionally blocked 3'-end. In the method, the first and second ssNA molecules are hybridized or annealed under conditions wherein the target sequence and target binding sequence hybridize or anneal to each other by base pair complementarity, followed by contact of the hybridized or annealed molecules with a single-stranded nucleic acid ligase activity that ligates the 3'-end of the first ssNA molecule with the 5'phosphate (optionally adenylated) moiety of the second ssNA molecule to produce one product, a ligated ssNA molecule.

In some embodiments, the 5' leader sequence of the second ssNA molecule comprises a molecular index sequence and a primer binding sequence. In some cases, wherein a plurality of first ssNA molecules containing target sequences are present, each second ssNA molecule comprises a different molecular index sequence as a unique "tag" for each target sequence, and/or one or more nucleic acid sequence site(s) linked to the target sequence, on a first ssNA molecule. A molecular index sequence also may be incorporated into a first ssNA molecule, as addressed herein.

While the method links two ssNA molecules, each molecule may contain secondary structure or one or more regions that is double-stranded in form unless hybridization between the target sequence and the target binding sequence, or ligation of the two molecules, is effectively blocked from occurring.

The first ssNA molecule may have a length up to about 500 nucleotides. The molecule may optionally be naturally occurring, such as a molecule obtained from a subject, such as a person, an animal or a plant. The first ssNA molecule also may be non-naturally occurring and in some embodiments the first ssNA molecule may include a naturally occurring portion and a non-naturally occurring portion. If the molecule is first present in double-stranded form, it may be denatured by routine methods known to the skilled person, to form single-stranded molecules. In some embodiments of the disclosure, heat denaturation is used. If the molecule is too large, or the average size of the molecules obtained from a subject is too large, the molecules may be digested or fragmented by methods known to the skilled person to produce shorter lengths for use in performing the disclosed methods.

In some embodiments, the first ssNA molecule has a length up to about 400 nucleotides, about 300 nucleotides, about 200 nucleotides, about 150 nucleotides, about 100 nucleotides, about 75 nucleotides, about 50 nucleotides, about 45 nucleotides, about 40 nucleotides, about 35 nucleotides, about 30 nucleotides, or about 25 nucleotides or less. The second ssNA molecule is synthetically produced and may have a length of about 25 nucleotides, about 30 nucleotides, about 35 nucleotides, about 40 nucleotides, about 45 nucleotides, about 50 nucleotides, about 60 nucleotides, about 70 nucleotides, about 80 nucleotides, or about 90 nucleotides or more. In a second aspect, the disclosure includes each resultant ligated ssNA molecule containing the target sequence and the nucleic acid "tag." A ligated ssNA molecule would comprise, from 5' to 3', a 5'-end that is optionally dephosphorylated, a target sequence and one or more optional nucleic acid sequence site(s) linked to the target sequence, an optional 3'-tail, a 5' leader sequence from the second ssNA molecule, a target binding sequence, and a an optional 3' tail and an optionally blocked 3'-end. As provided herein and below, this molecule uniquely labels, or "tags," a target sequence, and/or one or more nucleic acid sequence site(s) linked to the target sequence, for subsequent amplification, detection, identification, measurement, analysis and/or assessment of the target sequence or a portion thereof.

In a third aspect, the disclosure includes a method for directly "tagging" a first molecule containing a target sequence and/or one or more nucleic acid sequence site(s) linked to the target sequence. The first single-stranded nucleic acid (ssNA) molecule may comprise a dephosphorylated 5'-end, a target sequence and one or more optional nucleic acid sequence site(s) linked to the target sequence, and a 3'-end with an optional 3'-tail sequence. The method first includes extending the 3'-end of the first ssNA with a terminal transferase activity with a mixture of nucleotides under appropriate conditions to allow a random addition of a sequence to the 3'-end of the first ssNA molecule as a unique identifier sequence, or molecular index. Nucleotides often are deoxyribonucleotide triphosphates (dNTPs), which also are referred to herein as nucleotide triphosphates (NTPs), and non-limiting examples include adenosine triphosphate (dA), thymidine triphosphate (dT), cytidine triphosphate (dC), and guanosine triphosphate (dG).

The method then often negates the transferase activity, such as by heat denaturation as a non-limiting example; another non-limiting example is dephosphorylation of the substrate dNTPs. A second ssNA molecule is then introduced to the "tagged" first ssNA molecule. The second ssNA molecule may comprise a 5'-phosphate moiety that is optionally adenylated, a 5' leader sequence, a target binding sequence that is sufficiently complementary to a part of the target sequence to permit hybridization thereto, and an optional 3' tail and an optionally blocked 3'-end. In the method, the first and second ssNA molecules are hybridized or annealed under conditions wherein the target sequence and target binding sequence hybridize or anneal to each other by base pair complementarity, followed by contact of the hybridized or annealed molecules with a single-stranded nucleic acid ligase activity that ligates the 3'-end of the first ssNA molecule with the 5'phosphate moiety that is optionally adenylated of the second ssNA molecule to produce one product, a ligated ssNA molecule.

In this aspect of the disclosure, the 5' leader sequence of the second ssNA molecule does not require the presence of a molecular index sequence, and so its length may be accordingly reduced if desired. The 5' leader sequence may include a primer binding sequence, which would be present in the resultant ligated molecule.

In the above disclosed aspects of the disclosure, the ligated molecule may subsequently be partially degraded at its 3'-end such that the target binding sequence, and optionally part of the 5' leader sequence, is removed. This degradation or digestion may be mediated by contact with an appropriate single-stranded exonuclease activity as known to the skilled person. The exonuclease activity may also result in the degradation and digestion of other single-single stranded molecules. Non-limiting examples include any first and second ssNA molecules that were not ligated as described herein.

In further embodiments, the molecules may contain one or more residues or nucleotides that are targets for degradation by an endonuclease, non-limiting examples of which residues or nucleotides are one or more uracil, inosine, abasic or other modified nucleotides or residues in the target binding sequence, or the 5'-leader sequence, in the second ssNA molecule such that contact with an enzyme having an endonuclease activity may be used for additional degradation or digestion of the ligated molecule. Non-limiting examples of enzymes that can provide an endonuclease activity are uracil-DNA glycosylase (UDG), Endonuclease V, APE 1, Endonuclease III, TMA Endonuclease III and Endonuclease VIII. In many embodiments, an enzymatic activity used for degradation or digestion may be terminated by heat inactivation. In some embodiments, the 5' leader sequence contains a primer binding sequence that permits hybridization of a primer oligonucleotide for synthesis of a nucleic acid strand that is complementary to at least a portion of the ligated molecule. In some embodiments, the primer may contain an additional sequence at its 5'-end that is not complementary to the primer binding sequence.

In a fourth aspect, the disclosure includes methods of synthesizing additional copies of the target sequence by use of a disclosed ligated ssNA molecule. In some embodiments, the synthesis is of copies that are complementary to the target sequence. In some cases, the method would comprise use of a ligated ssNA molecule, that has been optionally digested or degraded as disclosed herein, and contacting it with a primer oligonucleotide that is capable of hybridizing to at least a portion of the primer binding sequence of the ligated ssNA molecule. The primer oligonucleotide and ligated ssNA molecule are then allowed to hybridize or anneal under appropriate conditions followed by contact with an appropriate polymerase activity and nucleotides to synthesize a strand complementary to the ligated ssNA molecule. This produces a duplex (double-stranded) molecule that may be denatured by appropriate reaction conditions that are then returned to hybridization conditions that allow an additional cycle of hybridization between a primer oligonucleotide and the ligated ssNA molecule followed by synthesis of another complementary strand. Of course the cycle may be repeated to permit linear amplification of the complement of the target sequence in a ligated molecule.

For embodiments in which each ligated molecule is "tagged" with a unique identifier or molecular index, each synthesized complement of the target sequence would contain the complement of the unique identifier.

In some embodiments, the synthesis of the target sequence as a duplex is provided. In some cases, the method would comprise use of a ligated ssNA molecule, that has been optionally digested or degraded as disclosed herein, and contacting it with a pair of primers for amplification of the target sequence by use of the polymerase chain reaction (PCR) as a non-limiting example. In PCR, a first primer may be the primer oligonucleotide that is capable of hybridizing to at least a portion of the primer binding sequence of the ligated ssNA molecule. The second primer may contain all or part of the target sequence such that it can hybridize or anneal to the nucleic acid strand synthesized by use of the first primer and an appropriate polymerase activity. Sometimes the second primer contains a sequence linked to the target sequence. Repeated cycles of PCR with the primers permits amplification of the target sequence as a double-stranded molecule. This amplifies the target sequence in a ligated molecule as well as the complement of the target sequence.

For embodiments in which each ligated molecule is "tagged" with a unique identifier or molecular index, each synthesized duplex of the target sequence would contain the unique identifier and its complement.

In a fifth aspect, the disclosure includes methods for the detection, identification, measurement, analysis and/or assessment of the target sequence or a portion thereof by use of synthesized copies containing the target sequence or its complement. In embodiments with ligated molecules "tagged" with a unique identifier or molecular index, each target sequence that was originally present in a first ssNA molecule can be identified, and optionally counted, by use of the identifier or index attached to the target sequence. Non-limiting examples of detection, identification, measurement, analysis and/or assessment include nucleic acid sequencing of the synthesized copies of the target sequence and detection by use of the unique identifier; determination of mass of either whole or fragmented molecules either before or after selection of one or more molecule by hybridization.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 8:
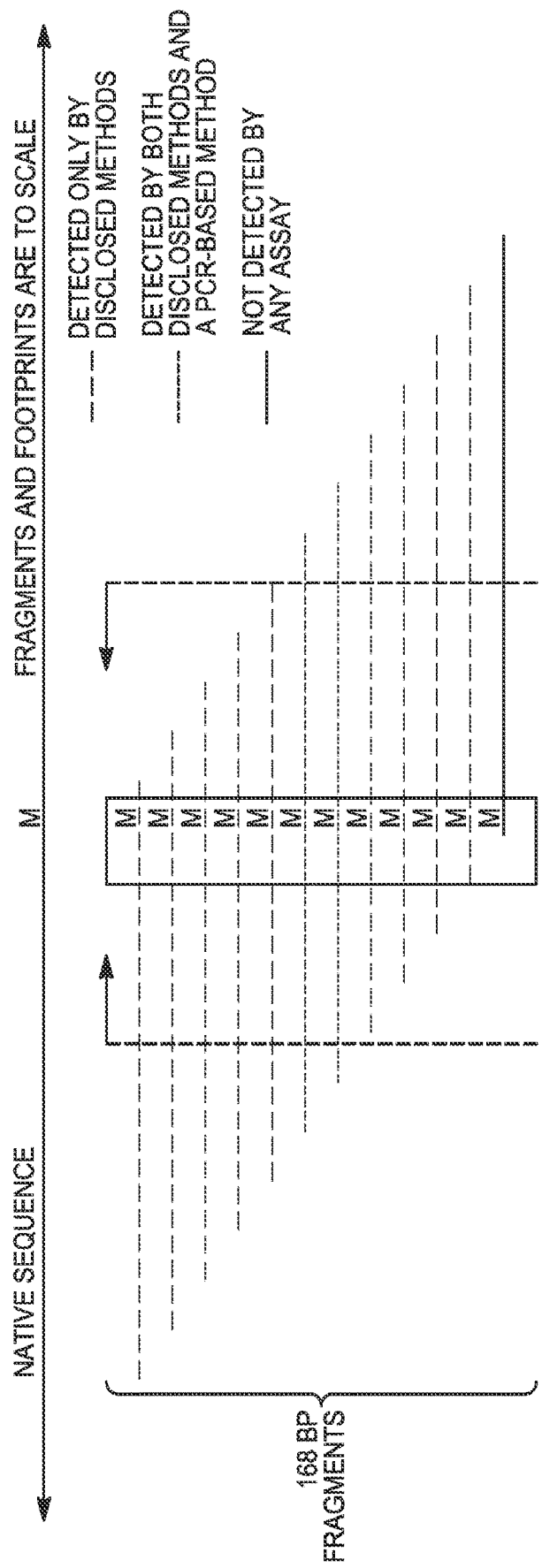
FIG. 8 illustrates options for the detection of a Site of Interest in a native sequence that has been fragmented into an average length of 168 base pairs.

The fragmented size of cell-free nucleic acids, such as cell-free DNA present in blood and urine, has been previously reported. For a given nucleic acid sequence of interest, or site of interest, that is present in a native sequence, random fragmentation of the native sequence results in a plurality of possible fragments containing the site of interest. This is illustrated in FIG. 8, where a native sequence is shown at the top with an "M" site of interest, for example. Twelve representative fragments of 168 bp in length and containing M are shown. For a hypothetical PCR based assay with a 120 bp footprint defined by the forward and reverse primers, the only three of the representative fragments will be detected as indicated by the pair of arrows.

The disclosed methods include embodiments with a target sequence of about 23 nucleotides in a first ssNA molecule and are indicated as able to detect those three fragments as well as eight others. The disclosed methods may use the sequence on both sides of M as the target sequence in a first ssNA molecule disclosed herein. Each strand of the native sequence provides an available target sequence linked to M that may be for hybridization to a corresponding target binding sequence as disclosed herein to permit the production of a ligated molecule.

Table 1 shows the expected detection of small nucleic acid molecules based upon their size and the "footprint" size of the assay:

TABLE 1

| Expected Percent of Molecules Detected | | | | | |
|---|---|---|---|---|---|
| Target size (bp) | | | | | |
| 168 | | | 45 | | |
| Assay size (bp) | | | | | |
| 208 | 120 | 23 | 208 | 120 | 23 |
| Percent detected 0 | 29 | 87* | 0 | 0 | 51* |

The asterisk in Table 1 indicates the overall detection rates can increase significantly when a non-competing assay from the other side of the site of interest is included.

The disclosed methods and molecules often are based on the shortest sequence that makes the sequence unique in the human genome. Only the target sequence, and any linked sequence or site of interest, needs to be present for successful tagging of the target sequence because relative to a PCR based assay, the "second" primer site is provided by the second ssNA molecule of the disclosure. Use of the shortest unique sequences permits an ultra-short assay methodology.

The disclosed methods also assure specificity by use of molecular indexing wherein each native ssNA molecule in a sample is tagged with a unique nucleotide-encoded identifier, or "barcode." The native sequence per se, the length of the native sequence, and the length of the optional oligoT tail also contribute to the uniqueness of each molecule tagged by a disclosed method. Sometimes the oligo dT tail may be an oligo dA tail, an oligo dC tail, an oligo dG tail or a tail comprised of one oligo (dT, dA, dC, or dG) in tandem with a second oligo (dT, dA, dC, or dG) that is different from the first, all of which would contribute to the uniqueness of the each molecule tagged by a disclosed method.

Moreover, linear amplification of the disclosed ligated (tagged) molecules assures that mutant and wild type molecules are scored correctly. In embodiments where the disclosed target binding sequences and primers are only linked to, or adjacent to, a Site of Interest (e.g. do not encode mutant or wild type sequences) they cannot contribute to the scoring of mutant and wild type molecules.

Methods for Tagging ssNA Molecules

As described herein, the disclosure includes a method for producing a single-stranded nucleic acid molecule from two molecules. Thus, tagging methods generally act on two single-stranded NA and generate a single-stranded NA. In some embodiments, the method comprises ligating a first and a second ssNA molecule after they have hybridized or annealed to each other. The first single-stranded nucleic acid (ssNA) molecule comprises a 5'-end that is optionally dephosphorylated, a target sequence, and a 3'-end with an optional 3'-tail sequence, while the second ssNA molecule comprises a 5'-phosphate moiety that is optionally adenylated, a 5' leader sequence, a target binding sequence that is the complement of the target sequence, and an optional 3' tail and an optionally blocked 3'-end. The molecules are placed under conditions wherein the target sequence and target binding sequence hybridize or anneal to each other by base pair complementarity and then contacted with a single-stranded nucleic acid ligase activity that ligates the 3'-end of the first ssNA molecule with the 5'phosphate moiety that is optionally adenylated of the second ssNA molecule to produce a single ssNA molecule.

Whether the 5' end of the second ssNA is adenylated can depend on the single-stranded ligase enzyme utilized for ligating the first ssNA to the second ssNA. Also, whether adenosine triphosphate is included or not included in ligation conditions also depends on the single-stranded ligase enzyme utilized for ligation. The following Table 2 shows different non-limiting examples of combinations of single-stranded ligase enzymes, first ssNA and second ssNA.

TABLE 2

Adenylated and non-adenylated second ssNA molecule combinations

| Enzyme | ATP Required | first ssNA | second ssNA |
| --- | --- | --- | --- |
| CircLigase* | Yes | dephosphorylated 5' end, free 3' end | blocked 3' end, phosphorylated or adenylated 5' end |
| CircLigase II* | "No" | dephosphorylated 5' end, free 3' end | blocked 3' end, phosphorylated or adenylated 5' end |
| T4 RNA Ligase 1** (ssRNA Ligase) | Yes | dephosphorylated 5' end, free 3' end | blocked 3' end, phosphorylated or adenylated 5' end |
| Thermostable 5' AppDNA/RNA Ligase** | No | phosphorylated 5' end, free 3' end | blocked 3' end, adenylated 5' end |
| CircLigase* | Yes | phosphorylated 5' end, free 3' end | blocked 3' end, phosphorylated or adenylated 5' end |
| CircLigase II* | "No" | phosphorylated 5' end, free 3' end | blocked 3' end, phosphorylated or adenylated 5' end |
| T4 RNA Ligase 1** (ssRNA Ligase) | Yes | phosphorylated 5' end, free 3' end | blocked 3' end, phosphorylated or adenylated 5' end |

*e.g., from Epicentre Biotechnologies Corporation
**e.g., from New England BioLabs, Inc. for example A blocked 3' end may be a 3' end that has a nucleotide or non-nucleotide end that prevents ligation; it may also be in a state (e.g. double-stranded) that is not recognized by ssNA ligases. In cases where the 5' end of the first ssNA is phosphorylated, the second ssNA may have a competitive advantage over the first ssNA by virtue of proximity to the 3' end of the first ssNA.

Because the CircLigase II enzyme noted in Table 2 is pre-adenylated, no added ATP is necessary and the enzyme works stoichiometrically. The thermostable 5' AppDNA/RNA ligase enzyme noted in Table 2 is a mutant enzyme that cannot adenylate the 5' phosphate of RNA or ssDNA, and it requires that the second ssNA has a pre-adenylated 5' end. The second ssNA often includes a blocked 3' end to prevent circularization. The first ssNA often includes a dephosphorylated 5' end to prevent circularization when CircLigase, CircLigase II, and T4 RNA Ligase 1 enzymes are utilized. When using thermostable 5' AppDNA/RNA ligase enzyme there is no need to dephosphorylate the 5' end of the first ssNA since the enzyme cannot adenylate the 5' end.

Thus in some embodiments, a first ssNA having a dephosphorylated 5' end and free 3' end is utilized with a second ssNA having a blocked 3' end and phosphorylated 5' end. In the latter embodiments, ligation conditions include adenosine triphosphate (ATP) or do not include ATP, depending on the ligase utilized (e.g., see examples in Table 2 above). In certain embodiments, a first ssNA not having a dephosphorylated 5' end (e.g., having a phosphorylated 5' end) and a free 3' end is utilized with a second ssNA having a blocked 3' end and an adenylated 5' end. In the latter embodiments, ligation conditions often do not include ATP. For purposes of clarity, ligating the 3' end of a first ssNA with the 5' phosphate moiety of a second ssNA can be performed when the 5' terminus of the second ssNA is already adenylated (i.e., terminal adenyl moiety linked to an adjacent phosphoryl moiety)

Methods may be performed in certain embodiments with a first ssNA molecule from a biological specimen or sample. In some cases, the specimen or sample is from an animal, such as a canine, feline, equine, bovine, caprine, ovine, porcine, avian, ape or human subject, or a plant. Non-limiting examples of a specimen or sample include cellular nucleic acids, and cell-free nucleic acids (e.g., circulating cell-free nucleic acid), derived from bodily fluids including blood, plasma, serum, saliva, cerebrospinal fluid, and urine. In some cases, the ssNA is obtained after fragmentation of larger nucleic acids in the specimen or sample. The ssNA may also be prepared by denaturation of double-stranded nucleic acids.

With a first ssNA molecule from a biological specimen or sample, the 3'-tail sequence is a native sequence found adjacent to, or linked to, a target sequence. The 3'-tail sequence may optionally contain a position or site of interest as described herein. As apparent from the disclosure, a position or site of interest would be 3' from the target sequence in such cases. A first ssNA molecule from a biological specimen or sample may be considered a "native" ssNA molecule that occurs in nature or is derived from a naturally occurring molecule, such as a cell-free double-stranded DNA, in certain embodiments. In most embodiments of the disclosure, a native ssNA molecule may be dephosphorylated (as addressed herein) by methods known to the skilled person. Dephosphorylation provides the benefit of reducing undesired self-ligation of a first ssNA molecule as addressed herein.

Methods may be performed in some embodiments with a first ssNA molecule that has been processed for use in a disclosed method. In some embodiments, a first ssNA molecule is extended by use of terminal transferase activity to introduce an oligoT tail. Instead of an oligo dT tail, an oligo dA tail, an oligo dC tail, an oligo dG tail, or a tail comprised of one oligo (dT, dA, dC, or dG) in tandem with a second oligo (dT, dA, dC, or dG) that is different from the first, may be added to the first ssNA. Sometimes a homopolynucleotide is referred to as a "flag" or "mark." Sometimes a flag, mark, and molecular index are in a different order. In some cases, the tail may be used to aid in the ligation to the second ssNA molecule. In these embodiments and others, a first ssNA molecule may also comprise a 5' target leader sequence. With a first ssNA molecule from a biological specimen or sample, the 5' target leader sequence is a sequence found adjacent to, or linked to, a target sequence. The 5' target leader sequence in a first ssNA molecule often is a native sequence with respect to the target sequence. In some cases, a position or site of interest may be present in the 5' leader sequence and so be 5' from the target sequence. Additionally, a sequence on the 3' side of the target sequence, if present, may be considered a target tail sequence. A 3' target tail sequence in a first ssNA molecule often comprises, or is, a native sequence with respect to the target sequence. If present, a target tail sequence may be any length or sequence that does not bar ligation between a first ssNA molecule and a second ssNA molecule. In some embodiments, a target tail, if present, may be from one to about 500 nucleotides in length.

The target sequence is of a length and sequence that is unique among the nucleic acid sequences and moieties within a sample or specimen. Sometimes the target sequence may be a flag or mark sequence that has been added to a plurality of the molecules in the sample or specimen and therefore may not be unique. In some cases, it is of a length of about 18 nucleotides or less, about 19 nucleotides or less, about 20 nucleotides or less, about 21 nucleotides or less, about 22 nucleotides or less, about 23 nucleotides or less, about 24 nucleotides or less, about 25 nucleotides or less, about 26 nucleotides or less, about 27 nucleotides or less, or about 28 nucleotides or more. In certain embodiments, the target sequence may be 35 nucleotides or more, or 40 nucleotides or more, or 50 nucleotides or more, or 70 nucleotides or more. In the target binding sequence of a second ssNA molecule, locked nucleic acids (LNAs) may be used to decrease the size of the cognate target sequence for hybridization. Accordingly, the second ssNA molecule may contain one or more modified nucleotides, uracil residues, inosine residues, abasic sites, or other nucleic acid modifications as desired by the skilled person. In some cases, the 5' end of a second ssNA molecule may comprise ribonucleotides such that the molecule is a DNA/RNA chimera. In some cases, the 5' end of a second ssNA molecule may comprise nucleotides of a type not found in nature.

In many embodiments, a target sequence and the target binding sequence, when hybridized or annealed, has a melting temperature of about 50° C., about 55° C., about 60° C., about 65° C., or about 70° C. or higher. In some embodiments, a target sequence and the target binding sequence, when hybridized or annealed, has a melting temperature of about 40° C. or about 45° C.

In many embodiments, the method may be performed with a second ssNA molecule that is phosphorylated or optionally adenylated at the 5'-end. Additionally, a second ssNA molecule may have a guanine (G) residue at the 5'-end to assist in ligation to the first ssNA molecule. Moreover, a second ssNA molecule may contain a 5' leader sequence that comprises a molecular index (unique nucleic acid) sequence and a primer binding sequence. In embodiments for which there is a plurality of first ssNA molecules, such as a biological specimen or sample, each second ssNA molecule may contain a different molecular index sequence. Molecular index sequence diversity is described in greater detail herein.

Moreover, a second ssNA molecule may include a blocked 3'-end to prevent self-ligation, a primer binding site of about 18 nucleotides or more in length, and/or a molecular index of about 10 nucleotides or more. In embodiments disclosed herein with a molecular index added to the first ssNA molecule, the skilled person would understand that the second ssNA molecule is not necessary for providing a unique identifier to the first ssNA molecule. Nonetheless, the second ssNA molecule may still comprise an additional molecular index to provide two identifiers to a target sequence.

After the first and second ssNA molecules are combined, such as in a reaction mixture, they may be denatured and then slowly annealed to allow hybridization of the target sequence in the first ssNA molecule to the target binding sequence in the second ssNA molecule. The target sequence in the first ssNA molecule and the target binding sequence in the second ssNA molecule may be considered to form a "clamp" that brings the 3'-end of the first ssNA molecule and the 5'-end of the second ssNA molecule into proximity for ligation. After hybridization or annealing, a ligase activity may be used to ligate the hybridized or annealed molecules. The resulting ligated single ssNA molecules are products of the disclosure as described herein.

After ligation, the single ssNA product molecules may be considered to be a "hairpin loop" structure with a duplex region formed by the hybridization of the target sequence and target binding sequence with a loop formed by ligation. The single ssNA product sometimes comprises a hairpin structure at 25 degrees Celsius. The loop may be of any size accepted by a single-stranded ligase activity. Non-limiting examples include from about 15 nucleotides or more, about 20 nucleotides or more, about 30 nucleotides or more, about 40 nucleotides or more, about 50 nucleotides or more, about 75 nucleotides or more, about 100 nucleotides or more, about 150 nucleotides or more, about 200 nucleotides or more, about 300 nucleotides or more, about 400 nucleotides or more, or about 500 nucleotides or more. In some embodiments, the hairpin structure comprises a loop of about 5 nucleotide bases to about 500 nucleotide bases in length. In certain embodiments, the hairpin structure comprises a partially double-stranded region and a single-stranded region, and the double-stranded region is of about 18 nucleotides to about 35 or more nucleotide bases in length. Non-limiting examples of a ligase activity include thermostable ssDNA ligases commercially available as CircLigase™ and CircLigase™ II and the thermostable 5' App DNA/RNA ligase from *M. thermoautotrophicum*.

After the ligation reaction, the mixture may be heated to inactivate the single-stranded ligase, in some embodiments. The mixture sometimes is contacted with a single-stranded exonuclease activity to digest single-stranded molecules, such as unreacted first and second ssNA molecules. A non-limiting example of an appropriate exonuclease activity is exonuclease I as known to the skilled person. The double-stranded 3'-ends of ligated molecules make them resistant to exonuclease digestion, and unligated molecules are subject to digestion. The digestion may be followed by optional heat inactivation of the exonuclease activity.

In some embodiments, the reaction may then be contacted with a uracil-DNA glycosylase activity to digest at uracil containing positions present in the former second ssNA molecule. In many embodiments, the uracil containing positions are within the target binding sequence or within close proximity and 5' from the target binding sequence. After UDG treatment, the enzymatic activity is optionally heat inactivated. The resulting processed molecules are also products of the disclosure as described herein.

Enhancing Overall Detection Rates

As noted herein, the overall detection rates can increase significantly when a non-competing assay from the other side of a site of interest is included in an assay. Thus in some embodiments, the first ssNA molecule is from a double-stranded nucleic acid (dsNA) molecule, or partially dsNA and partially ssNA molecule, comprising a sense first ssNA molecule and an antisense first ssNA molecule that can be targeted independently by a sense second ssNA molecule and an antisense second ssNA molecule, respectively. The sense first ssNA molecule and an antisense first ssNA molecule can be separated from one another under denaturing conditions (e.g., application of heat, application of chemical denaturants). The sense first ssNA molecule and the antisense first ssNA molecule can be contacted under hybridization or annealing conditions with (i) a sense second ssNA molecule comprising a target binding sequence complementary to the target sequence in the sense first ssNA molecule, and (ii) an antisense second ssNA molecule comprising a target binding sequence complementary to the target sequence in the antisense first ssNA molecule, thereby producing hybridized or annealed molecules. Under the hybridization or annealing conditions, at least a portion of the target sequence and the target binding sequence in the sense first ssNA molecule and the sense second ssNA molecule, and at least a portion of the target sequence and the target binding sequence in the antisense first ssNA molecule and the antisense second ssNA molecule, hybridize or anneal to each other by base pair complementarity. The hybridized or annealed molecules often are contacted with a single-stranded nucleic acid ligase activity under ligation conditions. Under the ligation conditions, the 3' end of the sense first ssNA molecule ligates to the 5' phosphate moiety (optionally adenylated) of the sense second ssNA molecule, and the 3' end of the antisense first ssNA molecule ligates to the 5' phosphate moiety (optionally adenylated) of the antisense second ssNA molecule, thereby generating single ssNA molecules. Features described herein pertaining generally to first ssNA and second ssNA molecules can pertain to sense first ssNA, sense second ssNA, antisense first ssNA and antisense second ssNA molecules. Given that the 3' end of the sense and antisense first ssNA molecules ligate to the 5' end of the sense and antisense second ssNA molecules, the sense second ssNA molecule and the antisense second ssNA molecule effectively target both sides of the site of interest.

Incorporation and Use of Molecular Index Sequences

The disclosure further includes a method for producing a first single-stranded nucleic acid (ssNA) molecule that is tagged with a unique identifier and then ligated to a second ssNA molecule. A first ssNA molecule may be any as described herein before processing and contacted with a second ssNA molecule. A first ssNA molecule may be a single-stranded molecule obtained or prepared from a biological specimen or sample described herein, and is extended at its 3'-end with random incorporation of nucleotides (also known as nucleotide residues) sufficient to create a randomly-generated, unique molecular index of nucleotides linked to each first ssNA molecule. This unique sequence is referred to as a molecular index sequence, or "index" or "index polynucleotide," and is added to a nucleic acid by a process referred to herein as "dynamic molecular indexing" (DMI). The addition of this unique polynucleotide (or unique sequence) to each first ssNA may be performed by use of a terminal transferase activity in the presence of a mixture of dNTPs or NTPs. After attachment of a unique polynucleotide (or unique sequence) as a tag, the first ssNA molecule may be optionally extended at its 3'-end with an oligoT tail or an oligoA tail provided by the instant disclosure.

A first ssNA molecule tagged by use of a terminal transferase activity may be considered to have been "directly" tagged while a first ssNA molecule tagged by ligation to a second ssNA molecule may be considered to have been "indirectly" tagged. Before or after preparation of a directly tagged first ssNA molecule, it may be dephosphorylated at its 5'-end as provided by the instant disclosure. A directly tagged first ssNA molecule is a product of the disclosure as described herein.

The addition of 10 random nucleotides, whether by direct tagging or as a molecular index on a second ssNA, provides over one million possible unique sequence tags. Use of 20 random nucleotides generates over one trillion possible unique tags. In the case of a biological specimen or sample, the number of possible ssNA molecules to be tagged can be easily vastly outnumbered by the number of possible molecular indices.

Figure 1:
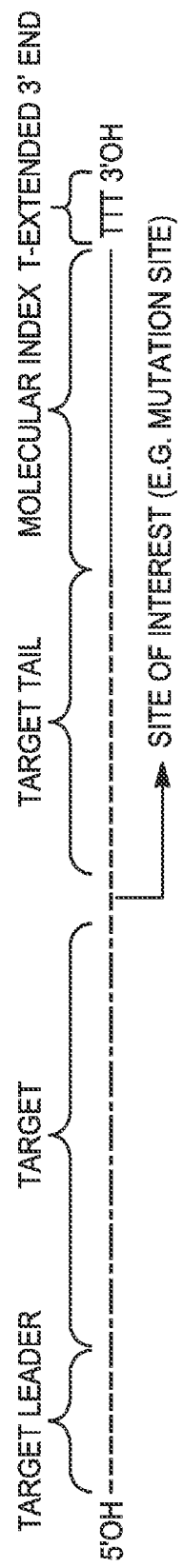
FIG. 1 illustrates a non-limiting representative embodiment of a first ssNA molecule of the disclosure. The molecule begins with a dephosphorylated 5'-end (5'-OH moiety) followed by a Target Leader sequence (which is optional), the Target sequence, a Target Tail (which is optional), a Molecular Index (introduced by a terminal transferase activity as provided by some disclosed embodiments) and an oligo T tail (introduced by a terminal transferase activity as disclosed herein). Sometimes the oligo dT tail may be an oligo dA tail, an oligo dC tail, an oligo dG tail or a tail that includes one oligo (dT, dA, dC, or dG) in tandem with a second oligo (dT, dA, dC, or dG) that is different from the first. Sometimes the tail may be referred to as a "flag" or "mark". Sometimes the flag, the mark, and the molecular index may be in a different order. A Site of Interest, such as a mutation site within the Target Tail that is linked to the target sequence, is also shown as a non-limiting example.
Figure 2:
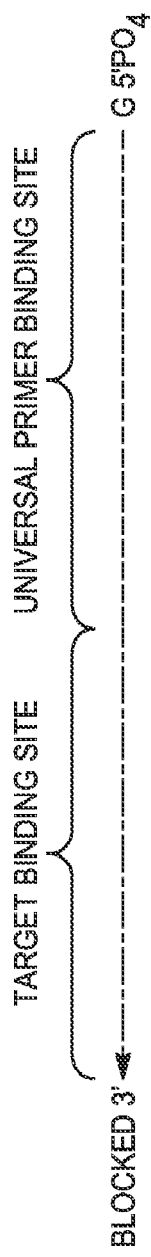
FIG. 2 illustrates a non-limiting representative embodiment of a second ssNA molecule of the disclosure. The molecule is represented from left to right in the 3' to 5' orientation. From 3' to 5', the molecule contains a blocked 3'-end (which is optional), a Target Binding Site (or target binding sequence), a Universal Primer Binding Site, and a guanine residue at the 5'-end which is phosphorylated.
Figure 3:
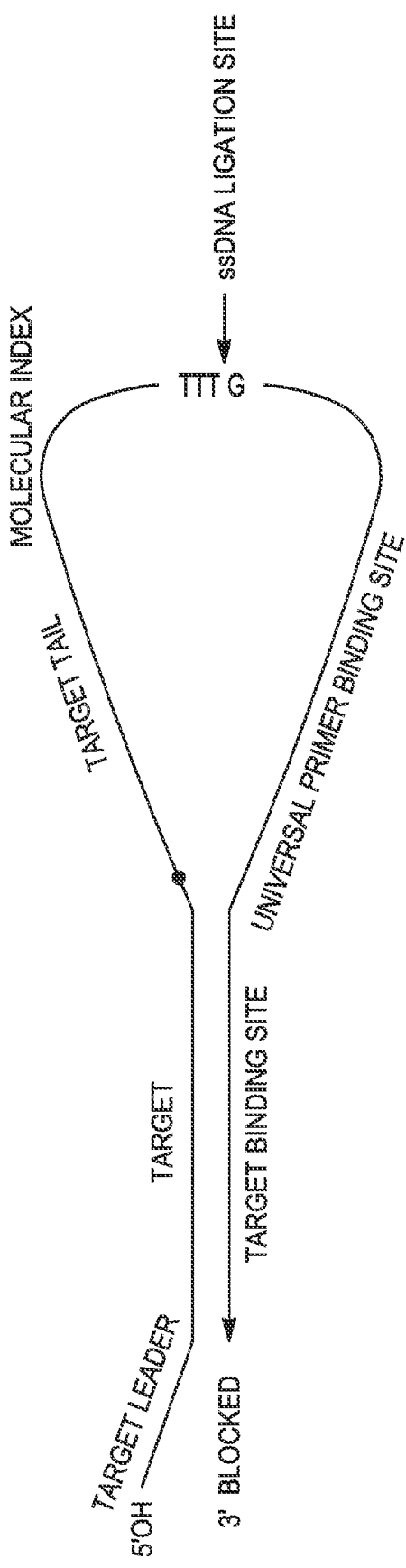
FIG. 3 shows a non-limiting representative embodiment of the ssNA molecules of the disclosure suitable for ligation. The first ssNA molecule is in the upper part of the figure and begins with a dephosphorylated 5'-end (5'-OH moiety) followed by a Target Leader sequence (which is optional), the Target sequence, a Target Tail (which is optional), a Molecular Index (introduced by a terminal transferase activity as provided by some disclosed embodiments) and an oligoT tail (introduced by a terminal transferase activity as disclosed herein). The second ssNA molecule is in the lower part of the figure and is represented left to right in the 3' to 5' orientation with complementarity between its Target Binding Site (or target binding sequence) and the Target sequence of the first ssNA molecule. From 3' to 5', the second ssNA molecule contains a blocked 3'-end (which is optional), a Target Binding Site (or target binding sequence), a Universal Primer Binding Site, and a guanine residue at the 5'-end which is phosphorylated or adenylated (not shown). The site for single-stranded ligase activity between the two strands is shown by the arrow.
Figure 4:
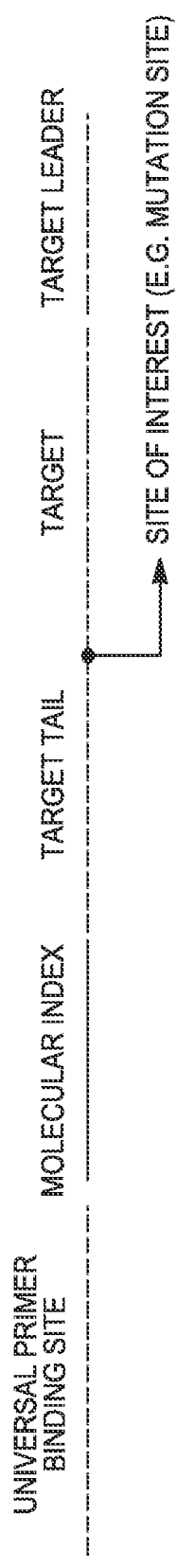
FIG. 4 illustrates a representative ligated molecule corresponding to FIG. 3 after digestion of its 3'-end with UDG activity which digests within the Target Binding Site. The molecule contains a Site of Interest, such as a mutation site within the Target Tail that is linked to the target sequence, and is suitable for hybridization with a primer oligonucleotide via the Universal Primer Binding Site.

FIG. 1 illustrates a directly tagged first ssNA molecule of the disclosure. It may be used with a second ssNA molecule as illustrated in FIG. 2. The preparation and processing of a directly tagged first ssNA molecule and a second ssNA molecule may be performed as described throughout the instant disclosure. FIG. 3 illustrates an arrangement of a directly tagged first ssNA molecule and a second ssNA molecule of the disclosure. The ligation between a directly tagged first ssNA molecule and a second ssNA molecule, and further processing of a ligated product may be performed as described throughout the instant disclosure. FIG. 4 illustrates a ligated and processed product formed from a directly tagged first ssNA molecule and a second ssNA molecule of the disclosure. The resulting ligated and/or processed molecules are products of the disclosure as described herein.

Herein DMI is a process by which a molecular index is created by the sequential addition of nucleotide monomers to a nucleic acid (e.g., nucleic acid in a specimen or sample; a first ssNA; a second ssNA) through a terminal transferase activity. If a single type of nucleotide monomer is added sequentially, then a homopolymer, which also is referred to as a "homopolynucleotide," is added to the nucleic acid. If two or three or four types of nucleotide monomers are added sequentially, then a heteropolymer, which also is referred to as a "heteropolynucleotide," is added to the nucleic acid. Homopolymers (e.g., flags and marks), and heteropolymers (e.g., molecular indexes), may be added in any order to ssNA or dsNA. Furthermore, a homopolynucleotide may be used to anneal a second ssNA to a first ssNA. In certain embodiments, these two ssNA molecules may be subsequently ligated together, and in some embodiments, the second ssNA can be extended. The first ssNA may be naturally single-stranded or may be derived from a dsNA or a partially dsNA.

Figure 15:
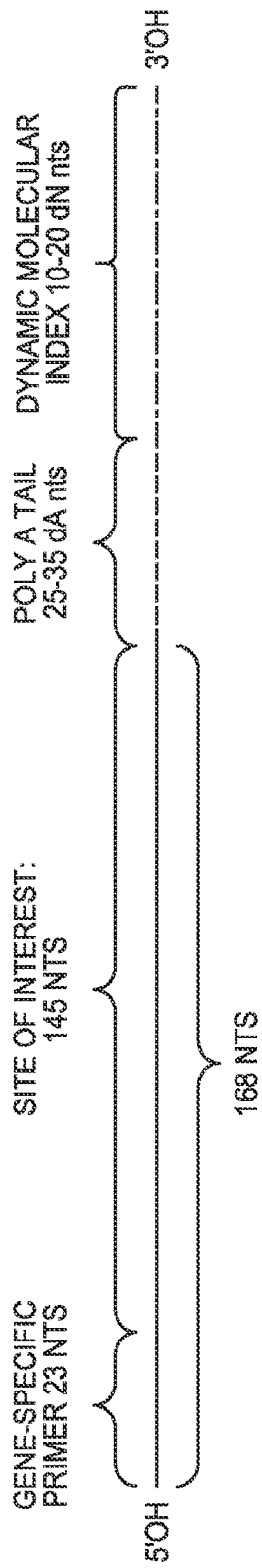
FIG. 15 shows an example of how dynamic molecular indexing can lead to great diversity in tagging a sequence.

A molecular index often includes two or more different nucleotides (i.e. a heteropolymer) that by itself or in combination with a flag (i.e. a homopolymer) or a mark (i.e. a homopolymer of a type different from a flag) or a nucleic acid in a specimen or sample that may vary in sequence and/or length, results in an overall sequence that is unique or virtually unique to the molecule to which it is contiguous. As a non-limiting example, referring to FIG. 15, a molecule in a specimen of cell-free DNA that has a homopolymer tail (or flag) of 25 to 35 dA residues followed by molecular index of 10 to 20 random nucleotides and a site of interest that can occur anywhere within a span of 145 nucleotides, would have a potential diversity of approximately $1.5 \times 10^9$ to approximately $1.5 \times 10^{15}$. Since a 100 ng specimen of cell-free DNA from a 20 mL blood specimen would contain only about $3 \times 10^4$ DNA molecules of any particular sequence, it would be virtually impossible for two different original molecules of a particular type to have the same molecular index.

Figure 5:
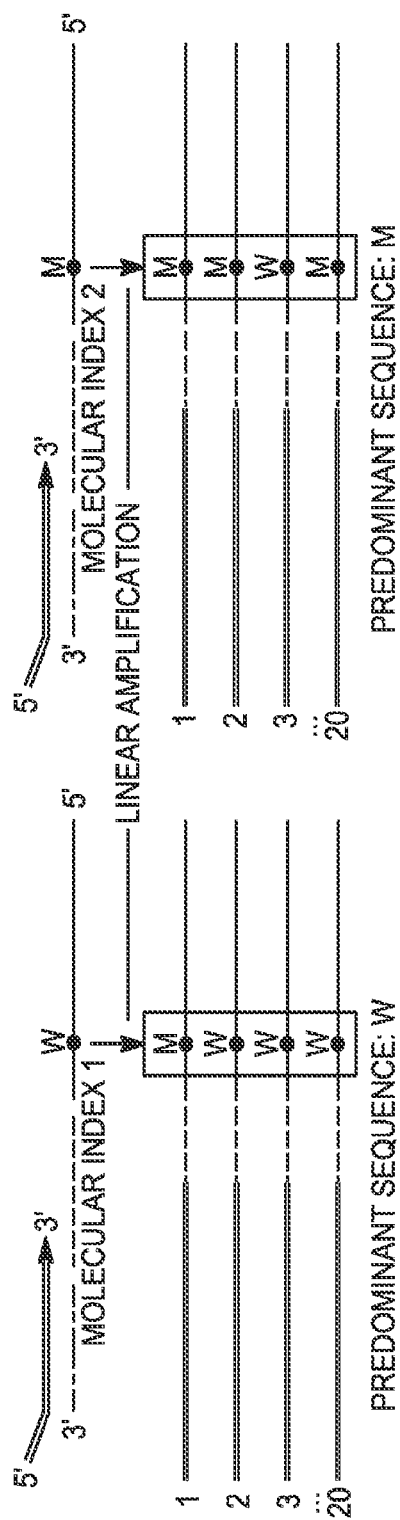
FIG. 5 illustrates a representative linear amplification of two molecules corresponding to FIG. 4. On the left is an illustration wherein the Site of Interest is non-mutated (or wild type as indicated by "W") and linked to Molecular Index 1. On the right is an illustration wherein the Site of Interest is mutated (as indicated by "M") and linked to Molecular Index 2. Linear amplification of each molecule with a primer oligonucleotide that may contain an optional extension at the 5'-end, produces copies of the complement of the ligated molecule. The extension may be an adapter sequence to facilitate sequencing of the amplified molecules, such as by use of next generation sequencing (NGS) techniques. Given possible errors due to polymerase activity, errors introduced at the Site of Interest may be identified and disregarded based on the predominance of the sequence at the Site as determined by sequencing. Sometimes other sources of error may be similarly identified and disregarded based on the predominance of the sequence at the Site of Interest as determined by sequencing. Predominance may be determined based in part on the Molecular Index present on the amplified copies.
Figure 6:
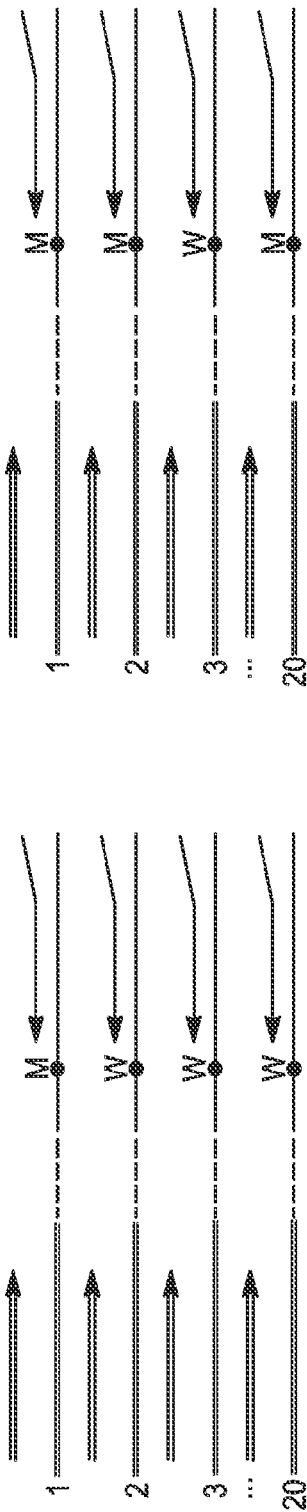
FIG. 6 illustrates a representative double-stranded amplification of the molecules corresponding to FIG. 5 for attachment of a second adapter sequence. Target-specific primers with an adapter sequence at their 5'ends may be used in combination with a forward primer oligonucleotide to amplify products from FIG. 5. The adapter sequences may be NGS adapter sequences.

The disclosure includes products produced by the disclosed methods of creating a NA molecule with a molecular index added by a DMI process. These include ligated molecules, and processed versions thereof, as disclosed. FIGS. 5 and 6 illustrate possible uses of the ligated molecules for further amplification, detection, identification, measurement, analysis and/or assessment of a target sequence and/or one or more nucleic acid sequence site(s) linked to the target sequence. A nucleic acid sometimes includes an index heteropolynucleotide (an indexed nucleic acid), a flag homopolynucleotide (a flagged nucleic acid), a mark homopolynucleotide (a marked nucleic acid) or combination thereof. A flag homopolynucleotide or a mark homopolynucleotide sometimes is a tandem homopolynucleotide comprising a first polynucleotide consisting of a first nucleotide (e.g., about 5 to about 100 nucleotides in length) and a second polynucleotide directly joined to the first polynucleotide that consists of a second nucleotide (e.g., also about 5 to about 100 nucleotides in length). A DMI process for generating a tagged, flagged and/or marked nucleic acid sometimes (i) acts on a single-stranded NA and generates a single-stranded NA, (ii) sometimes acts on a double-stranded NA and generates a partially double-stranded and partially single-stranded NA, and (iii) sometimes acts on a partially single-stranded and partially double-stranded NA and generates a partially double-stranded/partially single-stranded NA.

Figure 7:
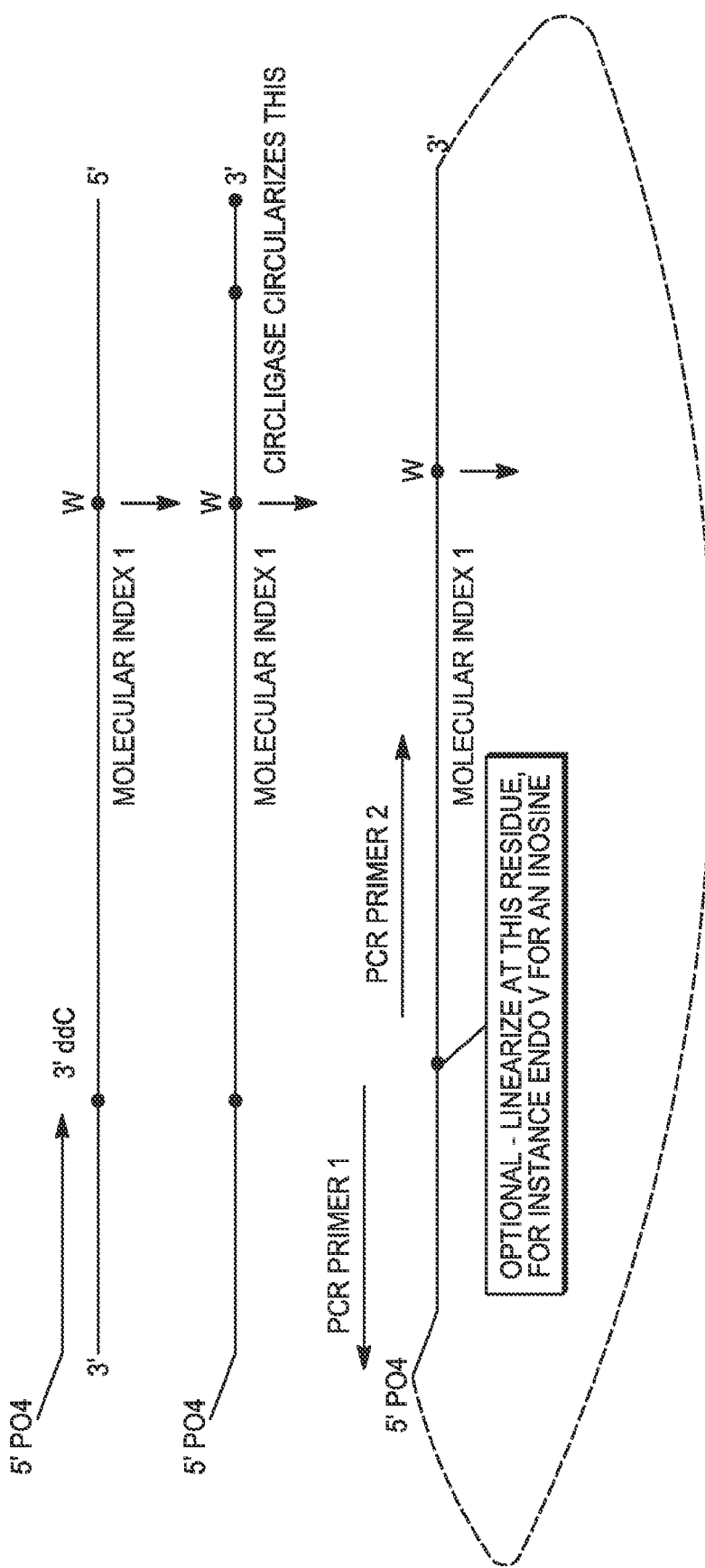
FIG. 7 illustrates an alternative embodiment of the disclosure for the amplification, detection, identification, measurement, analysis and/or assessment of a target sequence and/or one or more nucleic acid sequence site(s) linked to the target sequence. In certain embodiments, the 3' ddC end of the primer may be removed by an activity of a proof-reading polymerase, thus allowing extension.

In some embodiments, the disclosure includes a ligated molecule as illustrated in FIG. 7, that is contacted by a primer that contains a blocked 3' end (3'ddC residue as an illustrative example). The blocked 3' end often is removed by an appropriate exonuclease activity or other activity that may be associated with a polymerase and the primer is then extended by an appropriate polymerase to create a molecule that is complementary to the ligated molecule.

The complementary strand then often is circularized with a single-strand ligase activity and for further amplification, detection, identification, measurement, analysis and/or assessment of a target sequence and/or one or more nucleic acid sequence site(s) linked to the target sequence, by use of PCR primer 1 to produce a first strand, and PCR primer 2 that is complementary to the first strand for production of a complementary second strand.

Optionally, the circularized molecule is linearized within the region complementary to the primer binding sequence to allow PCR based reactions to occur on a linear substrate. A non-limiting example of linearization is with use of endonuclease V for an inosine residue within the region complementary to the primer binding sequence.

Molecularly indexed molecules allow the precise counting of molecules and accurate determination of sequence in a specimen or sample. Since each molecule in a specimen or sample has a unique or virtually unique molecular index attached to it, every incidence of a particular molecular index results from the same original molecule. Linear or exponential amplification does not distort the number of original molecules. Referring to FIG. 5, for example, linear amplification of two molecularly indexed molecules results in 20 copies of each original molecule. Although 40 molecules are subsequently sequenced, only two molecular indexes (Molecular Index 1 and Molecular Index 2 in this example) are found and it is therefore determined that there were only two original molecules in the sample or specimen. Also, since each copy of each original molecule is an independent event, a consensus sequence may be determined for each original molecule revealing its true sequence. In FIG. 5, for example, Molecular Index 1 is associated with a wild type molecule and Molecular Index 2 is associated with a mutant molecule. Similar precise counting and accurate sequence determination is possible for exponential amplification, as illustrated in FIG. 6 for example. Precise counting and accurate sequence determination may be applied to the detection of genetic differences, including but not limited to, point mutations, substitutions, insertions, deletions, inversions, duplications, copy number variations, translocations, single nucleotide polymorphisms (SNPs), and fusion transcripts. Precise counting and accurate sequence determination also may be applied to the detection of molecules that do not differ at the site of interest, thereby allowing the precise counting of molecules including but not limited to species of mRNA, miRNA, lncRNA, and DNA. Precise counting of RNA molecules is useful for certain applications, such as determining a particular prognosis for a patient or diagnostic of certain disease states, for example. Precise counting of DNA molecules is useful for certain applications, such as determining certain aneuploidies using cell-free nucleic acid, for example.

In certain embodiments, provided is a method for modifying a nucleic acid, that includes: contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding an index heteropolynucleotide comprising nucleotides in the mixture to the 3' end of the nucleic acid and generating an indexed nucleic acid. Also provided in certain embodiments is a method for modifying a nucleic acid, that includes: contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a modified nucleic acid. The nucleic acid modified or produced by such methods sometimes is a first ssNA or a second ssNA described herein.

A terminal transferase activity can be provided in any suitable manner. A terminal transferase activity often is provided by an enzyme that catalyzes the addition of nucleotides to the 3' terminus of a nucleic acid. Such an enzyme can add nucleotides to the 3' terminus of a nucleic acid (e.g., DNA or RNA). In certain embodiments, an enzyme adds nucleotides to the 3' terminus of a single-stranded nucleic acid, and sometimes adds nucleotides to double-stranded nucleic acid having a 3' overhang, blunt ends, or recessed ends. An enzyme having terminal transferase activity often is a specialized polymerase that does not require a template. An enzyme having terminal transferase activity sometimes utilizes cobalt, magnesium or manganese as a co-factor. A non-limiting example of an enzyme having terminal transferase activity is commercially available (e.g., New England BioLabs catalog no. M0315S). An enzyme having terminal transferase activity sometimes is referred to as Terminal deoxynucleotidyl transferase (TdT) or a DNA nucleotidylexotransferase (DNTT). Non-limiting examples of other enzymes that can have terminal transferase activity include Qβ replicase, which has an intrinsic template-independent RNA 3'-adenylation activity; POLQ, which possesses a template independent DNA polymerase activity and allows for extension of single-stranded DNA as well as duplex DNA with either protruding or multiply mismatched 3'-OH termini; Dpo1, which displays a competing terminal deoxynucleotide transferase (TdT) activity unlike any other B-family DNA polymerase; EcPAP (*Escherichia coli* PAP (EcPAP)), which shares a structure with those of other template-independent RNA polymerases suggests and includes changes of domain(s) outside the conserved catalytic core domain that alter substrate specificities of template-independent RNA polymerases; and site-directed mutants of human Polmu (e.g., Arg387 to Lys) that provide enhanced terminal transferase activity. A terminal transferase activity can add deoxyribonucleotides or ribonucleotides to the 3' ends of RNA and DNA. Therefore, throughout this disclosure, when referring to terminal transferase activity, deoxyribonucleotides and ribonucleotides may be substituted for each other. Similarly, dNTP may be substituted for NTP; and NTP may be substituted for dNTP. In like fashion, dATP and ATP; dCTP and CTP; dGTP and GTP; and dTTP and TTP or dUTP; may be substituted for each other.

A mixture can include any combination of two or more different types of nucleotides (e.g., 2, 3 or 4 nucleotides) that can be incorporated onto the 3' end of a nucleic acid. A mixture often includes two or more different deoxynucleotide triphosphates, and the deoxynucleotide triphosphates sometimes are chosen from adenosine triphosphate (ATP), guanosine triphosphate (GTP), cytidine triphosphate (CTP) and thymidine triphosphate (TTP). The nucleic acid sometimes is a first ssNA and/or a second ssNA, as described herein. The nucleic acid sometimes includes a candidate polynucleotide, where the candidate polynucleotide comprises or consists of a region of interest (e.g., one nucleotide of interest, one nucleotide position of interest, a polynucleotide of interest or a polynucleotide position of interest).

In addition to adding a heteropolynucleotide (also referred to as a heteropolymer) molecular index to a nucleic acid, a method sometimes includes adding a homopolynucleotide (also referred to as a homopolymer) to the nucleic acid in proximity to the index. A nucleic acid modified by an added heteropolynucleotide index and optionally an added homopolynucleotide is referred to herein as a "modified nucleic acid." An added homopolynucleotide sometimes is directly linked to a heteropolynucleotide index, and sometimes is separated from the heteropolynucleotide index by about 2 to about 50 consecutive nucleotide bases. An added homopolynucleotide (i) sometimes serves as a flag, which sometimes is utilized as a reference in sequencing applications of the technology; (ii) sometimes serves as a mark, which at times is utilized as a second reference in sequencing applications of the technology; (iii) sometimes serves as a binding site for a second ssNA that can be annealed to the modified nucleic acid, where the 5' end of the second ssNA sometimes is ligated to the 3' end of the modified nucleic acid and/or where the second ssNA can be extended and optionally amplify the modified nucleic acid (e.g., linear amplification or exponential amplification); or (iv) a combination of two or three of (i), (ii) and (iii).

For embodiments in which a homopolynucleotide and a heteropolynucleotide index are added to a nucleic acid by a terminal transferase activity (referred to hereafter interchangeably as a "first element" and a "second element"), (a) the terminal transferase activity sometimes is terminated after the first element is added and terminal transferase activity then can be introduced for adding the second element (e.g., terminal transferase activity sometimes is terminated by temperature elevation or introducing a chemical denaturant); (b) sometimes the terminal transferase activity is not terminated after the first element is added; (c) nucleotides sometimes are inactivated or neutralized (e.g., dephosphorylated) after the first element is added and before the second element is added; (d) nucleotides sometimes are not inactivated or neutralized (e.g., not dephosphorylated) after the first element is added and/or before the second element is added; (e) nucleotides sometimes are separated from the nucleic acid (e.g., by solid phase separation) after the first element is added and new nucleotides are introduced before the second element is added; (f) nucleotides sometimes are not separated from the nucleic acid (e.g., nucleic acid is not separated by solid phase separation) after the first element is added and/or before the second element is added; and (g) where the first element is a homopolynucleotide added before a heteropolynucleotide second element, terminal transferase activity sometimes is not terminated, and a mixture of one or more nucleotides (e.g., mixture of 1, 2, 3 or 4 nucleotide types) is added after the first element is added and before the second element is added.

An added homopolynucleotide generally consists of a plurality of single nucleotide monomers (e.g., polyA, polyG, polyT or polyC). An added homopolynucleotide sometimes is a tandem homopolynucleotide comprising a first homopolynucleotide and a second homopolynucleotide directly linked to or separated from (e.g., by about 2 to about 10 consecutively linked nucleotide bases) the first homopolynucleotide, where the first homopolynucleotide consists of a first nucleotide and the second homopolynucleotide consists of a second nucleotide different than the first nucleotide. A tandem homopolynucleotide sometimes is generated by (i) contacting a nucleic acid with the terminal transferase activity and a first composition comprising single nucleotide monomers under conditions in which the first homopolynucleotide is generated, and (ii) contacting the nucleic acid with the terminal transferase activity and a second composition comprising single nucleotide monomers different than the single nucleotide monomers in the first composition under conditions in which the second homopolynucleotide is generated. The terminal transferase activity sometimes is terminated after part (i) and then added for part (ii), and sometimes the terminal transferase activity is not terminated between (i) and (ii), in the foregoing method. Nucleotides sometimes are inactivated or neutralized (e.g., dephosphorylated) and/or sometimes the nucleic acid is separated from nucleotides (e.g., solid phase separation), after part (i) in the foregoing method.

A heteropolynucleotide index added by a DMI process sometimes is about 3 consecutive nucleotide bases to about 100 consecutive nucleotide bases in length, sometimes is about 5 consecutive nucleotide bases to about 50 consecutive nucleotide bases in length, sometimes is about 5 consecutive nucleotide bases to about 40 consecutive nucleotide bases in length, sometimes is about 5 consecutive nucleotide bases to about 35 consecutive nucleotide bases in length, and sometimes is about 5 consecutive nucleotide bases to about 30 consecutive nucleotide bases in length. A heteropolynucleotide index added by a DMI process sometimes has an average, mean, median, nominal or maximum length of about 5 to about 50, about 5 to about 40, about 5 to about 35, about 5 to about 30, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95 or 100, consecutive nucleotide bases. The length of molecular indexes added by a DMI process (e.g., average, mean, median, minimum or maximum length) can be predetermined by the length of time a mixture of two or more nucleotide types are incubated with terminal transferase activity in certain embodiments. An added homopolynucleotide, if present, sometimes is about 3 consecutive nucleotide bases to about 100 consecutive nucleotide bases in length, sometimes is about 5 consecutive nucleotide bases to about 50 consecutive nucleotide bases in length, sometimes is about 10 consecutive nucleotide bases to about 40 consecutive nucleotide bases in length, and sometimes is about 10 consecutive nucleotide bases to about 35 consecutive nucleotide bases in length. An added homopolynucleotide, if present, sometimes has an average, mean, median, nominal or maximum length of about 5 to about 50, about 10 to about 40, about 10 to about 35, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95 or 100, consecutive nucleotide bases. Each of the first homopolynucleotide and the second homopolynucleotide, independently, in an added tandem homopolynucleotide, if present, sometimes is about 3 consecutive nucleotide bases to about 50 consecutive nucleotide bases in length, sometimes is about 5 consecutive nucleotide bases to about 40 consecutive nucleotide bases in length, and sometimes is about 10 consecutive nucleotide bases to about 35 consecutive nucleotide bases in length. Each of the first homopolynucleotide and the second homopolynucleotide independently, in an added tandem homopolynucleotide, if present, sometimes has an average, mean, median, nominal or maximum length of about 5 to about 50, about 5 to about 40, about 10 to about 35, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45 or 50, consecutive nucleotide bases.

The length of a heteropolynucleotide index and/or homopolynucleotide (e.g., tandem homopolynucleotide) added to nucleic acid by terminal transferase activity in a DMI process (e.g., average, median, mean, nominal, minimum or maximum length) can be determined in part by the period of time under which the nucleic acid is contacted with terminal transferase activity prior to inactivating the terminal transferase activity. Different periods of time can be utilized, prior to inactivating the terminal transferase activity, to modulate the length of the heteropolynucleotide index or homopolynucleotide added to a nucleic acid by a DMI process. In some embodiments, a predetermined period of time suitable for providing a particular length (e.g., a particular average, mean, median, nominal, minimum or maximum length) may be ascertained after testing different periods of time. In embodiments for which a heteropolynucleotide index and a homopolynucleotide are added to a nucleic acid by terminal transferase activity, the heteropolynucleotide index independently may be added for a first period of time and the homopolynucleotide independently may be added for a second period of time, where the first period of time may be the same or different than the second period of time. In embodiments for which a heteropolynucleotide index and a homopolynucleoitde are added to a nucleic acid by terminal transferase activity, terminal transferase activity sometimes is inactivated, and sometimes is not activated between the heteropolynucleotide index addition and the homopolynucleotide addition. In certain embodiments, a period of time is about 1 minute to about 120 minutes, about 2 minutes to about 90 minutes, about 3 minutes to about 60 minutes, about 5 minutes to about 30 minutes, about 10 minutes to about 30 minutes, about 15 minutes to about 25 minutes, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 minutes, prior to inactivating the terminal transferase activity. Terminal transferase activity can be inactivated by any suitable process, including without limitation, heat inactivation (e.g., elevating to a temperature that inactivates terminal transferase enzyme), chemical inactivation (e.g., adding a protein denaturant that denatures terminal transferase enzyme), inactivating nucleotide(s) not added by terminal transferase activity, and sequestering a co-factor for terminal transferase activity.

In certain embodiments, a method includes: (a) prior to contacting the nucleic acid with the mixture of two or more different nucleotides, contacting the nucleic acid with a terminal transferase activity and a composition comprising single nucleotide monomers under conditions in which the monomers are added to the 3' terminus of the nucleic acid by the terminal transferase activity, thereby adding a flag homopolynucleotide comprising the monomers to the 3' end of the nucleic acid and generating a flagged nucleic acid; and (b) contacting the flagged nucleic acid with a terminal transferase activity and the mixture of two or more different nucleotides under conditions in which nucleotides in the mixture are sequentially and randomly added to the 3' terminus of the flagged nucleic acid by the terminal transferase activity, thereby adding an index heteropolynucleotide comprising nucleotides in the mixture to the 3' end of the flagged nucleic acid and generating an indexed nucleic acid comprising, 5' to 3', the flag homopolynucleotide and the index heteropolynucleotide. In some embodiments, a method includes: (a) prior to contacting the nucleic acid with the mixture of two or more different nucleotides, contacting the nucleic acid with a terminal transferase activity and a composition comprising single nucleotide monomers under conditions in which the monomers are added to the 3' terminus of the nucleic acid by the terminal transferase activity, thereby adding a homopolynucleotide comprising the monomers to the 3' end of the nucleic acid and generating a first modified nucleic acid; and (b) contacting the first modified nucleic acid with a terminal transferase activity and the mixture of two or more different nucleotides under conditions in which nucleotides in the mixture are sequentially and randomly added to the 3' terminus of the first modified nucleic acid by the terminal transferase activity, thereby adding a heteropolynucleotide comprising nucleotides in the mixture to the 3' end of the first modified nucleic acid and generating a second modified nucleic acid comprising, 5' to 3', the homopolynucleotide and the heteropolynucleotide.

In some embodiments, a method includes: (a) prior to contacting the nucleic acid with the mixture of two or more different nucleotides, contacting the nucleic acid with a terminal transferase activity and a first composition comprising single nucleotide monomers under conditions in which the monomers are added to the 3' terminus of the nucleic acid by the terminal transferase activity, thereby adding a mark homopolynucleotide comprising the monomers to the 3' end of the nucleic acid and generating a marked nucleic acid; (b) contacting the marked nucleic acid with a terminal transferase activity and the mixture of two or more different nucleotides under conditions in which nucleotides in the mixture are sequentially and randomly added to the 3' terminus of the flagged nucleic acid by the terminal transferase activity, thereby adding an index heteropolynucleotide comprising nucleotides in the mixture to the 3' end of the marked nucleic acid and generating an indexed nucleic acid comprising, 5' to 3', the mark homopolynucleotide and the index heteropolynucleotide; and (c) contacting the indexed nucleic acid with a terminal transferase activity and a second composition comprising single nucleotide monomers different than the single nucleotide monomers in the first composition under conditions in which the monomers in the second composition are added to the 3' terminus of the indexed nucleic acid by the terminal transferase activity, thereby adding a flag homopolynucleotide comprising the monomers in the second composition to the 3' end of the indexed nucleic acid and generating a modified nucleic acid comprising, 5' to 3', the mark homopolynucleotide, the index heteropolynucleotide and the flag homopolynucleotide.

In certain embodiments, a method includes: (a) prior to contacting the nucleic acid with the mixture of two or more different nucleotides, contacting the nucleic acid with a terminal transferase activity and a first composition comprising single nucleotide monomers under conditions in which the monomers are added to the 3' terminus of the nucleic acid by the terminal transferase activity, thereby adding a first homopolynucleotide comprising the monomers to the 3' end of the nucleic acid and generating a first modified nucleic acid; (b) contacting the first modified nucleic acid with a terminal transferase activity and the mixture of two or more different nucleotides under conditions in which nucleotides in the mixture are sequentially and randomly added to the 3' terminus of the first modified nucleic acid by the terminal transferase activity, thereby adding a heteropolynucleotide comprising nucleotides in the mixture to the 3' end of the first modified nucleic acid and generating a second modified nucleic acid comprising, 5' to 3', the first homopolynucleotide and the heteropolynucleotide; and (c) contacting the second modified nucleic acid with a terminal transferase activity and a second composition comprising single nucleotide monomers different than the single nucleotide monomers in the first composition under conditions in which the monomers in the second composition are added to the 3' terminus of the second modified nucleic acid by the terminal transferase activity, thereby adding a second homopolynucleotide comprising the monomers in the second composition to the 3' end of the second modified nucleic acid and generating a third modified nucleic acid comprising, 5' to 3', the first homopolynucleotide, the heteropolynucleotide and the second homopolynucleotide.

In certain embodiments, a method includes contacting the indexed nucleic acid (or modified nucleic acid) with a terminal transferase activity and a composition comprising single nucleotide monomers under conditions in which the monomers are added to the 3' terminus of the indexed nucleic acid (or modified nucleic acid) by the terminal transferase activity, thereby adding a flag homopolynucleotide comprising the monomers to the 3' end of the indexed nucleic acid (or modified nucleic acid) and generating a flagged nucleic acid comprising, 5' to 3', the index heteropolynucleotide and the flag homopolynucleotide. In some embodiments, a method includes: contacting the indexed nucleic acid (or modified nucleic acid) with a terminal transferase activity and a composition comprising single nucleotide monomers under conditions in which the monomers are added to the 3' terminus of the indexed nucleic acid (or modified nucleic acid) by the terminal transferase activity, thereby adding a homopolynucleotide comprising the monomers to the 3' end of the indexed nucleic acid (or modified nucleic acid) and generating an additionally modified nucleic acid comprising, 5' to 3', the heteropolynucleotide and the homopolynucleotide.

A second ssNA sometimes includes a binding polynucleotide complementary to a target polynucleotide in a first ssNA to which a heteropolynucleotide index has been added. The first ssNA sometimes includes a native target polynucleotide to which a complementary binding polynucleotide can anneal. The first ssNA sometimes includes a non-native homopolynucleotide that has been added and serves as a target polynucleotide to which a complementary binding polynucleotide in the second ssNA can anneal.

A second ssNA sometimes is annealed to a first ssNA containing a heteropolynucleotide index. In some embodiments, one or more of the following is performed after a first ssNA is annealed to a second ssNA: (i) ligation of the second ssNA and the first ssNA by a ligase, (ii) extension of the second ssNA under extension conditions; (iii) circularization of nucleic acid by a ligase, (iv) nucleic acid cleavage of a nucleic acid by a cleaving agent, and (v) amplification of nucleic acid (e.g., linear amplification or exponential amplification). Combinations of two or three or four or five of (i), (ii), (iii), (iv) and (v) in the previous sentence can be performed in any suitable order. In certain embodiments, one or more of the following is not performed: (i) ligation of the second ssNA and the first ssNA by a ligase, (ii) circularization of nucleic acid by a ligase, and (iii) nucleic acid cleavage of a nucleic acid by a cleaving agent.

For embodiments in which a heteropolynucleotide index is added to a nucleic acid, and a second ssNA is annealed to a first ssNA comprising the heteropolynucleotide index, the second ssNA sometimes is extended under extension conditions. As used herein, "extension conditions" permit template-dependent addition of one nucleotide base or two or more consecutive nucleotide bases to a nucleic acid in a complex that often is partially double-stranded and partially single-stranded. Extension conditions often include a polymerase, a mixture of nucleotide triphosphate bases, and optionally include other elements such as buffer, salt and/or co-factors, for example, as known in the art. Extension conditions sometimes are isothermal, and sometimes include thermocycles, as known in the art.

Nucleic acid optionally is amplified under amplification conditions in certain methods. The second ssNA sometimes includes at least one priming tag polynucleotide that is complementary to, or substantially complementary to, a primer oligonucleotide or portion thereof. The second ssNA sometimes includes at least one priming tag polynucleotide configured such that its complement is complementary to, or substantially complementary to, a primer oligonucleotide or portion thereof. A priming tag can be useful for amplifying nucleic acid under amplification conditions, as described herein. Amplification conditions often are similar to extension conditions, often include one or more amplification primers, often permit isothermal or thermocycled amplification, sometimes permit linear amplification and sometimes permit exponential amplification as known in the art.

In some embodiments, a method includes extension of a second ssNA annealed to a first ssNA, and one or more of the following is performed after extension: (i) ligation of the second ssNA and the first ssNA by a ligase, (ii) circularization of nucleic acid by a ligase, (iii) nucleic acid cleavage of a nucleic acid by a cleaving agent, and (iv) amplification of nucleic acid under amplification conditions. Combinations of two, three or four of (i), (ii), (iii) and (iv) in the previous sentence can be performed in any suitable order. In certain embodiments, one or more of the following is not performed: (i) ligation of the second ssNA and the first ssNA by a ligase, (ii) circularization of nucleic acid by a ligase, and (iii) nucleic acid cleavage of a nucleic acid by a cleaving agent.

In certain embodiments, a method includes: (a) contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid; (b) contacting the first modified nucleic acid with a terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid comprising, 5' to 3', the heteropolynucleotide and the homopolynucleotide; and (c) contacting the second modified nucleic acid with a second single-stranded nucleic acid comprising a binding polynucleotide complementary to, or substantially complementary to, the homopolynucleotide of the second modified nucleic acid under extension conditions, and optionally under amplification conditions.

In some embodiments, a method includes: (a) contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid; (b) contacting the first modified nucleic acid with a terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid comprising, 5' to 3', the heteropolynucleotide and the homopolynucleotide; and (c) contacting the second modified nucleic acid with a second single-stranded nucleic acid comprising a binding polynucleotide complementary to, or substantially complementary to, the homopolynucleotide in the second modified nucleic acid and a ligase activity under conditions in which the 3' end of the second modified nucleic acid and the 5' end of the second single-stranded nucleic acid ligate, thereby generating a ligated nucleic acid.

In certain embodiments, a method includes: (a) contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid; (b) contacting the first modified nucleic acid with a terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid comprising, 5' to 3', the heteropolynucleotide and the homopolynucleotide; (c) contacting the second modified nucleic acid with nucleotides, a polymerase and a second single-stranded nucleic acid comprising a binding polynucleotide complementary to, or substantially complementary to, the homopolynucleotide in the second modified nucleic acid under linear amplification conditions, thereby generating first amplicons; and (d) contacting the first amplicons with a ligase activity under conditions in which the 3' end and 5' end of the first amplicons are ligated and circularized first amplicons are generated.

In certain embodiments, linear nucleic acid can be generated from nucleic acid in a hairpin or circularized form. Nucleic acid in hairpin form and circularized form can be generated by contacting nucleic acid with a ligase activity, as known and illustrated herein. Linear nucleic acid sometimes is generated from nucleic acid in hairpin or circularized form by cleaving the hairpin or circularized nucleic acid. Cleaving sometimes is performed by an agent having endonuclease activity, and the nucleic acid can be cleaved by such an agent at a site comprising a cleavable nucleotide base (e.g., deoxyinosine) or a site comprising, or is near to, a restriction endonuclease recognition site, for example. A cleaving agent often is an endonuclease enzyme (e.g., Endonuclease V). In certain embodiments, a cleavable site is present in a second ssNA, and located 5' of a binding polynucleotide complementary to a polynucleotide in the first ssNA (e.g., a candidate polynucleotide (e.g., a native candidate polynucleotide) or an added homopolynucleotide). In some embodiments, a cleavable site is present in a second ssNA and located 5' of a binding polynucleotide and 3' of a tag polynucleotide (i.e., between the binding polynucleotide and tag polynucleotide). A cleavable site sometimes is provided by a second ssNA, sometimes the second ssNA includes a first priming tag polynucleotide and a second priming tag polynucleotide, and the cleavable site sometimes is located between the first priming tag polynucleotide and the second priming tag polynucleotide.

In some embodiments, linear nucleic acid is generated from nucleic acid in hairpin or circularized form by extension and optional amplification. Certain methods include annealing a primer comprising a polynucleotide complementary to a tag polynucleotide in the nucleic acid (e.g., often contributed by a second ssNA), extending the primer and optionally amplifying nucleic acid under amplification conditions, where the nucleic acid includes a region that the polymerase performing the extension/amplification does not read through. Such a region is referred to herein as a spacer region, which cannot be traversed by a polymerase. A spacer region sometimes is provided by a second ssNA, sometimes the second ssNA includes a first priming tag polynucleotide and a second priming tag polynucleotide, and the spacer sometimes is located between the first priming tag polynucleotide and the second priming tag polynucleotide.

In certain embodiments, linearized nucleic acid is amplified (e.g., linear amplification or exponential amplification). Linearized nucleic acid, which optionally is amplified, sometimes is analyzed by a sequencing process.

In certain embodiments, nucleic acid that is to be modified by added heteropolynucleotides is provided as a plurality of nucleic acid molecules, one of the heteropolynucleotides is added to each of the nucleic acid molecules, and there is a possibility of (i) about $4^3$ to about $4^{50}$ different heteropolynucleotides generated by the terminal transferase/nucleotide mixture reaction conditions, (ii) about $4^4$ to about $4^{40}$ different heteropolynucleotides generated by the terminal transferase/nucleotide mixture reaction conditions, (iii) about $4^4$ to about $4^{35}$ different heteropolynucleotides generated by the terminal transferase/nucleotide mixture reaction conditions, or (iv) about $4^5$ to about $4^{30}$ different heteropolynucleotides generated by the terminal transferase/nucleotide mixture reaction conditions, where the mixture includes four nucleotide types. In some embodiments, there is a possibility of (i) about $2^3$ to about $2^{50}$ different heteropolynucleotides generated by the terminal transferase/nucleotide mixture reaction conditions, (ii) about $2^4$ to about $2^{40}$ different heteropolynucleotides generated by the terminal transferase/nucleotide mixture reaction conditions, (iii) about $2^4$ to about $2^{35}$ different heteropolynucleotides generated by the terminal transferase/nucleotide mixture reaction conditions, or (iv) about $2^5$ to about $2^{30}$ different heteropolynucleotides generated by the terminal transferase/nucleotide mixture reaction conditions, where the mixture includes two nucleotide types. In certain embodiments, there is a possibility of (i) about $3^3$ to about $3^{50}$ different heteropolynucleotides generated by the terminal transferase/nucleotide mixture reaction conditions, (ii) about $3^4$ to about $3^{40}$ different heteropolynucleotides generated by the terminal transferase/nucleotide mixture reaction conditions, (iii) about $3^4$ to about $3^{35}$ different heteropolynucleotides generated by the terminal transferase/nucleotide mixture reaction conditions, or (iv) about $3^5$ to about $3^{30}$ different heteropolynucleotides generated by the terminal transferase/nucleotide mixture reaction conditions, where the mixture includes three nucleotide types.

According to an average, mean or median length x of a heteropolynucleotide index added by a DMI process in certain embodiments there is a possibility of (i) about $4^x$ different heteropolynucleotides generated when a mixture of four different nucleotide types (i.e., four different nucleotide bases) is contacted with a terminal transferase activity in the DMI process; (ii) about $3^x$ different heteropolynucleotides generated when a mixture of three different nucleotide types (i.e., three different nucleotide bases) is contacted with a terminal transferase activity in the DMI process; or (iii) about $2^x$ different heteropolynucleotides generated when a mixture of two different nucleotide types (i.e., two different nucleotide bases) is contacted with a terminal transferase activity in the DMI process. An average, mean or median length x of a heteropolynucleotide index added by a DMI process sometimes is about 5 to about 100, about 5 to about 50, about 5 to about 40, about 5 to about 35, about 5 to about 30, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95 or 100, consecutive nucleotide bases.

Figure 28:
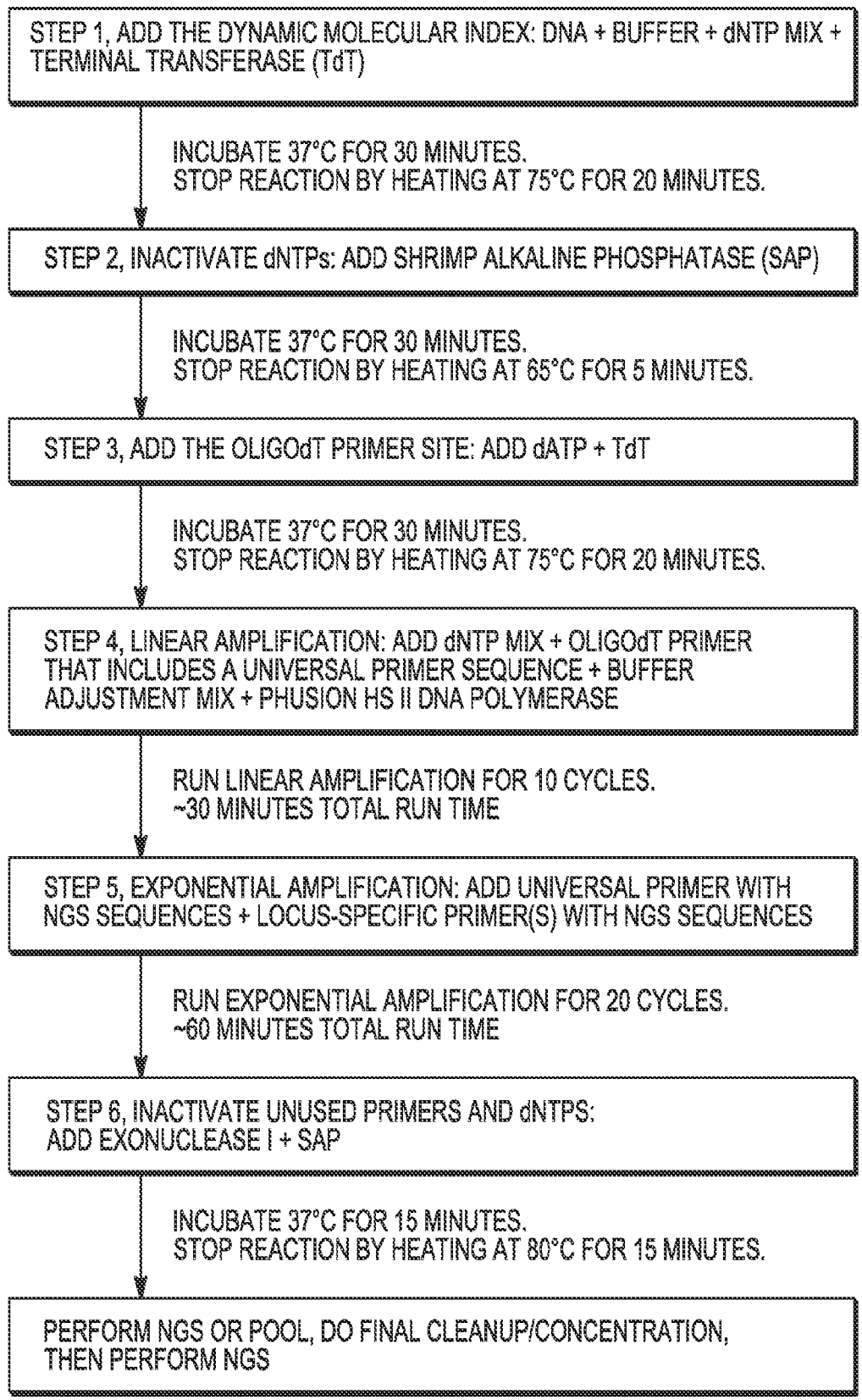
FIG. 28 shows an example of a dynamic molecular indexing (DMI) process embodiment.

Certain non-limiting examples of DMI processes, and resulting indexed, flagged and/or marked nucleic acid are described in Example 6 and illustrated in FIGS. 16 to 25 and in FIG. 28. As illustrated in FIG. 28, certain DMI processes include: (a) contacting a nucleic acid with terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid (i.e., an indexed nucleic acid); (b) inactivating the terminal transferase activity and the nucleotides in the mixture after (a) after a first predetermined period of time; (c) contacting the first modified nucleic acid with terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid; (d) inactivate the terminal transferase activity after (c) after a second predetermined period of time; (e) contacting the second modified nucleic acid with a first primer oligonucleotide that can anneal to the homopolynucleotide and comprises at its 5' end a first sequence, a mixture of nucleotides and a polymerase under linear amplification conditions, thereby amplifying the second modified nucleic acid and generating first amplicons that comprise complements of the heteropolynucleotide (i.e., dynamic molecular indexes) and original, native sequences; (f) contacting the first amplicons with a second primer oligonucleotide comprising a second sequence that anneals in a sequence-specific manner (e.g., locus specific) to the first amplicons, a third primer oligonucleotide comprising on its 3' end the first sequence, a mixture of nucleotides and a polymerase under exponential amplification conditions, thereby generating second amplicons (e.g., locus-specific second amplicons); (g) inactivating or removing the nucleotides that are unused and primer oligonucleotides that are unused after (f); and (h) determining sequences of the second amplicons. Second amplicons from different reactions optionally can be pooled after (g) and prior to (h). In certain embodiments, (a) through (g) are performed in a single container (e.g., a single reaction environment; a single tube). The second primer oligonucleotide in some embodiments can anneal to a polynucleotide locus in a subset of the first amplicons (e.g., the second primer is a locus-specific primer), and in some embodiments two or more second primer species (i.e., each species having different sequences) in a collection that anneal to different polynucleotide loci are utilized in one process (e.g., in a multiplexing process). Sometimes the polynucleotide locus is part of or adjacent to a region of interest that will be analyzed by sequencing (e.g., the locus is a sequence variation, mutation, polymorphism). The second primer in some embodiments includes one or more polynucleotides that facilitate sequencing. The third primer oligonucleotide in some embodiments can anneal to the complement of all first amplicons and sometimes is considered a universal primer. A universal primer often comprises the first sequence or consists of the first sequence. The third primer oligonucleotide in some embodiments includes one or more polynucleotides that facilitate sequencing. Sequencing in (h) sometimes is performed by a highly multiplexed sequencing (HMS) process or NGS process.

DMI processes described herein provide several advantages for indexing, identifying and quantifying nucleic acid. One advantage is that DMI processes generate a high degree of molecular index diversity. Without being limited by theory, this high degree of molecular index diversity is due in part to (i) random incorporation of nucleotide bases from a base mixture by terminal transferase activity, and (ii) different index lengths added to nucleic acid by terminal transferase activity in a given period of time. Since with DMI processes each original, native molecule serves as a substrate for the synthesis of the molecular index, each dynamic molecular index is unique. In practice, there often are 10 to 70 or more nucleotides randomly added to any particular original, native molecule, yielding a diversity range of $4^{10}$ ($>10^6$) to $4^{70}$ ($>10^{42}$) or more DMIs, with an average diversity of $\sim 4^{40}$ ($>10^{24}$) which far outstrips the diversity of molecular indexes of other methods and is even slightly more than the number of nucleotides in the human body.

Direct tagging of sample nucleic acid, and the high degree of molecular index diversity, are features that make DMI processes advantageous for detecting and quantifying relatively rare alleles in a nucleic acid sample. Massively parallel sequencing or "NexGen Sequencing" (NGS) processes often are utilized to analyze samples. In NGS processes, however, it often is not possible to tell which molecules are original, native molecules, and which are copies since some amplification occurs prior to spatial separation of molecules. Also, the accuracy of NGS is ~99.7%, which means an error rate of ~0.3% or 1 mistake in sequence for every 333 bases sequenced. These two issues with NGS processes combined can make the detection of rare sequences, e.g. the detection of cancer gene mutations against a high background of wild type sequences, problematic and thus their precise quantification unreliable. In commercial practice, the limit of detection of mutation or minor allele frequency generally is no better than 2% to 3%. DMI processes address these issues by directly tagging each native molecule with a unique label prior to it being copied. Terminal transferase activity utilized in DMI processes adds DMIs directly to nucleic acid to be analyzed, and the high degree of tag diversity enhances the probability that a unique tag is added to the nucleic acid to be analyzed.

Another advantage afforded by the high molecular index diversity provided by DMI processes is identification of sample contamination. Even in high-throughput environments one would not expect to see the same DMIs in two samples. Such an event can be cause to look for sample-to-sample contamination. With much lower diversity seen with other methods, the same molecular index would be expected in multiple samples on a routine basis.

Other advantages are that DMI process embodiments do not make use of pre-synthesized oligonucleotide index tags (PSOTs). Dynamic molecular indexes (DMIs) added by DMI processes are not pre-synthesized because terminal transferase activity adds nucleotide bases one at a time directly to nucleic acid to be analyzed and thereby sequentially builds diverse DMIs in situ. Obviating use of PSOTs provides for several advantages. Since DMIs are not pre-synthesized, there are no oligonucleotides to make, no quality assurance or quality control issues regarding them, no lot-to-lot variation, inventories, or associated expenses. PSOTs are created on a solid support, resulting in many identical copies, and even as little as one picomole of a particular PSOT consists of $6.022 \times 10^{11}$ molecules, creating a virtually non-depleting pool. Processes that utilize PSOTs typically provide significantly less tag diversity than DMI processes. For example, certain PSOT processes provide an average diversity of only $10^6$, or less than $10^4$, as compared to an average diversity of $10^{24}$ afforded by DMI processes.

PSOTs often are attached to nucleic acid by ligation of adaptors or by primer extension, and DMI processes provide advantages over each of these methodologies. One commercially available method using PSOTs ("Method A") uses a molecular barcode that consists of a 10 nucleotide degenerate base region (DBR). Although the DBR theoretically produces a diversity of about $10^6$ combinations, it requires target-specific double-stranded adaptors with accompanying expense. The use of pre-synthesized oligonucleotides also means that there are no truly unique molecular indexes: as described above, even as little as one picomole of a particular molecular index applied to a sample consists of $6.022 \times 10^{11}$ molecules, creating a virtually non-depleting pool. Both methods also require that unused adapters be removed plus a number of buffer changes and tube transfers, all adding to expense, loss of material, and increasing the time and labor needed. Another commercially available method using PSOTs ("Method B") makes use of a defined set of 96 double-stranded adapters, each with a single dT nucleotide 3' overhang to facilitate the ligation, which can be inefficient. This requires not only the aforementioned well-controlled synthesis of oligonucleotides (192 of them), but also their pairwise annealing to form the 96 adapters. This limited number of adapters can create a maximum diversity of only 9,216 combinations, thus samples that contain more than that number of molecules cannot be accurately counted. Accordingly, DMI processes provide for a higher degree of tag diversity over PSOT methods, and there also are no problems with inefficient ligation or any unused adapters to remove prior to sequencing (e.g., NGS).

Rather than using adapters, PSOTs can be attached by primer extension, for instance, during PCR or in the case of RNA, during cDNA synthesis. In these instances, copies of the nucleic acid molecules are created during the addition of molecular indexes, and the original, native molecules are never actually labeled. For example, if first strand cDNAs are made using a molecularly indexed primer, the original RNA template is never molecularly indexed, and only the first strand cDNA is indexed. The same is the case if a molecular index is added by template switching or during the gene-specific creation of a second strand cDNA. If errors are made during these steps, they will be propagated throughout the analysis. If the cDNA analysis is directed at detecting rare changes in coding sequence (e.g. mutation detection) such non-DMI approaches can compromise results. In methods where polyA+ RNA is the starting material, polyA− RNA, including miRNA and most RNA fragments will not be included. Thus an advantage of DMI processes is that, in contrast to processes that affix PSOTs by primer extension (e.g. during first or second strand cDNA synthesis or targeted PCR), the DMI is always added to the original, native molecule, not to a mere copy, thus eliminating a source of error.

Another advantage of DMI processes is that they can be flexibly utilized on a wide variety of nucleic acid samples. DMI processes can be performed under identical conditions to add molecular indexes to single-stranded DNA, double-stranded DNA, single-stranded RNA, or double-stranded RNA or any mixture of nucleic acid molecules. Either ribonucleotides or deoxyribonucleotides can be used to create DMIs. The substrate can have a recessed, protruding, or blunt 3' end, and be of any length.

Another advantage is that certain DMI process embodiments can be performed in a single container (e.g., single reaction vessel, single tube). Other advantages is that DMI processes reduce the number of user manipulations compared to certain processes that utilize PSOTs. DMI processes also provide advantages of reducing incubation time, reducing cost per sample, and being suitable for analyzing cell free nucleic acid or circulating cell free nucleic acid (e.g., cell free DNA (cfDNA; e.g., from blood, urine or saliva)) compared to certain PSOT-based methods.

Certain advantages of a DMI process embodiment illustrated in FIG. 28 and described in Example 6 over certain PSOT methods are summarized in the following table.

|  | DMI | PSOT Method A | PSOT Method B |
|---|---|---|---|
| Average Diversity | $10^{24}$ | $10^6$ | less than $10^4$ |
| Adapters | No | Yes | Yes |
| Single tube | Yes | No | No |
| Manipulations | 6 | 56 | 44 |
| (add/remove/transfer) | (6/0/0) | (34/8/14) | (24/15/5) |
| Incubations (approximate) | 4 hrs | 4.5 hrs to 18.5 hrs | 6 hrs |
| Suitable for cfNA | +++ | No | + |
| Cost/sample (estimated) | lower | higher | higher |

Kits

The disclosure includes kits for the performance of all or part of the disclosed methods and/or for the production of the disclosed products. Kits often comprise one or more containers that contain one or more components described herein. A kit can include one or more components in any number of separate containers, packets, tubes, vials, multi-well plates and the like, or components may be combined in various combinations in such containers.

In some embodiments, one or more of the following components may be included in a kit: (i) a molecule that can provide a terminal transferase activity (e.g., an enzyme); (ii) a mixture comprising two or more different nucleotides (e.g., different deoxynucleotide triphosphates; two or more of dATP, dGTP, dCTP and dTTP); (iii) a salt; (iv) a buffer; (v) a terminal transferase enzyme co-factor (e.g., cobalt, manganese, magnesium); (vi) a composition comprising single nucleotide monomers (e.g., one type of deoxynucleotide triphosphate; one of dATP, dGTP, dCTP or dTTP); (vii) a second ssNA described herein (e.g., a second ssNA comprising a binding polynucleotide and at least one priming tag polynucleotide); (viii) a polymerase and other components suitable for nucleic acid extension (e.g., deoxynucleotide mixture); (ix) a polymerase and other components suitable for nucleic acid amplification (e.g., deoxynucleotide mixture and primer(s)); (x) an endonuclease and other components suitable for cleaving a nucleic acid (e.g., Endonuclease V); and (xi) single-stranded nucleic acid ligase and other components for ligating single-stranded nucleic acid ends.

In certain embodiments, one or more of the following components may be included in a kit: (i) a single-stranded oligonucleotide comprising a 5'-phosphate moiety (optionally adenylated), a 5' leader sequence, a target binding sequence that is complementary to at least a portion of a target sequence in a first ssNA, and a 3' end, as described herein; (ii) a single-stranded ligase enzyme (e.g., T4 RNA Ligase 1; or a thermostable enzyme; a single stranded ligase from *M. thermoautotrophicum*); (iii) a polymerase and other components suitable for nucleic acid extension (e.g., deoxynucleotide mixture); (iv) a polymerase and other components suitable for nucleic acid amplification (e.g., deoxynucleotide mixture and primer(s)); and (x) an endonuclease and other components suitable for cleaving a nucleic acid (e.g., Endonuclease V).

A kit sometimes is utilized in conjunction with, or to carry out, a method described herein, and can include instructions or descriptions for performing one or more methods and/or a description of one or more compositions described herein. A kit may include a description of an internet location that provides such instructions and/or descriptions (e.g., a URL for the World-Wide Web). Instructions and/or descriptions may be in tangible form (e.g., paper and the like) or electronic form (e.g., computer readable file on a tangle medium (e.g., compact disc) and the like) and/or may be included in a kit insert, in some embodiments.

A kit can include a conversion table, lookup table, software, executable instructions, and/or an internet location that provides the foregoing, in certain embodiments. A conversion table, lookup table, software and/or executable instructions can be utilized to determine reaction set up, manipulate and/or interpret data resulting from single ssNA molecules and/or digested ssNA molecules described herein.

Having now generally provided the disclosure, the same will be more readily understood through reference to the following examples which are provided by way of illustration, and are not intended to be limiting of the disclosure, unless specified.

EXAMPLES

Example 1: Ligation of a Second ssNA to a Target Sequence

Figure 9:
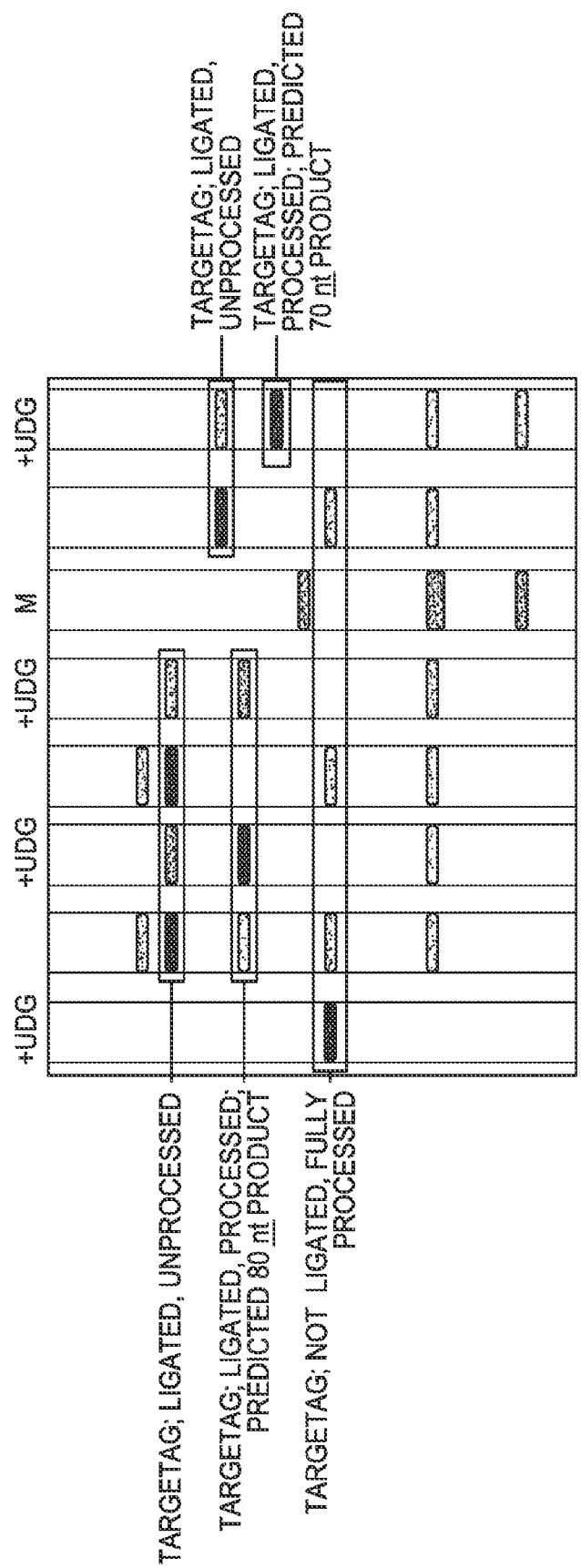
FIG. 9 illustrates ligation was successful after a second ssNA was hybridized and annealed to a target binding sequence in a first ssNA. The product may be processed to a shorter form by UDG digestion that removes the Target binding moiety from the ligated product.

A second ssNA with a target binding sequence against a synthetic human BRAF target sequence was tested for its ability to correctly ligate to its target. FIG. 9 illustrates correct ligation followed by UDG digestion of the ligated molecule to a predicted 80 nucleotide (nt) length.

The second ssNA is identified as "TargeTag" and processing with UDG is indicated across the top. Lane 1 is TargeTag alone while molecular weight markers are identified by the "M" in lane 6. Lanes 2-3 and 4-5 are duplicates using a synthetic target with a predicted 80 nt ligated product. Lanes 7-8 used a synthetic target with a predicted 70 nt ligated product. To be clear, Lane 4 is a duplicate of Lane 2; these lanes show the ligated products prior to treatment with UDG. Lane 5 is a duplicate of Lane 3; these lanes show the ligated products after treatment with UDG resulting in predicted 80 nt products. Lane 7 shows a ligated product prior to treatment with UDG and Lane 8 shows a product after processing with UDG with a predicted 70 nt product in this case.

Figure 10:
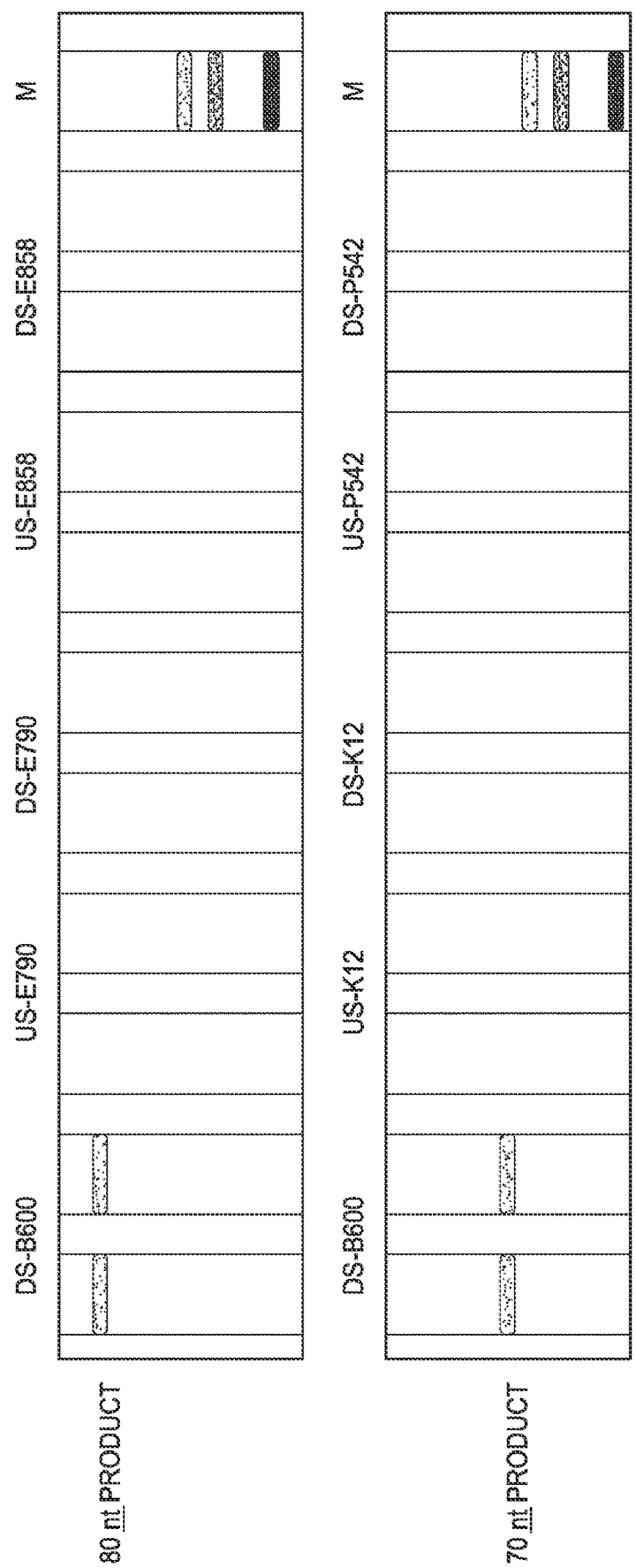
FIG. 10 shows a second ssNA was successfully (i) hybridized and annealed, (ii) ligated and (iii) processed (UDG processing), for two BRAF target binding sequences each in a separate first ssNA embodiment.

Example 2: Second ssNA Molecules are Specific for Their Corresponding Target Sequences In FIG. 10, a second ssNA molecule with a BRAF target binding site was tested using a BRAF (DS-B600) target versus four different EGFR (US-E790, DS-E790 US-E858 and DS-E858) targets; two different KRAS (US-K12 and DS-K12) targets; and two different PIK3CA (US-P542 and DS-P542) targets. Ligation and processing (UDG) of the second ssNA molecule to the two BRAF targets gives the predicted 80 nt or 70 nt products as shown in the upper and lower portions of FIG. 10, respectively. None of the other targets produce ligated products with the BRAF specific ssNA molecule. Reactions were run in duplicate. US designates a target upstream of the designated codon number; DS designates downstream target. Molecular weight markers is indicated by "M."

Figure 11:
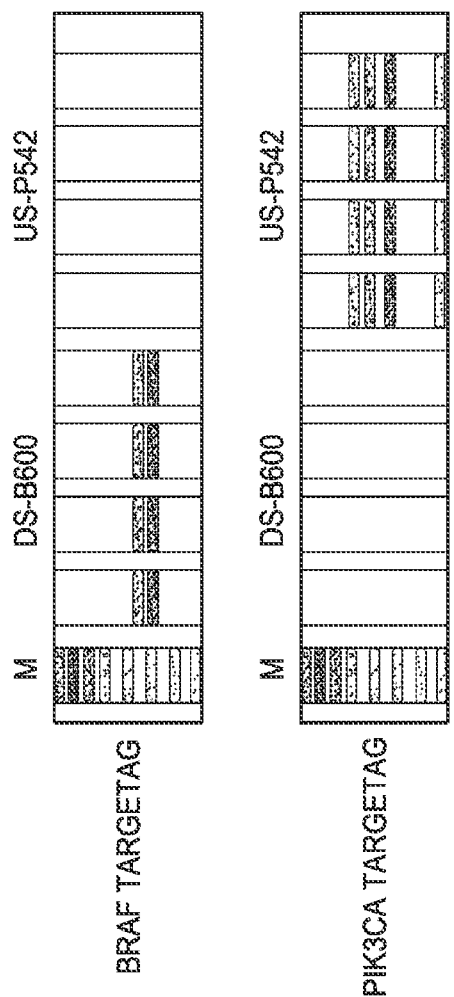
FIG. 11 shows these second ssNA specifically hybridized or annealed and ligated to their BRAF Target sequence in the first ssNA (upper figure) or specifically annealed and ligated to their PIK3CA Target sequence (lower figure).

In an additional test, ssNA molecules with target binding sequences specific for BRAF or PIK3CA were tested. Each ssNA only ligated to its cognate target as shown in FIG. 11.

Example 3: Multiplex Use of ssNA Molecules

Figure 12:
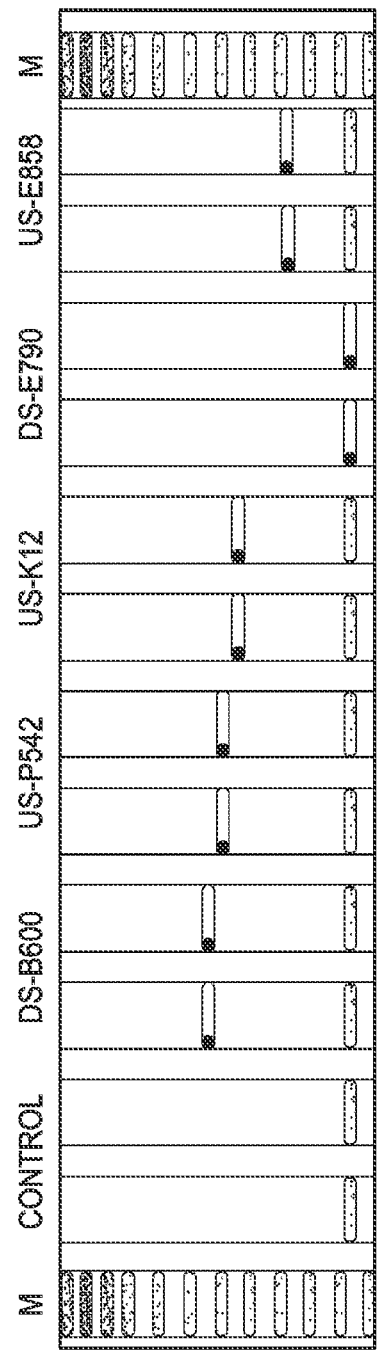
FIG. 12 shows multiple second ssNA embodiments were successfully (i) hybridized and annealed, (ii) ligated and (iii) processed (UDG processing), for multiple first ssNA embodiments in a multiplex assay embodiment.

A reaction containing five (5) ssNA molecules with target binding sequences specific for a BRAF target sequence (DS-B600), a PIK3CA target sequence (US-P542), a KRAS target sequence (US-K12), and two different EGFR target sequences (DS-R790 and US-E858) was tested against one of the five target sequences. The results are shown in FIG. 12.

Each of the five correctly ligated products was produced for each target. The dots indicate products of the predicted sizes when fully processed by UDG. Duplicate reactions are shown. Control is no added target, and M is molecular weight markers.

Example 4: Ligation is Temperature Stable

Figure 13:
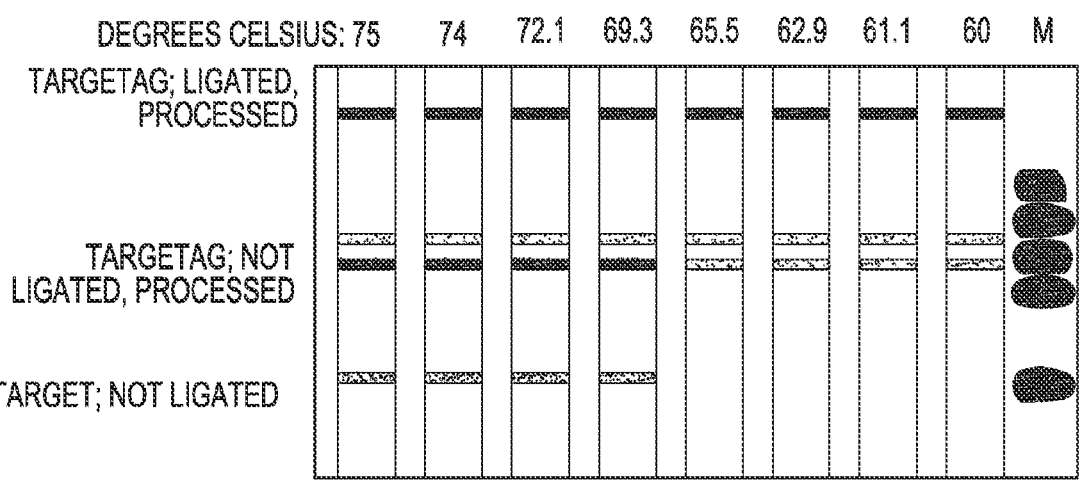
FIG. 13 shows a second ssNA molecule with a specific target binding sequence can be ligated to its first ssNA target across a temperature range from at least 60 to 75 degrees Celsius.

A test of temperature conditions demonstrates that the ssNA molecule with BRAF specific target binding sequence can be ligated to its ssNA target across a temperature range from at least 60 to 75 degrees Celsius. This permits a range of melting temperatures for the selection of target binding sequences in an ssNA molecule for hybridization to a target sequence, as shown in FIG. 13.

Example 5: Specific Amplification of Ligated Molecules

Figure 14A:
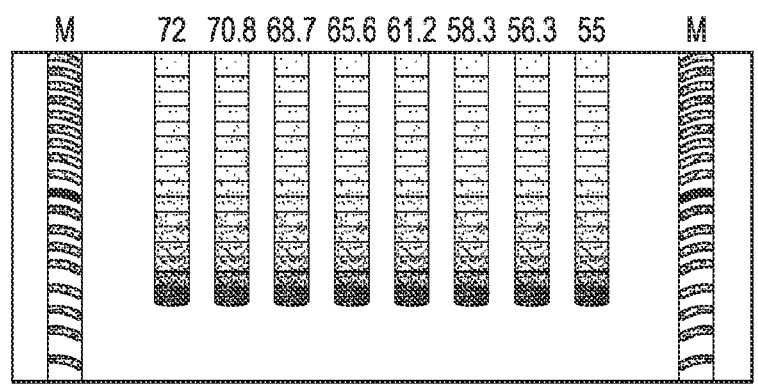
FIG. 14A shows ligated product of target specific ssNA can be amplified in a temperature range of at least 55 to 72 degrees Celsius when spiked into a background of human genomic DNA.
Figure 14B:
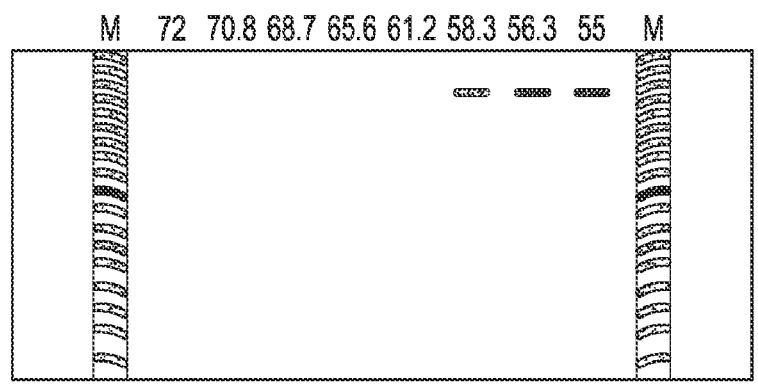
FIG. 14B shows human genomic DNA control without the ligated product produced no amplified product material from at least 65.6 to 72 degrees Celsius.

A PCR temperature gradient demonstrated that the ligated product of a BRAF specific ssNA can be amplified in a temperature range of at least 55 to 72 degrees Celsius when spiked into a background of human genomic DNA, as illustrated in FIG. 14A. As illustrated in FIG. 14B, human genomic DNA control without the ligated product produced no amplified product material from at least 65.6 to 72 degrees Celsius.

Example 6: Dynamic Molecular Indexing Processes

Figure 16:
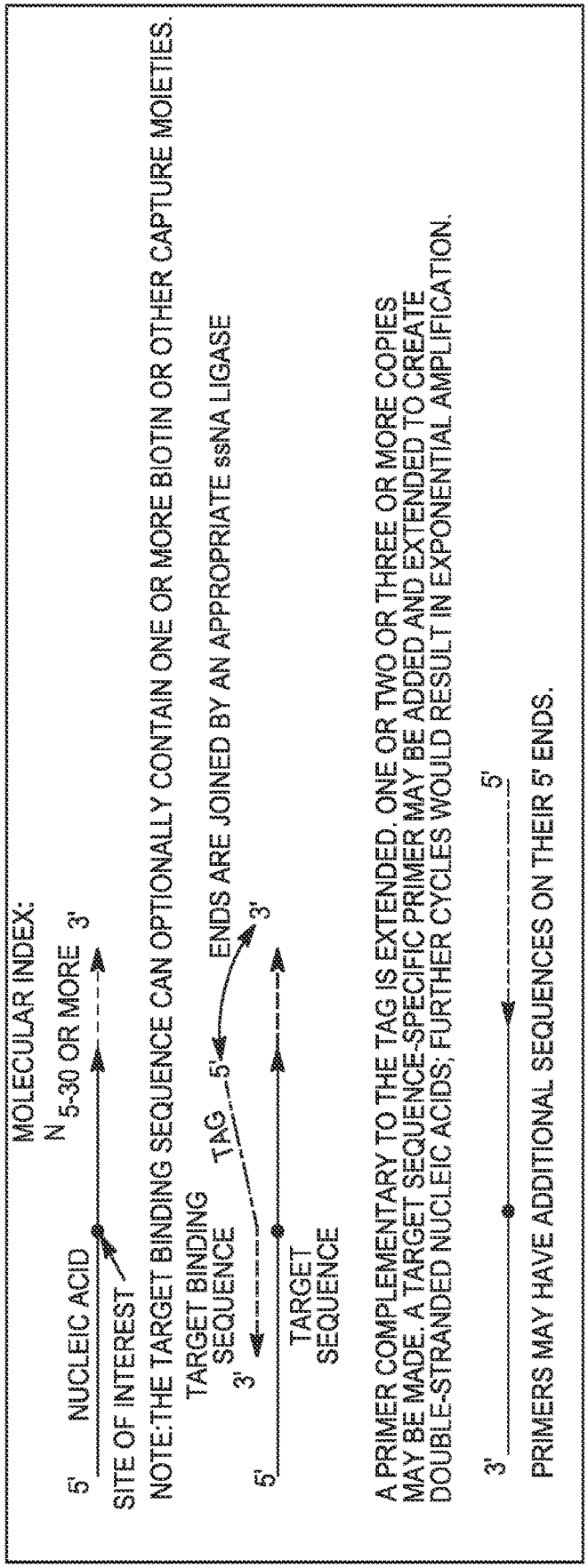
FIG. 16 shows an example of universal dynamic molecular indexing followed by a specific TargeTag with a site of interest 3' of the target site and one tag.

Non-limiting examples of certain Dynamic Molecular Indexing (DMI) processes are illustrated in FIGS. 16 to 25 and FIG. 28. FIG. 16 illustrates Dynamic Molecular Indexing (DMI) of a first ssNA using terminal transferase and a mixture of nucleotides. The first ssNA is annealed to a second ssNA in a locus-specific manner. In the presence of an appropriate ssNA ligase, the 3' end of the first ssNA and the 5' end of the second ssNA are ligated together. A primer complementary to the Tag can be added and extended. One or two or three or more copies can be made under amplification conditions (e.g., linear amplification or exponential amplification). A Target Sequence-specific primer may be added and extended to create double-stranded nucleic acids. Further cycles result in exponential amplification. Primers may have additional sequences on their 5' ends. Different combinations of 5' and 3' ends of the first ssNA and the second ssNA as described in Table 2 may be used as appropriate for the ligation.

Figure 17:
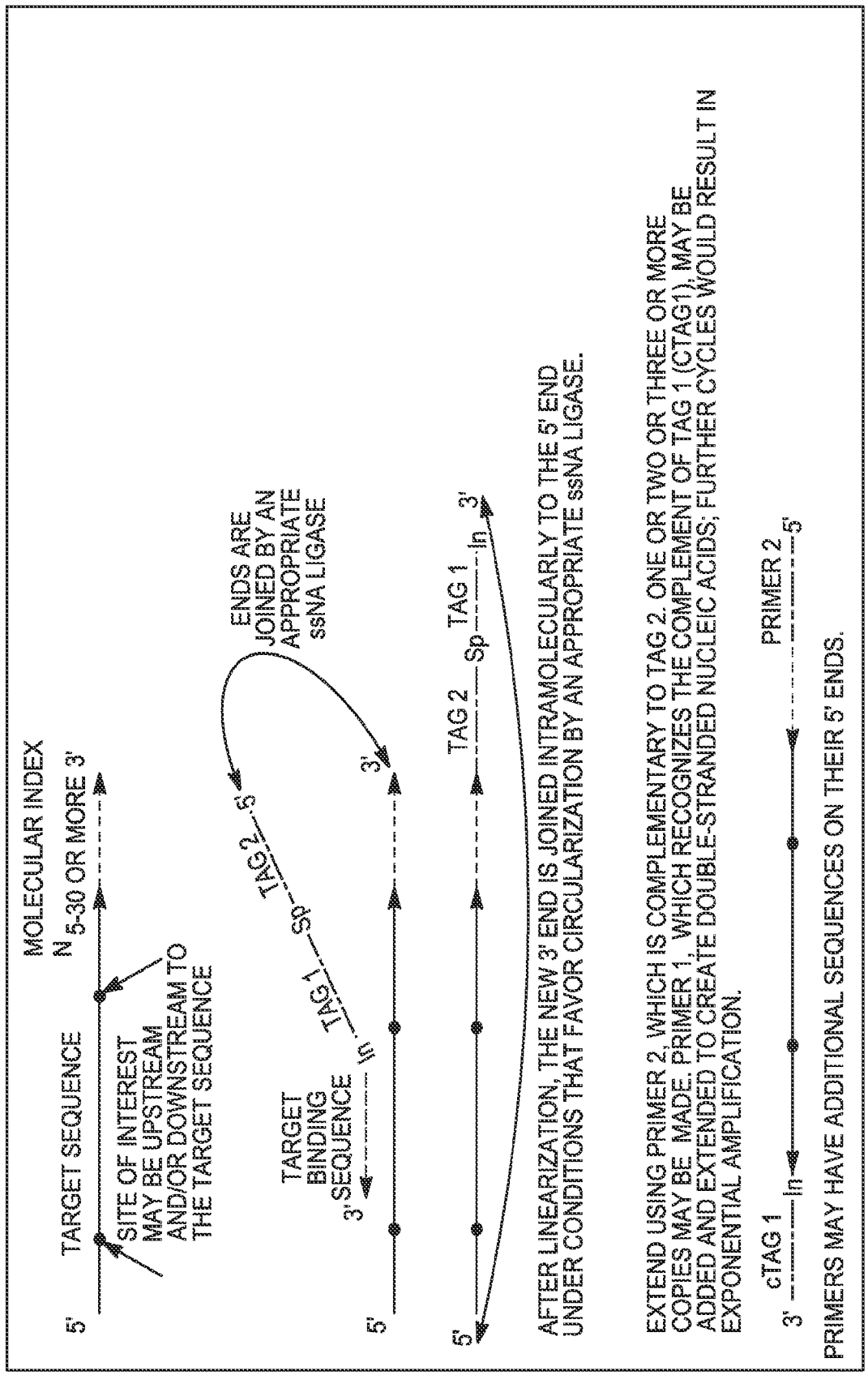
FIG. 17 shows an example of universal dynamic molecular indexing followed by a specific TargeTag with a site of interest 3' and/or 5' of the target site and two tags.

FIG. 17 illustrates DMI of a first ssNA using terminal transferase and a mixture of nucleotides. The first ssNA is then annealed to a second ssNA in a locus-specific manner. In the presence of an appropriate ssNA ligase, the 3' end of the first ssNA and the 5' end of the second ssNA are ligated together to form a new ssNA. In this non-limiting example, the product is linearized with endonuclease V, which recognizes deoxyinosine (In) and cleaves the second and/or third phosphodiester bonds 3' to deoxyinosine, leaving a 3'-hydroxyl and 5'-phosphate. After linearization, the new 3' end is joined intramolecularly to the 5' end of the new ssNA under conditions that favor circularization by an appropriate ssNA ligase. In this way, both ends of the new ssNA are tagged. The site(s) of interest may be upstream and/or downstream to the Target sequence. Primer 2, which is complementary to Tag 2, may be added and one or two or three or more copies may be made. Primer 1, which recognizes the complement of Tag 1 (cTag1), may be added and extended to create double-stranded nucleic acids and further cycles would result in exponential amplification. A spacer (Sp) that cannot be traversed by the polymerase used may be inserted between Tag 1 and Tag 2 so that only linear copies result from the action of the polymerase. Different combinations of 5' and 3' ends of the first ssNA and the second ssNA as described in Table 2 may be used as appropriate for each ligation. Primers may have additional sequences on their 5' ends.

Figure 18:
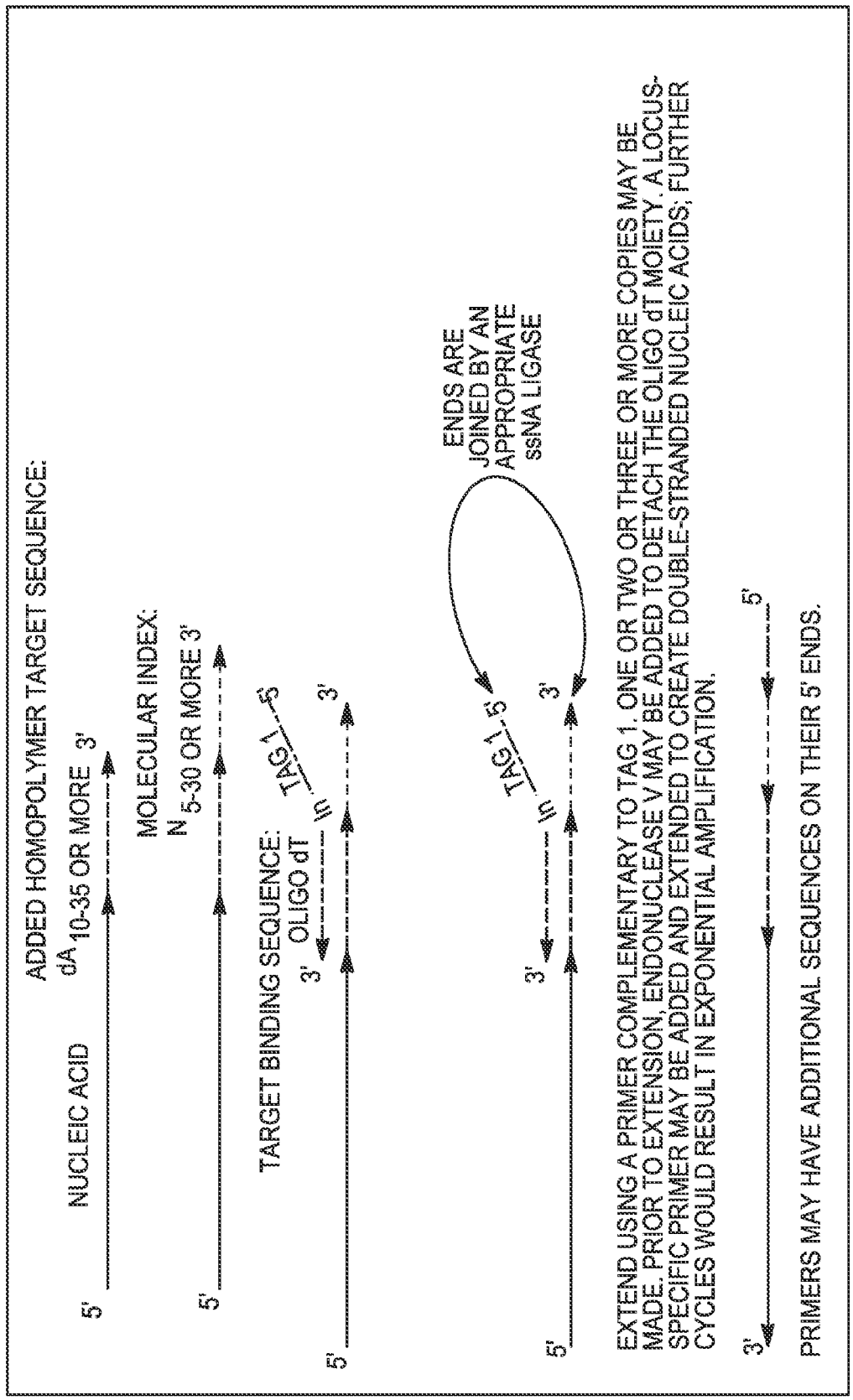
FIG. 18 shows an example of universal dynamic molecular indexing using a PolyA (as an example; another homopolymer may also be used) binding sequence and a universal TargeTag with one tag.

FIG. 18 shows how DMI can be performed using terminal transferase and a single nucleotide, resulting in a homopolymer of varying length attached to the first ssNA. Optionally, one, or two, or three additional types of nucleotides, each different from the first single nucleotide, may be added to create a mixture of two, or, three, or four different nucleotides, resulting in a more complex and diversified molecular index than is possible with just a single nucleotide. The homopolymer (in this example, poly dA) may also serve as a Target Site for the second ssNA (in this example, with an oligo dT Target Binding Sequence). After annealing and in the presence of an appropriate ssNA ligase, the 3' end of the first ssNA and the 5' end of the second ssNA are ligated together. A primer complementary to the Tag may be added and extended. One or two or three or more copies may be made. If a cleavable nucleotide (e.g., a deoxyinosine residue) is included in the second ssNA, a cleaving agent (e.g., Endonuclease V) may be added prior to extension to detach the oligo dT moiety used in this example. A locus-specific primer may be added and extended to create double-stranded nucleic acids and further cycles would result in exponential amplification. Primers may have additional sequences on their 5' ends. Different combinations of 5' and 3' ends of the first ssNA and the second ssNA as described in Table 2 may be used as appropriate for the ligation.

Figure 19:
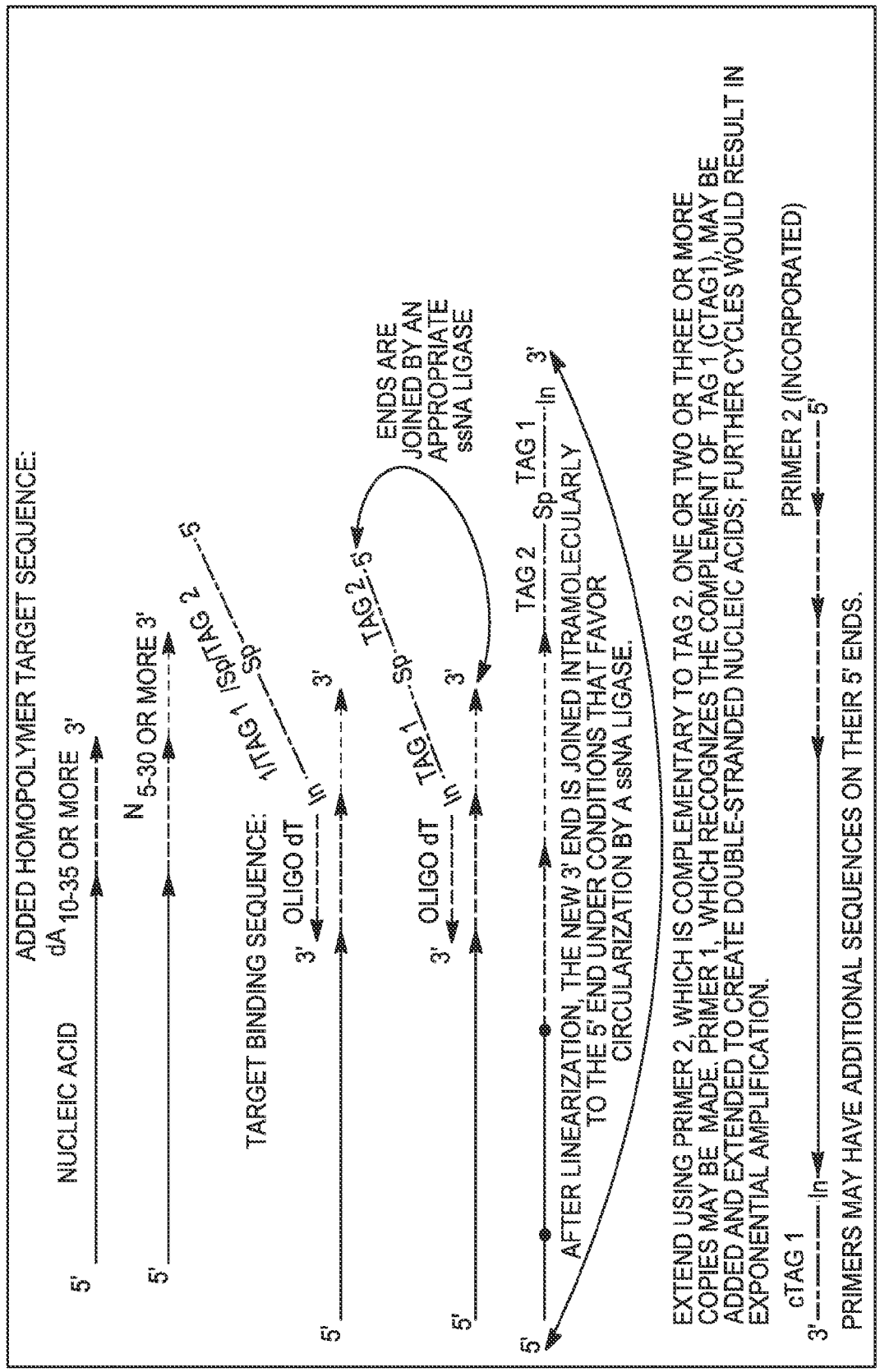
FIG. 19 shows an example of universal dynamic molecular indexing using a PolyA (as an example; another homopolymer may also be used) binding sequence and a universal TargeTag with two tags.

FIG. 19 shows how DMI can be performed with terminal transferase and a single nucleotide, resulting in a homopolymer of varying length being attached to the first ssNA. Three additional types of nucleotides are then added resulting in a complex and diversified molecular index. The homopolymer (in this example, poly dA) serves as a Target Site for the second ssNA (in this example, with an oligo dT Target Binding Sequence). After annealing and in the presence of an appropriate ssNA ligase, the 3' end of the first ssNA and the 5' end of the second ssNA are ligated together. After linearization, the new 3' end is joined intramolecularly to the 5' end of the new ssNA under conditions that favor circularization by an appropriate ssNA ligase. In this way, both ends of the new ssNA are tagged. Primer 2, which is complementary to Tag 2, may be added and one or two or three or more copies may be made. Primer 1, which recognizes the complement of Tag 1 (cTag1), may be added and extended to create double-stranded nucleic acids and further cycles would result in exponential amplification. A spacer (Sp) that cannot be traversed by the polymerase used may be inserted between Tag 1 and Tag 2 so that only linear copies result from the action of the polymerase. Different combinations of 5' and 3' ends of the first ssNA and the second ssNA as described in Table 2 may be used as appropriate for each ligation. Primers may have additional sequences on their 5' ends.

Figure 20:
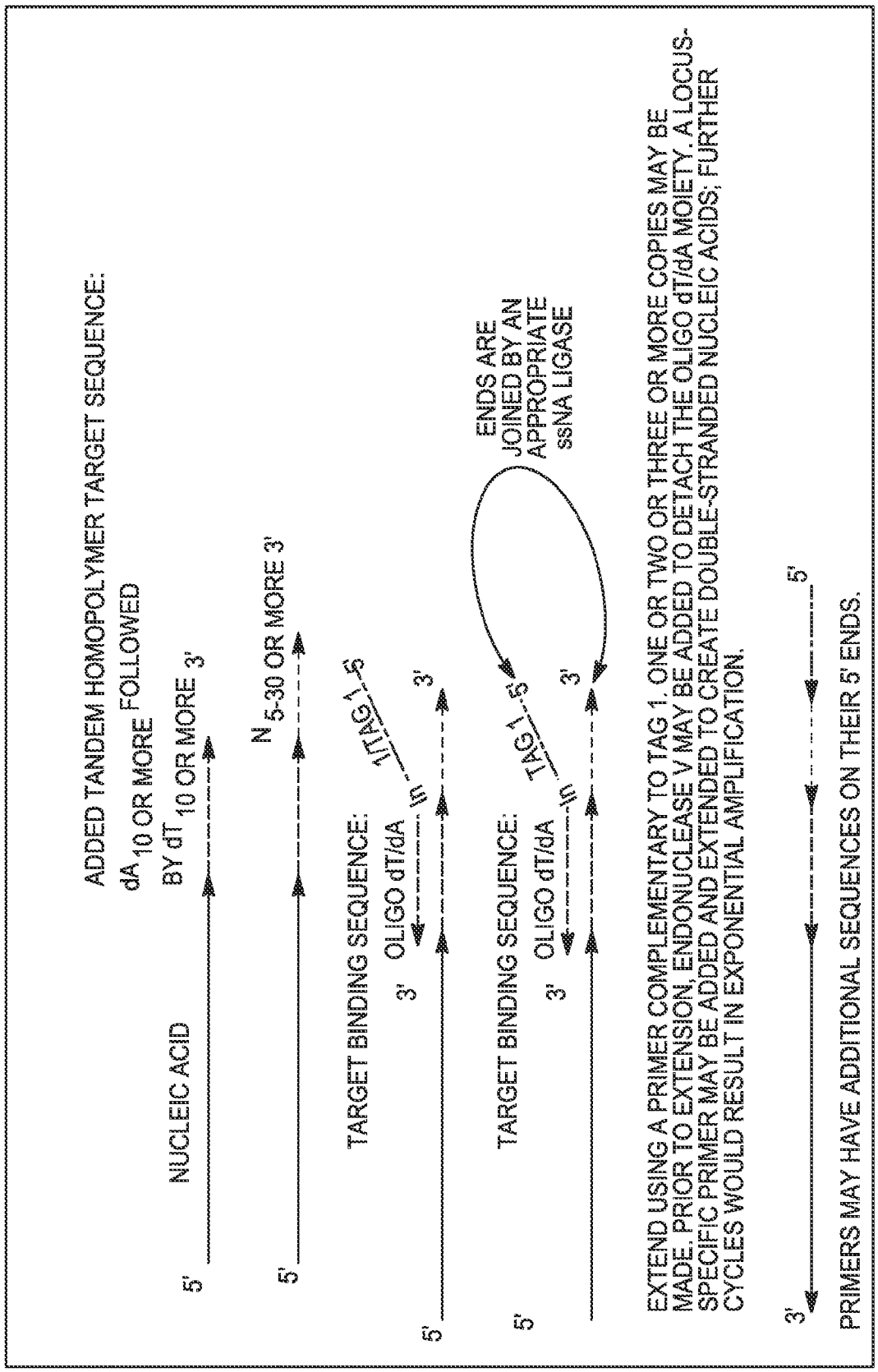
FIG. 20 shows an example of universal dynamic molecular indexing using tandem homopolymers for the binding site and a universal TargeTag with one tag.

FIG. 20 shows how DMI can be performed with terminal transferase and a single nucleotide, resulting in a homopolymer (in this example, poly dA). After the dATP in the reaction is neutralized, a second, single nucleotide is added to create a Tandem Homopolymer (in this example, poly dA/dT). Two different additional types of nucleotides are then added resulting in a complex and diversified molecular index. The Tandem Homopolymer serves as a Target Site for the second ssNA (in this example, with an oligo dT/dA Target Binding Sequence). After annealing and in the presence of an appropriate ssNA ligase, the 3' end of the first ssNA and the 5' end of the second ssNA are ligated together. A primer complementary to the Tag may be added and extended. One or two or three or more copies may be made. If a cleavable nucleotide (e.g., deoxyinosine residue) is included in the second ssNA, then a cleaving agent (e.g., Endonuclease V) may be added prior to extension to detach the oligo dT moiety used in this example. A locus-specific primer may be added and extended to create double-stranded nucleic acids and further cycles would result in exponential amplification. Different combinations of 5' and 3' ends of the first ssNA and the second ssNA as described in Table 2 may be used as appropriate for each ligation. Primers may have additional sequences on their 5' ends.

Figure 21:
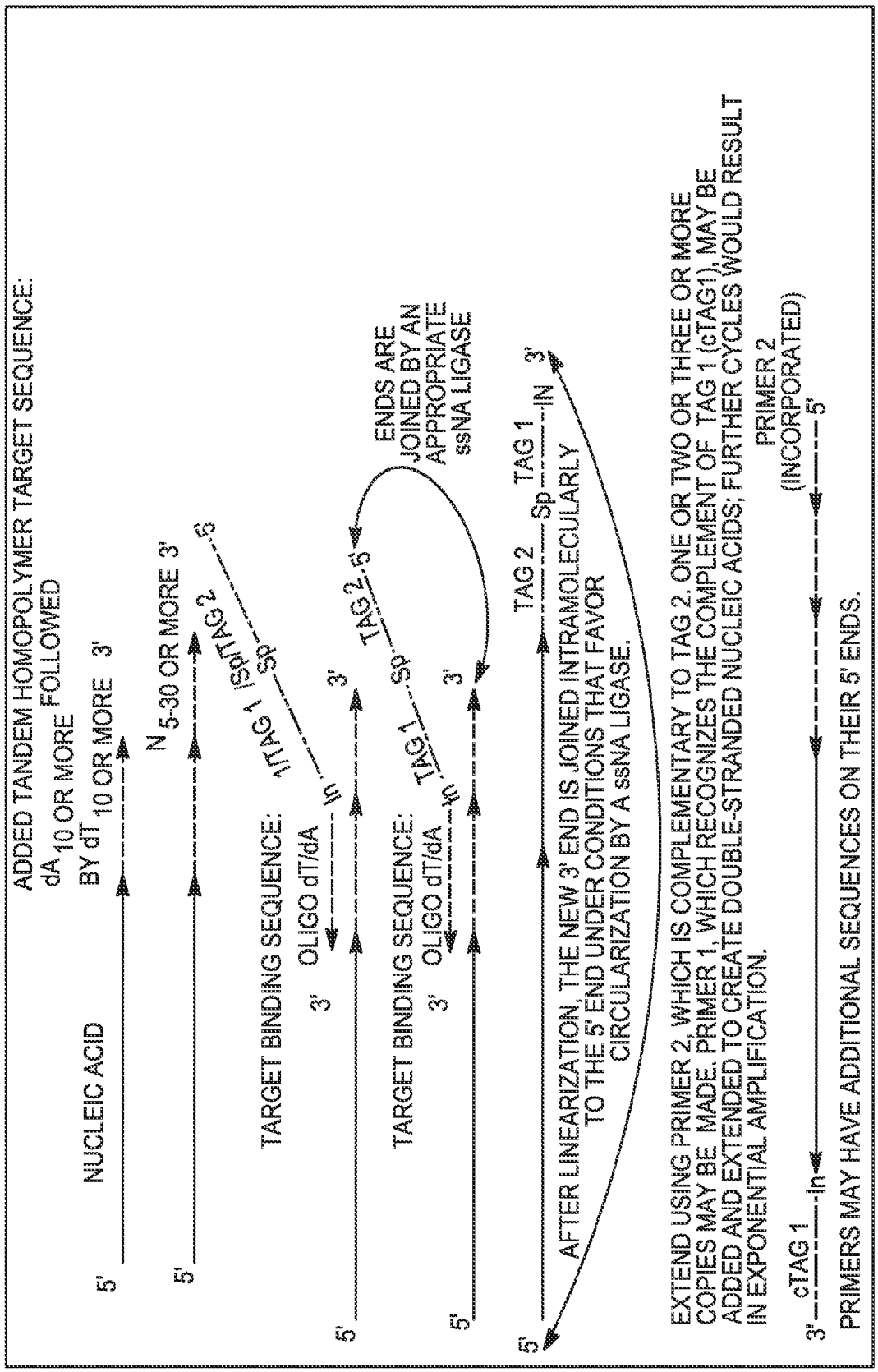
FIG. 21 shows an example of universal dynamic molecular indexing using tandem homopolymers for the binding site and a universal TargeTag with two tags.

FIG. 21 shows how DMI can be performed with terminal transferase and a single nucleotide, resulting in a homopolymer (in this example, poly dA). After the dATP in the reaction is neutralized, a second, single nucleotide is added to create a Tandem Homopolymer (in this example, poly dA/dT). Two different additional types of nucleotides are then added resulting in a complex and diversified molecular index. The Tandem Homopolymer serves as a Target Site for the second ssNA (in this example, with an oligo dT/dA Target Binding Sequence). After annealing and in the presence of an appropriate ssNA ligase, the 3' end of the first ssNA and the 5' end of the second ssNA are ligated together. After linearization, the new 3' end is joined intramolecularly to the 5' end of the new ssNA under conditions that favor circularization by an appropriate ssNA ligase. In this way, both ends of the new ssNA are tagged. Primer 2, which is complementary to Tag 2, may be added and one or two or three or more copies may be made. Primer 1, which recognizes the complement of Tag 1 (cTag1), may be added and extended to create double-stranded nucleic acids and further cycles would result in exponential amplification. A spacer (Sp) that cannot be traversed by the polymerase used may be inserted between Tag 1 and Tag 2 so that only linear copies result from the action of the polymerase. Different combinations of 5' and 3' ends of the first ssNA and the second ssNA as described in Table 2 may be used as appropriate for each ligation. Primers may have additional sequences on their 5' ends.

Figure 22:
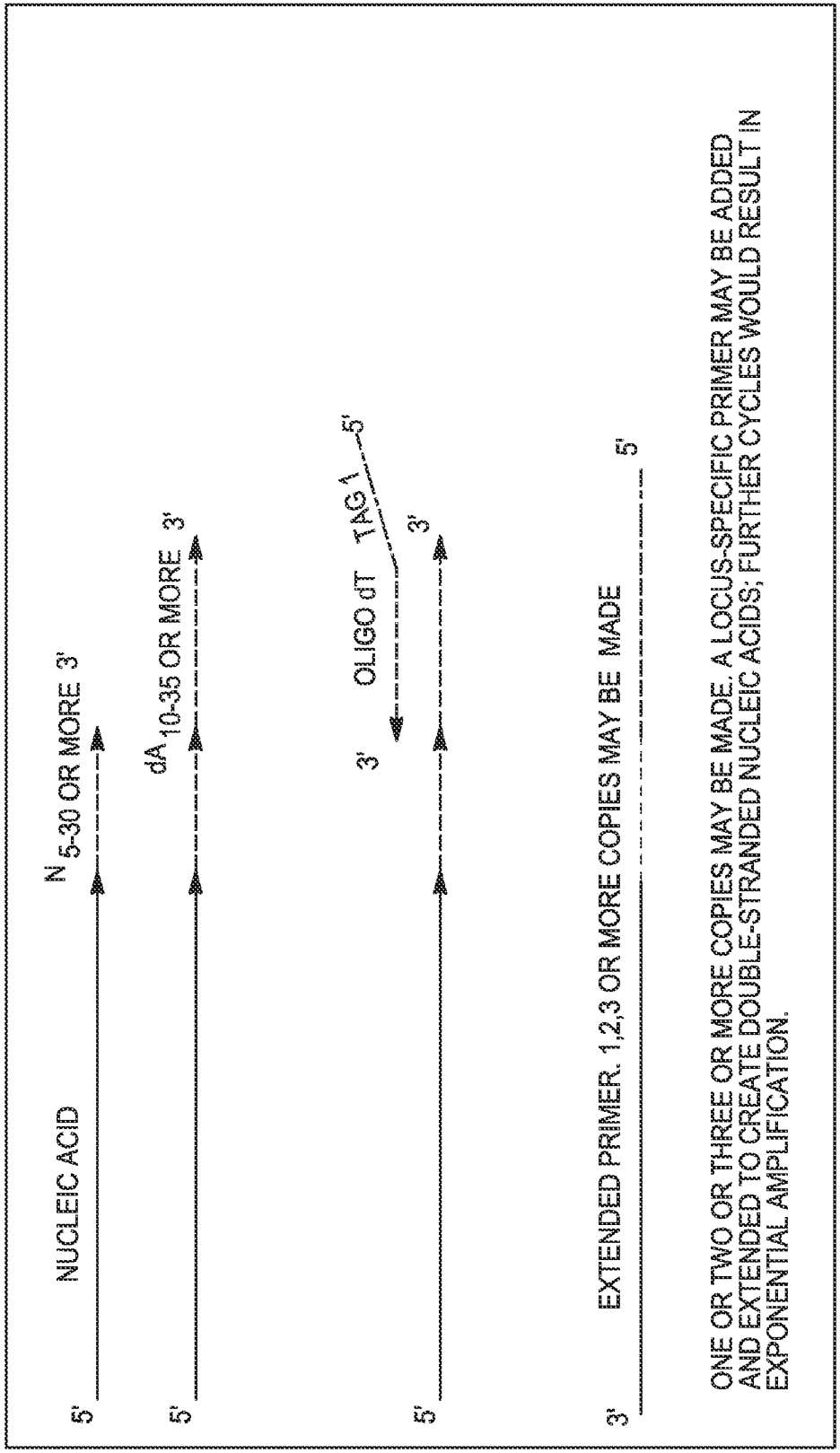
FIG. 22 shows an example of universal dynamic molecular indexing using a PolyA (or other homopolymer) priming site and a universal primer with one tag.

FIG. 22 show how DMI can be performed with terminal transferase and a mixture of nucleotides, resulting in a complex and diversified molecular index. After the dNTP mixture in the reaction is neutralized, a single nucleotide is added to create a Homopolymer tail (in this example, poly dA) 3' of the Molecular Index. A primer complementary to the poly dA tail (in this example, an oligo dT) with a 5' extension with Tag 1 is be added and extended. One or two or three or more copies may be made. A locus-specific primer may be added and extended to create double-stranded nucleic acids and further cycles would result in exponential amplification. Primers may have additional sequences on their 5' ends.

Figure 23:
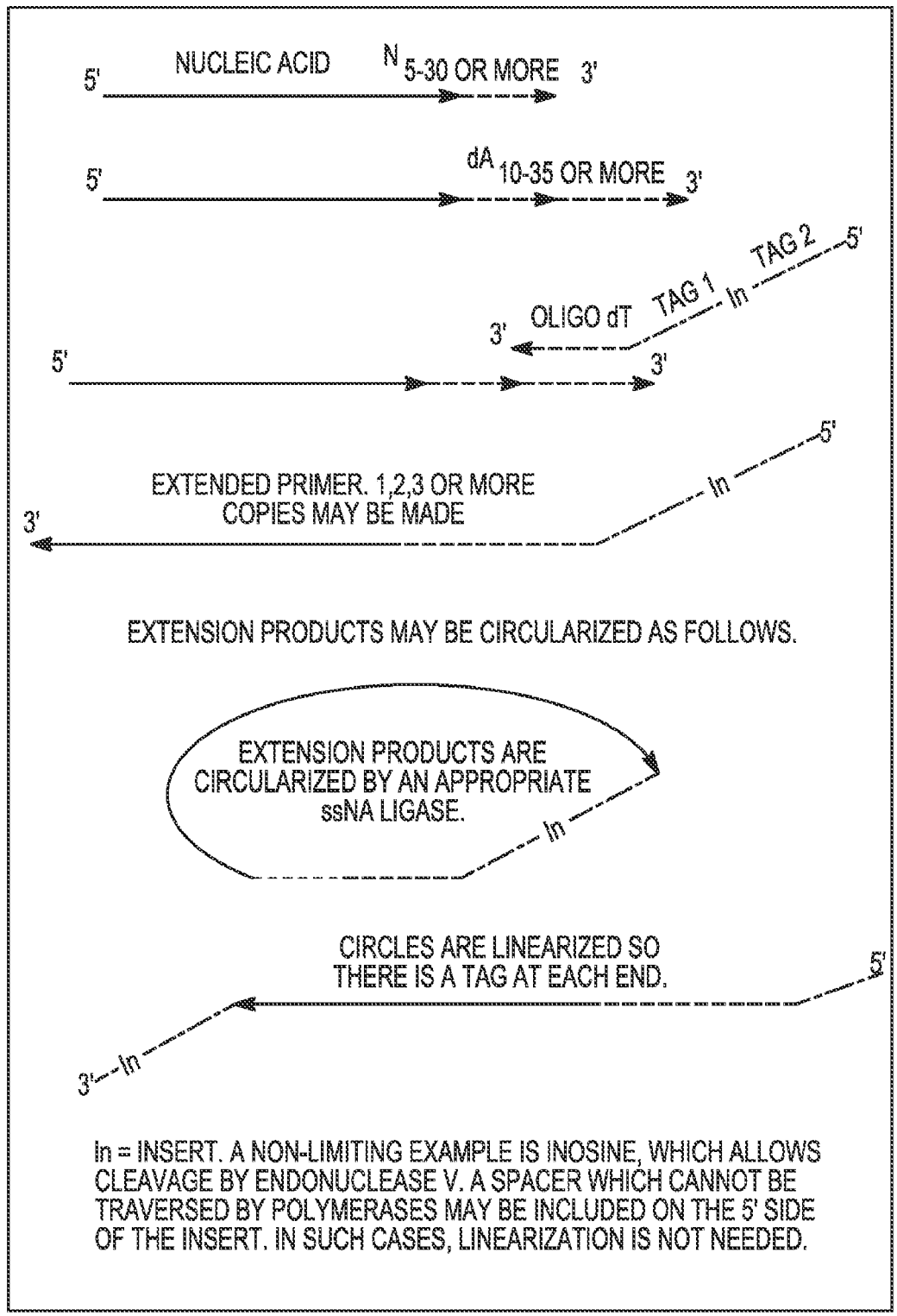
FIG. 23 shows an example of universal dynamic molecular indexing using a PolyA (or other homopolymer) priming site and a universal primer with two tags.

FIG. 23 shows how DMI can be performed with terminal transferase and a mixture of nucleotides, resulting in a complex and diversified molecular index. After the dNTP mixture in the reaction is neutralized, a single nucleotide is added to create a Homopolymer tail (in this example, poly dA) 3' of the Molecular Index. A primer complementary to the poly dA tail (in this example, an oligo dT) with a 5' extension containing Tag 1, a deoxyinosine residue, and Tag 2 is added and extended. One or two or three or more copies may be made. Extension products may be circularized using ssNA Ligase, and the nucleic acid can have different combinations of 5' and 3' ends, as described in Table 2, for example. The circularized ssNA may be linearized, and in a non-limiting example, dexoyinosine is cleaved by Endonuclease V. A spacer that cannot be traversed by polymerases may be included on the 5' side of the insert, and in such cases, linearization is not needed. Use of primers appropriate for Tag 1 and Tag 2 can be used to create double-stranded nucleic acids and further cycles would result in exponential amplification. Primers may have additional sequences on their 5' ends.

Figure 24:
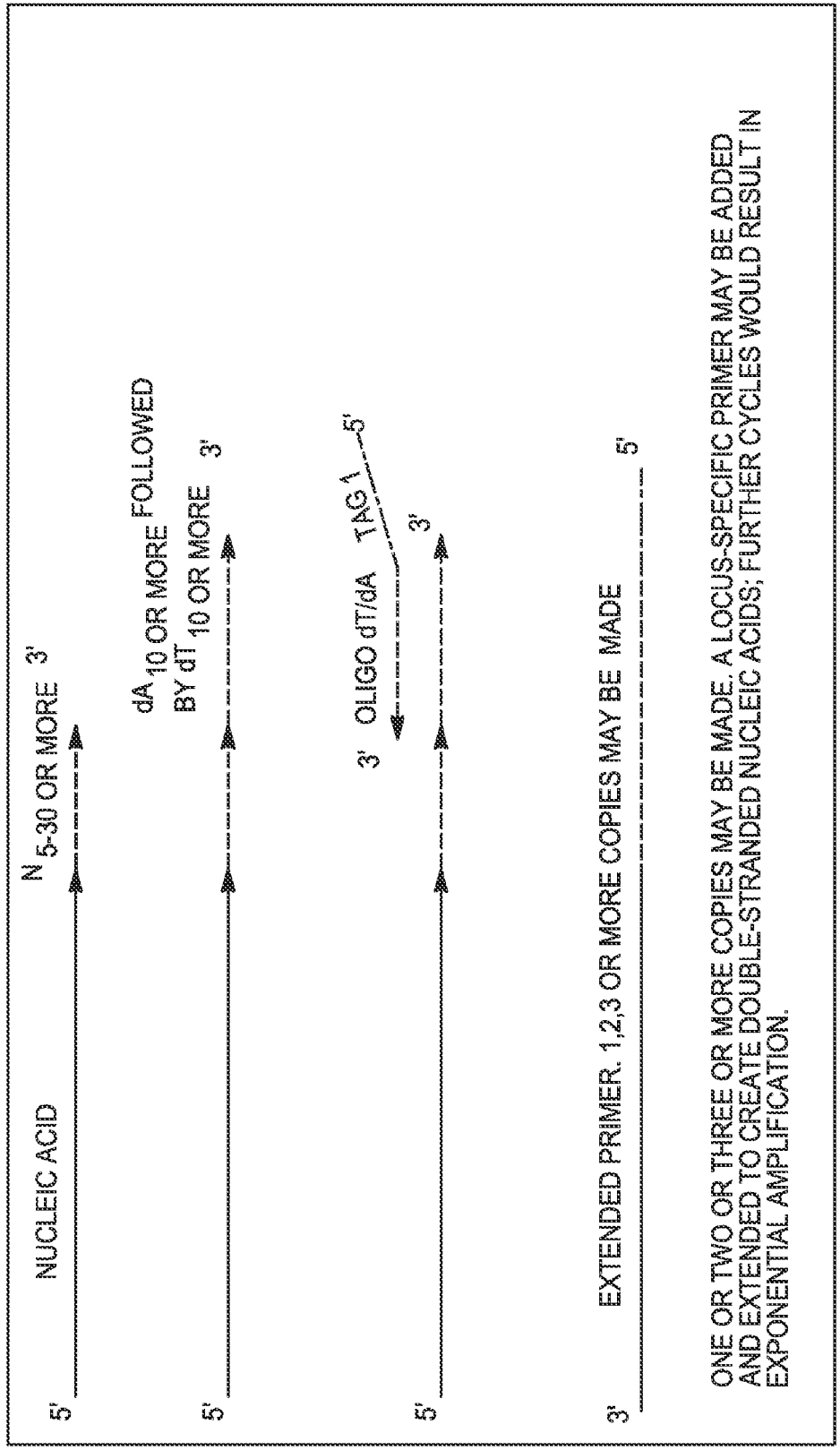
FIG. 24 shows an example of universal dynamic molecular indexing using a PolyA (or other homopolymer)/PolyT (or other homopolymer) priming site and a universal primer with one tag.

FIG. 24 shows how DMI can be performed with terminal transferase and a mixture of nucleotides, resulting in a complex and diversified molecular index. After the dNTP mixture in the reaction is neutralized, a single nucleotide is added to create a Homopolymer tail (in this example, poly dA) 3' of the Molecular Index. After the dATP in the reaction is neutralized, a second, single nucleotide is added to create a Tandem Homopolymer (in this example, poly dA/dT). A primer complementary to the poly dA/dT tail (in this example, an oligo dT/dA) with a 5' extension containing Tag 1 is added and extended. One or two or three or more copies may be made. A locus-specific primer may be added and extended to create double-stranded nucleic acids and further cycles would result in exponential amplification. Primers may have additional sequences on their 5' ends.

Figure 25:
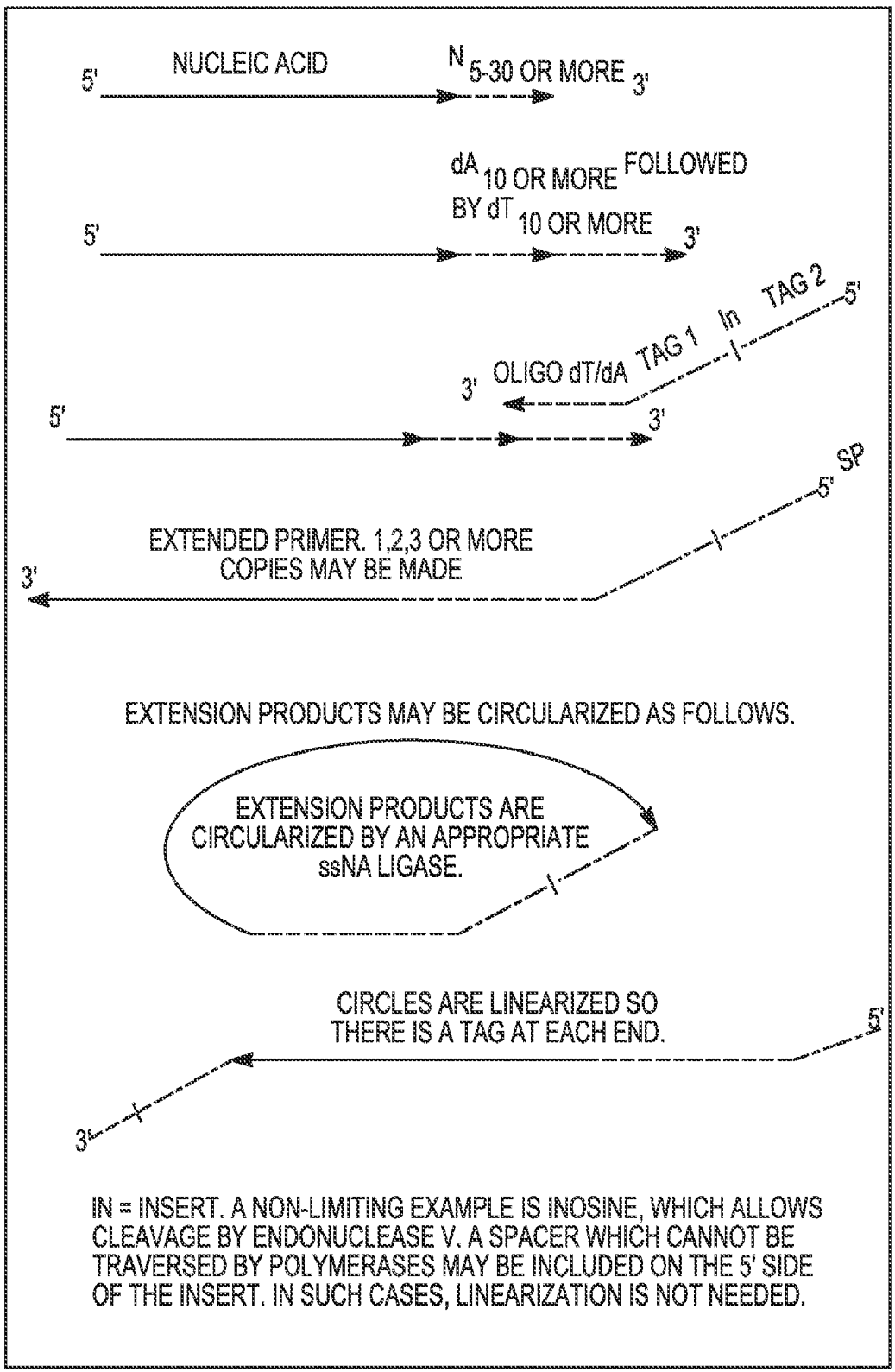
FIG. 25 shows an example of universal dynamic molecular indexing using a PolyA (or other homopolymer)/PolyT (or other homopolymer) priming site and a universal primer with two tags.

FIG. 25 shows how DMI can be performed with terminal transferase and a mixture of nucleotides, resulting in a complex and diversified molecular index. After the dNTP mixture in the reaction is neutralized, a single nucleotide is added to create a Homopolymer tail (in this example, poly dA) 3' of the Molecular Index. After the dATP in the reaction is neutralized, a second, single nucleotide is added to create a Tandem Homopolymer (in this example, poly dA/dT). A primer complementary to the poly dA/dT tail (in this example, an oligo dT/dA) with a 5' extension containing Tag 1, a deoxyinosine residue, and Tag 2 is added and extended. One or two or three or more copies may be made. Extension products may be circularized using ssNA Ligase and the nucleic acid can include different combinations of 5' and 3' ends, as described in Table 2, for example. The circularized ssNA may be linearized, and in a non-limiting example, dexoyinosine is cleaved by Endonuclease V. A spacer which cannot be traversed by polymerases may be included on the 5' side of the insert, and in such cases, linearization is not needed. Use of primers appropriate for Tag 1 and Tag 2 can be used to create double-stranded nucleic acids and further cycles would result in exponential amplification. Primers may have additional sequences on their 5' ends.

FIG. 28 shows a non-limiting example of a DMI process. Such a process is useful for tagging fragmented nucleic acid, such as cell free nucleic acid (e.g., from blood, saliva or urine) for example, in a single container. In the illustrated DMI process, the same conditions used to add the DMI polynucleotide tag also can be used to add an OligodT Priming Site, and through it, a Universal Primer Sequence. Referring to FIG. 28, a DMI reaction is set up in Step 1 by combining in a single tube purified DNA, Terminal Transferase buffer (including $CoCl_2$), a dNTP mix containing all four dNTPs (i.e., dATP, dTTP, dCTP and dGTP), and Terminal Transferase (TdT). This mixture is then incubated for 30 minutes at 37° C., and then the TdT is inactivated by heating at 75° C. for 20 minutes. This process in Step 1 generates a high diversity of DMIs. Now that the DNA is tagged with DMIs, it can be used in a variety of downstream applications. In the method shown in FIG. 28, the dNTPs are inactivated by Shrimp Alkaline Phosphatase (SAP) in Step 2. After the SAP is in turn heat-inactivated, a polyA tail may be added in Step 3 by adding to the same tube dATP and fresh TdT followed by incubation for 30 minutes at 37° C. The TdT is then inactivated by heating at 75° C. for 20 minutes. This creates a polyA tail on all of the DMI tagged DNA molecules. In Step 4, linear amplification is accomplished by adding an OligodT primer that has on its 5' end a Universal Primer Sequence, dNTPs, a buffer adjustment mix to modify the cation concentrations, and a DNA polymerase, in this example, Phusion HS II DNA polymerase. Since each linear amplification event is an independent occurrence, correct, original, native sequence can be derived later by comparing all of the sequences for each particular DMI. In Step 5, exponential amplification is employed to preferentially amplify selected targets, e.g. a particular region of an oncogene. This preferential amplification is performed by adding a locus-specific primer (e.g. upstream from codon 600 of the BRAF oncogene) and a Universal Primer that includes the Universal Primer Sequence that was attached in Step 4. Amplification can take place at a stringent temperature compatible with both the locus-specific primer and Universal Primer. Note that since only one locus-specific primer is used, the "footprint" of the assay (i.e. the actual amount of DNA sequence needed for the assay to work) can be very small, a great advantage when using highly fragmented DNA. Also, the amplification primers can have at their 5' ends additional sequences necessary for highly multiplexed sequencing (HMS) or next generation sequencing (NGS) on any chosen platform. Sample-specific barcodes (sample specific indexes) may also be included. In Step 6, the dNTPs are inactivated by treatment with SAP and the primers are eliminated by Exonuclease I. Since no double-stranded adapters are used, preparation for NGS is simple and straightforward. Additional processing may be undertaken if desired. For example, if sample-specific barcodes/indexes were used, then samples may be pooled and further purified and concentrated for application to an NGS platform of one's choosing. Although the protocol shown in FIG. 28 made use of DNA, similar protocols can be devised for use with RNA, including mRNA, miRNA, and lncRNA. Variations of the protocol shown in the FIG. 28 also can be adapted readily to methodology illustrated in FIG. 15 to FIG. 25 and described herein.

Example 7: Time Course of dATP and dNTP Additions by Terminal Transferase

Figure 26:
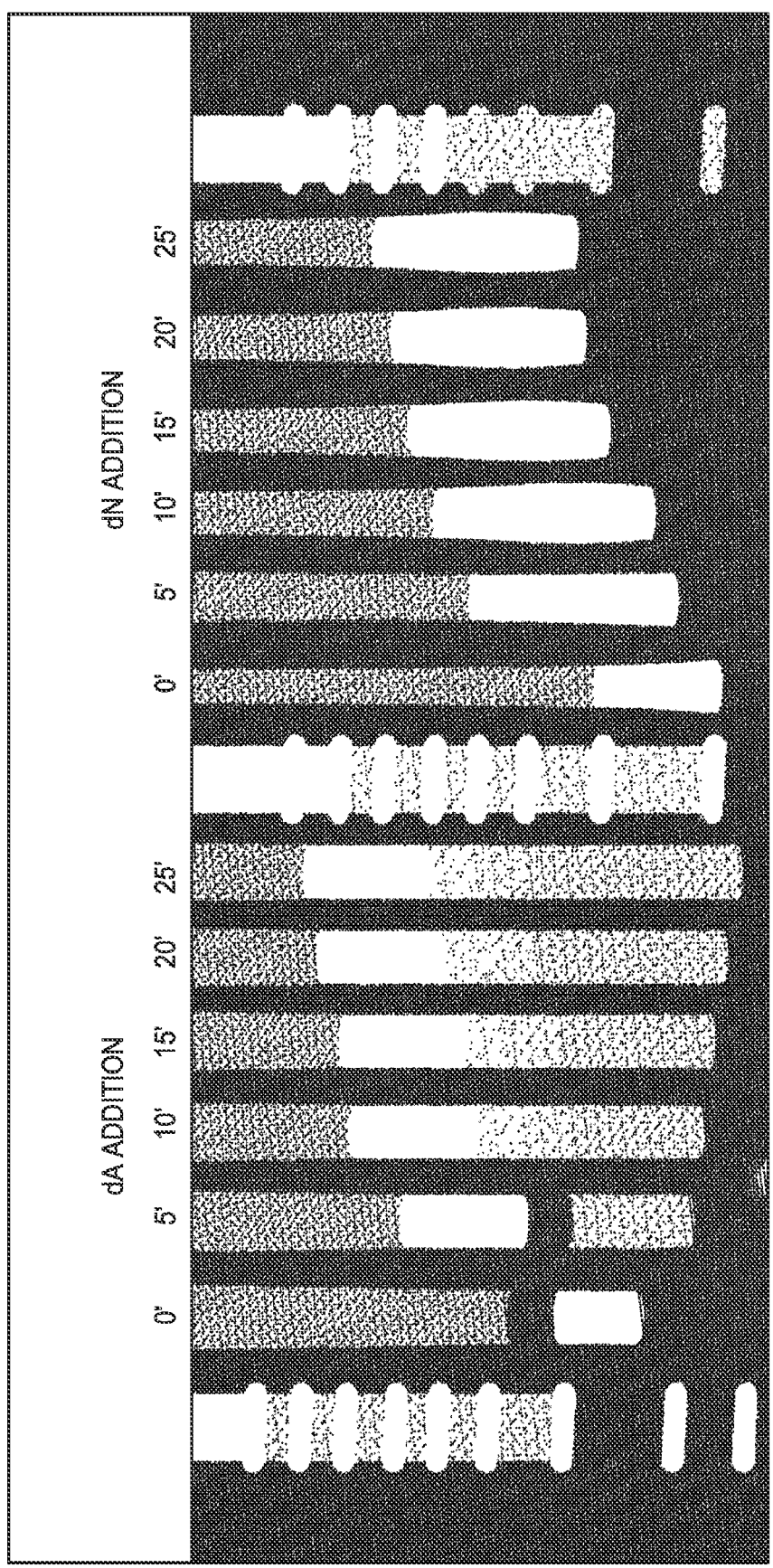
FIG. 26 shows a time course for dATP and dNTP additions by terminal transferase.

Terminal transferase is a robust, well-known enzyme. Its reaction conditions are well defined for addition of individual nucleotides, but are not as defined for mixtures of nucleotides. A synthetic 30-mer oligonucleotide therefore was generated and time courses were monitored to determine conditions for the addition of approximately 35 to 70 nucleotides using dATP and 10 to 70 nucleotides using a mixture of all four dNTPs. Results were analyzed using a Novex 15% acrylamide TBE Urea gel stained with SYBR Gold. By comparing the results to the 10 by DNA marker ladders included on gel, it was determined that in 25 minutes about 35 to 65 dA residues were added, and about 10 to 60 dN residues were added (see, e.g., FIG. 26). The range of additions can be readily increased by increasing the time of the reaction.

Example 8: Random Addition of dNTPs by Terminal Transferase

Figure 27:
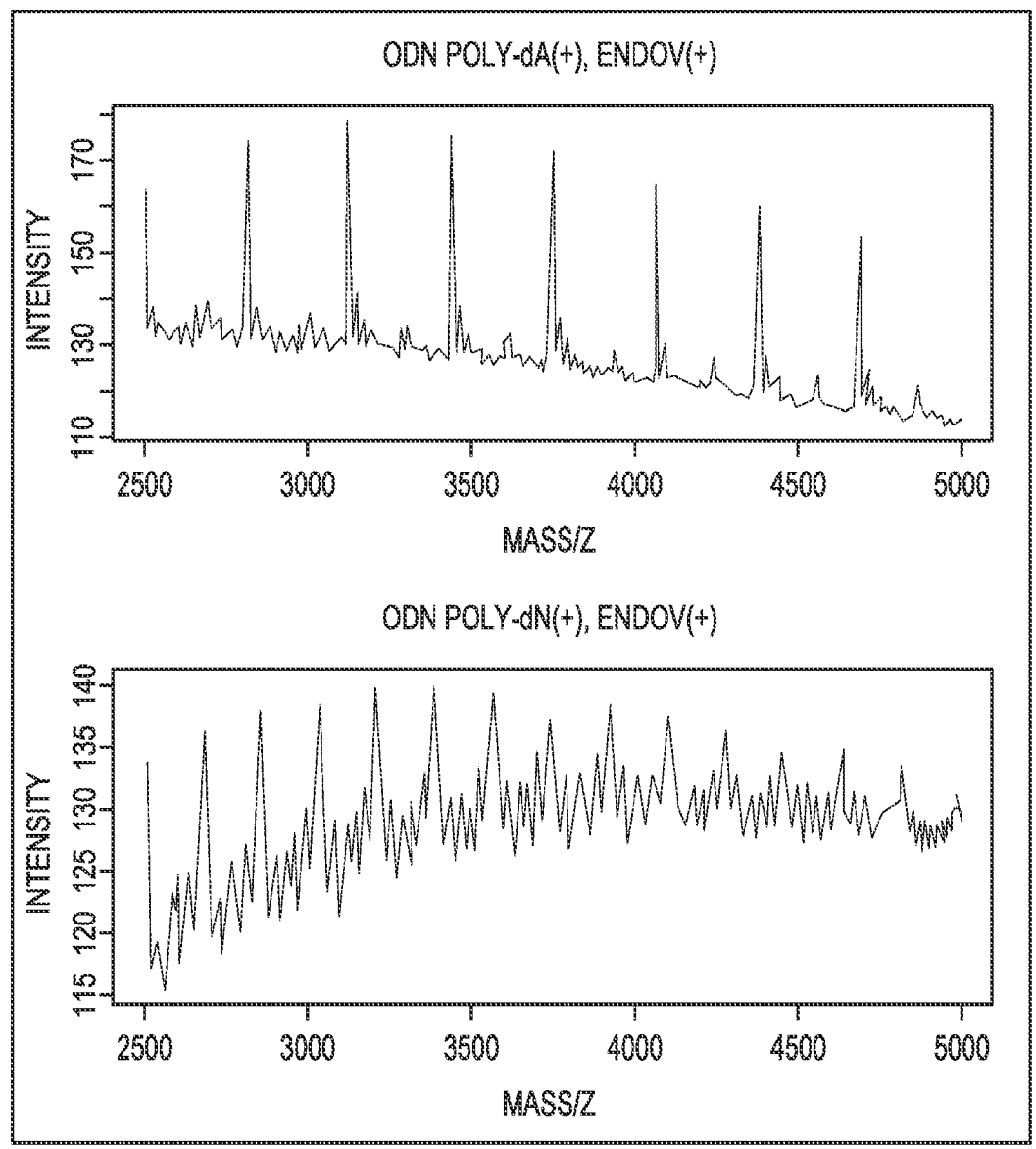
FIG. 27 shows that terminal transferase randomly adds dNTP residues to nucleic acid molecule.

Conditions are tested for the random addition of dN residues. Using a 30-mer oligonucleotide containing several inosine residues either dATP was used with terminal transferase or dNTP. After extension, the products were digested with Endonuclease V to destroy the oligonucleotide, allowing the extension products to be analyzed by MALDI-TOF mass spectrometry. The spectrum at the top of FIG. 27, for example, shows results for the dA addition. Sharp peaks are seen with appropriate spacing for the sequential addition of dA residues. In contrast, the spectrum at the bottom of FIG. 27, for example, shows multiple peaks for each residue added, indicating a random addition of nucleotides and little or no nucleotide preference when dNTPs are mixed together. With each additional nucleotide, the peaks become broader, a consequence of increasing mass diversity with the random addition of a nucleotide to each growing chain. The bottom spectrum greatly underestimates the sequence diversity since multiple differing sequences can have the same composition and hence the same mass.

Example 9: Examples of Certain Embodiments

Provided hereafter is a listing of certain non-limiting embodiments of the disclosure.

A1. A method for producing a single-stranded nucleic acid molecule, comprising:
    providing a first single-stranded nucleic acid (ssNA) molecule comprising a 5'-end, a target sequence, and a 3'-end;
    providing a second ssNA molecule comprising a 5'-phosphate moiety (optionally adenylated), a 5' leader sequence, a target binding sequence that is complementary to at least a portion of the target sequence, and a 3' end;
    hybridizing or annealing the first and second ssNA molecules under conditions wherein at least a portion of the target sequence and target binding sequence hybridize or anneal to each other by base pair complementarity; and
    contacting the hybridized or annealed molecules with a single-stranded nucleic acid ligase activity to ligate the 3'-end of the first ssNA molecule with the 5'phosphate moiety (optionally adenylated) of the second ssNA molecule to produce a single ssNA molecule.

A1.1. A method for producing a single-stranded nucleic acid molecule, comprising:
    contacting a first single-stranded nucleic acid (ssNA) molecule and a second ssNA molecule under hybridization or annealing conditions, thereby generating hybridized or annealed molecules, wherein:
        the first ssNA molecule comprises a 5'-end, a target sequence, and a 3'-end;
        the second ssNA molecule comprises a 5'-phosphate moiety (optionally adenylated), a 5' leader sequence, a target binding sequence that is complementary to at least a portion of the target sequence, and a 3' end;
        at least a portion of the target sequence and target binding sequence hybridize or anneal to each other by base pair complementarity; and
    contacting the hybridized or annealed molecules with a single-stranded nucleic acid ligase activity to ligate the 3'-end of the first ssNA molecule with the 5'phosphate moiety (optionally adenylated) of the second ssNA molecule to produce a single ssNA molecule.

A1.2. The method of embodiment A1 or A1.1, wherein a subsequence of four or more contiguous nucleotide bases in the 5' leader sequence in the second ssNA molecule is not complementary to a subsequence of four or more contiguous nucleotide bases in the target sequence in the first ssNA molecule.

A1.3. The method of embodiment A1 or A1.1, wherein a subsequence of four or more contiguous nucleotide bases in the 5' leader sequence in the second ssNA molecule is not complementary to a subsequence of four or more contiguous nucleotide bases in the first ssNA molecule.

A2. The method of any one of embodiments A1 to A1.3, wherein the 5'-end is dephosphorylated in the first ssNA molecule.

A3. The method of any one of embodiments A1 to A2, wherein the first ssNA molecule comprises a 3'-tail sequence.

A4. The method of any one of embodiments A1 to A3, wherein the target sequence in the first ssDNA molecule comprises 18-27 or 28-35 or more nucleotides.

A5. The method of any one of embodiments A1 to A4, wherein the first ssNA molecule further comprises a 3'-end extended with one or more T residues.

A5.1. The method of any one of embodiments A1 to A4, wherein the first ssNA molecule further comprises a 3'-end extended with one or more A residues.

A5.2. The method of any one of embodiments A1 to A4, wherein the first ssNA molecule further comprises a 3'-end extended with one or more C residues.

A5.3. The method of any one of embodiments A1 to A4, wherein the first ssNA molecule further comprises a 3'-end extended with one or more G residues.

A6. The method of any one of embodiments A1 to A5, wherein the first ssNA molecule further comprises a 5' target leader sequence.

A7. The method of any one of embodiments A1 to A6, wherein the first ssNA molecule further comprises a residue or sequence of interest 3' from the target sequence.

A8. The method of any one of embodiments A1 to A7, wherein the 5' phosphate in the second ssNA is adenylated.

A9. The method of any one of embodiments A1 to A8, wherein the second ssNA comprises a 3' tail sequence.

A10. The method of any one of embodiments A1 to A9, wherein the second ssNA comprises a blocked 3'-end.

A11. The method of any one of embodiments A1 to A10, wherein the second ssNA molecule comprises a G residue at its 5'-end.

A12. The method of any one of embodiments A1 to A11, wherein the 5' leader sequence in the second ssNA molecule comprises a primer binding sequence.

A13. The method of any one of embodiments A1 to A12, wherein the target sequence and the target binding sequence, when hybridized or annealed, has a melting temperature of about 40° C., or of about 50° C. or of about 60° C., or of about 70° C.

A14. The method of any one of embodiments A1 to A13, wherein the 5' leader sequence of the second ssNA molecule comprises a molecular index sequence.

A15. The method of embodiment A14, wherein the 5' leader sequence of the second ssNA molecule comprises a molecular index sequence and a primer binding sequence.

A16. The method of any one of embodiments A1 to A13, wherein the first ssNA molecule comprises a molecular index sequence.

A17. The method of embodiment A16, wherein the molecular index sequence is 3' of the target sequence.

A18. The method of any one of embodiments A14 to A17, comprising contacting the first ssNA molecule or the second ssNA molecule with a terminal transferase activity and a mixture comprising two or more different nucleotides under conditions in which the terminal transferase activity adds two or more nucleotides from the mixture of nucleotides to the first ssNA molecule or the second ssNA molecule as a molecular index sequence.

A19. The method of embodiment A18, wherein the mixture comprises two different nucleotides.

A20. The method of embodiment A18, wherein the mixture comprises three different nucleotides.

A21. The method of embodiment A18, wherein the mixture comprises four different nucleotides.

A22. The method of any one of embodiments A18 to A21, wherein the different nucleotides in the mixture are different deoxynucleotide triphosphates.

A23. The method of embodiment A22, wherein the different nucleotides in the mixture are chosen from adenosine triphosphate (ATP), guanosine triphosphate (GTP), cytidine triphosphate (CTP) and thymidine triphosphate (TTP).

A24. The method of any one of embodiments A18 to A23, wherein the molecular index sequence is about 5 nucleotide bases to about 30 or more nucleotide bases in length.

A25. The method of any one of embodiments A14 to A17, comprising contacting the first ssNA molecule or the second ssNA molecule with a terminal transferase activity and a composition comprising single nucleotide monomers under conditions in which the monomers are added to the 3' terminus of the first ssNA or the second ssNA by the terminal transferase activity, thereby adding a homopolynucleotide comprising the monomers to the 3' end of the first ssNA or the second ssNA.

A26. The method of embodiment A25, wherein the single nucleotide monomers in the composition are deoxynucleotide triphosphates.

A27. The method of embodiment A26, wherein the single nucleotide monomers in the composition are chosen from adenosine triphosphate (ATP), guanosine triphosphate (GTP), cytidine triphosphate (CTP) and thymidine triphosphate (TTP).

A28. The method of any one of embodiments A25 to A27, wherein the homopolynucleotide is about 10 nucleotide bases to about 35 or more nucleotide bases in length.

A29. The method of any one of embodiments A14 to A28, wherein the second ssNA molecule is in a plurality of second ssNA molecules, there are about $4^5$ to about $4^{30}$ or more different molecular index sequences or more, and each of the second ssNA molecules in the plurality of second ssNA molecules comprises a molecular index sequence.

A30. The method of any one of embodiments A16 to A28, wherein the first ssNA molecule is in a plurality of first ssNA molecules, there are about $4^5$ to about $4^{30}$ or more different molecular index sequences, and each of the first ssNA molecules in the plurality of first ssNA molecules comprises a molecular index sequence.

A31. The method of any one of embodiments A1 to A30, comprising contacting the single ssNA molecule with a single-stranded exonuclease activity to digest the single ssNA molecule, thereby generating a digested ssNA molecule.

A32. The method of embodiment A31, comprising heat inactivating the exonuclease activity.

A33. The method of embodiment A1 to A32, wherein the target binding sequence or linked sequence of the second ssNA molecule comprises one or more nucleotides chosen from uracil, inosine, abasic or other modified nucleotide.

A34. The method of embodiment A33, comprising:
contacting the molecules with a single-stranded exonuclease activity to digest single-stranded molecules,
optionally heat inactivating said exonuclease activity,
contacting the remaining molecules with an enzyme having an activity that removes the one or more nucleotides chosen from uracil, inosine, abasic, or modified nucleotide, wherein the activity is chosen from uracil-DNA glycosylase, Endonuclease V, APE 1, Endonuclease III, TMA Endonuclease III, or Endonuclease VIII,
optionally heat inactivating said uracil-DNA glycosylase, Endonuclease V, APE 1, Endonuclease III, or Endonuclease VIII activity,
hybridizing or annealing the resultant molecules with a primer oligonucleotide that is complementary to the primer binding sequence (wherein the primer optionally contains a 5' extension), and
contacting the resultant molecules with a polymerase activity to linearly amplify the resultant molecules.

A35. The method of any one of embodiments A1 to A34, wherein the first ssNA molecule is prepared from a biological specimen.

A36. The method of embodiment A35, wherein the specimen is chosen from a bodily fluid, including but not limited to blood plasma, blood serum, saliva and urine.

A37. The method of any one of embodiments A1 to A36, wherein the single ssNA molecule comprises a hairpin structure.

A37.1. The method of embodiment A37, wherein the single ssNA molecule comprises a hairpin structure at 25 degrees Celsius.

A38. The method of embodiment A37, wherein the hairpin structure comprises a loop of about 5 nucleotide bases to about 500 nucleotide bases in length.

A39. The method of embodiment A37 or A38, wherein the hairpin structure comprises a double-stranded region and a single-stranded region, and wherein the double-stranded region is about 18 nucleotides to about 35 or more nucleotide bases in length.

A40. The method of any one of embodiments A1 to A39, wherein:
the first ssNA molecule is from a double-stranded nucleic acid (dsNA) molecule comprising a sense first ssNA molecule and an antisense first ssNA molecule;
the sense first ssNA molecule and the antisense first ssNA molecule are contacted under hybridization or annealing conditions with (i) a sense second ssNA molecule comprising a target binding sequence complementary to the target sequence in the sense first ssNA molecule, and (ii) an antisense second ssNA molecule comprising a target binding sequence complementary to the target sequence in the antisense first ssNA molecule, thereby producing hybridized or annealed molecules;
at least a portion of the target sequence and the target binding sequence in the sense first ssNA molecule and the sense second ssNA molecule, and at least a portion of the target sequence and the target binding sequence in the antisense first ssNA molecule and the antisense second ssNA molecule, hybridize or anneal to each other by base pair complementarity under the hybridization and annealing conditions;
the hybridized or annealed molecules are contacted with a single-stranded nucleic acid ligase activity under ligation conditions;
the 3' end of the sense first ssNA molecule ligates to the 5' phosphate moiety (optionally adenylated) of the sense second ssNA molecule, and the 3' end of the antisense first ssNA molecule ligates to the 5' phosphate moiety (optionally adenylated) of the antisense second ssNA molecule, under the ligation conditions, thereby generating single ssNA molecules.

A41. The method of any one of embodiments A1 to A40, wherein the 5' leader sequence of the second ssNA comprises a primer binding sequence and the method comprises contacting the single ssNA molecule or digested ssNA molecule with a primer that binds to the primer binding sequence under extension conditions, thereby generating extension product.

A42. The method of embodiment A41, wherein the primer is extended past a location of interest in the single ssNA molecule or digested ssNA molecule.

A43. The method of embodiment A42, wherein the location of interest is a single nucleotide base.

A44. The method of embodiment A42, wherein the location of interest is a polynucleotide.

A45. The method of any one of embodiments A41 to A44, comprising amplifying the extension product, thereby generating amplicons.

A46. The method of any one of embodiments A41 to A45, wherein the extension product and/or the amplicons comprise one or more adapter sequences.

A47. The method of any one of embodiments A41 to A46, wherein the extension product and/or the amplicons comprise a sample specific sequence.

A48. The method of any one of embodiments A42 to A47, comprising identifying one or more nucleotide base species or nucleotide sequence species at the location of interest in the extension product and/or the amplicons, thereby identifying one or more species at the location of interest.

A50. The method of embodiment A48, wherein the identifying is performed by a sequencing process.

A51. The method of embodiment A48, wherein the identifying is performed by a mass spectrometry process.

A52. The method of any one of embodiments A48 to A51, comprising quantifying the one or more species at the location of interest, thereby providing a quantification.

A53. The method of embodiment A52, comprising sorting by one or more of the molecular index sequence, sample specific sequence, and nucleotide sequence species at the location of interest, thereby providing a sorting for a sample.

A54. The method of embodiment A53, comprising normalizing or scaling the number of a first species at the location of interest relative to a second species at the location of interest, thereby providing a normalized or scaled quantification of a species at the location of interest.

A55. The method of any one of embodiments A52 to A54, comprising determining the species at the location of interest for a sample according to the quantification, normalized or scaled quantification and/or sorting.

B1. A method for producing a single-stranded nucleic acid molecule, comprising:
contacting a first single-stranded nucleic acid (ssNA) molecule comprising a 5'-end that is optionally dephosphorylated, a target sequence, and a 3'-end with a terminal transferase activity and dNTPs under reaction conditions wherein a random sequence of nucleotide residues is added to the 3' end of the first ssNA molecule;
optionally heat inactivating the terminal transferase activity and/or removing or inactivating the dNTPs before optionally adding a 3'-tail sequence by use of a terminal transferase activity;

contacting the first ssNA molecule with a second ssNA molecule comprising a 5'-phosphate moiety that is optionally adenylated, a 5' leader sequence, a target binding sequence that is complementary to at least a portion of the target sequence, and an optional 3' tail and an optionally blocked 3'-end, hybridizing or annealing the first and second ssNA molecules under conditions wherein at least a portion of the target sequence and target binding sequence hybridize or anneal to each other by base pair complementarity;

contacting the hybridized or annealed molecules with a single-stranded nucleic acid ligase activity to ligate the 3'-end of the first ssNA molecule with the 5'phosphate moiety (optionally adenylated) of the second ssNA molecule to produce a single ssNA molecule.

C1. A kit for performing the method of any one of embodiments A1 to B1.

C2. A kit, comprising:
a single-stranded oligonucleotide comprising a 5'-phosphate moiety (optionally adenylated), a 5' leader sequence, a target binding sequence that is complementary to at least a portion of a target sequence in a specimen nucleic acid, and a 3' end; and a single-stranded ligase enzyme.

C3. The kit of embodiment C2, wherein the specimen nucleic acid comprises a 5'-end, a target sequence, and a 3'-end, and the single stranded ligase is capable of ligating the 3' end of a single strand of the specimen nucleic acid or modified specimen nucleic acid to the 5' end of the single-stranded oligonucleotide after the specimen nucleic acid and the oligonucleotide are hybridized or annealed to one another.

C4. The kit of embodiment C2 or C3, wherein the ligase enzyme is a thermostable enzyme.

C5. The kit of embodiment C4, wherein the ligase enzyme is from *M. thermoautotrophicum*.

C6. The kit of any one of embodiments C2 to C5, wherein the target binding sequence in the oligonucleotide comprises 18-27 or more nucleotides.

C7. The kit of any one of embodiments C2 to C6, wherein the 5' phosphate in the oligonucleotide is adenylated.

C8. The kit of any one of embodiments C2 to C7, wherein the oligonucleotide comprises a 3' tail sequence.

C9. The kit of any one of embodiments C2 to C8, wherein the oligonucleotide comprises a blocked 3'-end.

C10. The kit of any one of embodiments C2 to C9, wherein the oligonucleotide comprises a G residue at its 5'-end.

C11. The kit of any one of embodiments C2 to C10, wherein the oligonucleotide comprises a primer binding sequence.

C12. The kit of any one of embodiments C2 to C11, wherein the 5' leader sequence of the oligonucleotide comprises a molecular index sequence.

C13. The kit of embodiment C12, wherein the 5' leader sequence of the oligonucleotide comprises a molecular index sequence and a primer binding sequence.

C14. The kit of any one of embodiments C2 to C13, wherein the specimen nucleic acid has been processed to include an added nucleotide sequence.

C15. The kit of embodiment C14, wherein the added nucleotide sequence comprises a molecular index sequence.

C16. The kit of any one of embodiments C2 to C11, comprising a terminal transferase enzyme and a mixture comprising two or more different nucleotides.

C17. The kit of embodiment C16, comprising a terminal transferase enzyme co-factor.

C18. The kit of embodiment C17, wherein the co-factor is chosen from cobalt, manganese or magnesium.

C19. The kit of any one of embodiments C16 to C18, wherein the mixture comprises three or more different nucleotides.

C20. The kit of any one of embodiments C16 to C19, wherein the mixture comprises four different nucleotides.

C21. The kit of any one of embodiments C16 to C20, wherein the different nucleotides in the mixture are different deoxynucleotide triphosphates.

C22. The kit of embodiment C21, wherein the different nucleotides in the mixture are chosen from adenosine triphosphate (ATP), guanosine triphosphate (GTP), cytosine triphosphate (CTP) and thymidine triphosphate (TTP).

C23. The kit of any one of embodiments C14 to C22, comprising an isolated nucleotide.

C24. The kit of embodiment C23, wherein the isolated nucleotide is a nucleotide triphosphate.

C25. The kit of embodiment C24, wherein the isolated nucleotide is chosen from adenosine triphosphate (ATP), guanosine triphosphate (GTP), cytosine triphosphate (CTP) and thymidine triphosphate (TTP).

C26. The kit of any one of embodiments C2 to C23, comprising instructions for conducting a method of any one of embodiments A1 to B1.

D1. A single-stranded nucleic acid molecule comprising, from 5' to 3', a 5'-end that is optionally dephosphorylated, a target sequence, an optional 3'-tail, a 5' leader sequence, a target binding sequence, and an optional 3' tail and an optional blocked 3'-end.

E1. A method for modifying a nucleic acid, comprising:
contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding an index heteropolynucleotide comprising nucleotides in the mixture to the 3' end of the nucleic acid and generating an indexed nucleic acid.

E1.1. A method for modifying a nucleic acid, comprising:
contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a modified nucleic acid.

E2. The method of embodiment E1 or E1.1, wherein the nucleic acid is contacted with an enzyme comprising the terminal transferase activity.

E3. The method of embodiment E1, E1.1 or E2, wherein the mixture comprises two different nucleotides.

E4. The method of embodiment E1, E1.1 or E2, wherein the mixture comprises three different nucleotides.

E4.1. The method of embodiment E1, E1.1 or E2, wherein the mixture comprises four different nucleotides.

E5. The method of any one of embodiments E1 to E4, wherein the different nucleotides in the mixture are different deoxynucleotide triphosphates.

E6. The method of embodiment E5, wherein the different nucleotides in the mixture are chosen from adenosine triphosphate (ATP), guanosine triphosphate (GTP), cytidine triphosphate (CTP) and thymidine triphosphate (TTP).

E7. The method of any one of embodiments E1 to E6, comprising:
  (a) prior to contacting the nucleic acid with the mixture of two or more different nucleotides, contacting the nucleic acid with a terminal transferase activity and a composition comprising single nucleotide monomers under conditions in which the monomers are added to the 3' terminus of the nucleic acid by the terminal transferase activity, thereby adding a flag homopolynucleotide comprising the monomers to the 3' end of the nucleic acid and generating a flagged nucleic acid; and
  (b) contacting the flagged nucleic acid with a terminal transferase activity and the mixture of two or more different nucleotides under conditions in which nucleotides in the mixture are sequentially and randomly added to the 3' terminus of the flagged nucleic acid by the terminal transferase activity,
  thereby adding an index heteropolynucleotide comprising nucleotides in the mixture to the 3' end of the flagged nucleic acid and generating an indexed nucleic acid comprising, 5' to 3', the flag homopolynucleotide and the index heteropolynucleotide.

E7.1. The method of any one of embodiments E1 to E6, comprising:
  (a) prior to contacting the nucleic acid with the mixture of two or more different nucleotides, contacting the nucleic acid with a terminal transferase activity and a composition comprising single nucleotide monomers under conditions in which the monomers are added to the 3' terminus of the nucleic acid by the terminal transferase activity, thereby adding a homopolynucleotide comprising the monomers to the 3' end of the nucleic acid and generating a first modified nucleic acid; and
  (b) contacting the first modified nucleic acid with a terminal transferase activity and the mixture of two or more different nucleotides under conditions in which nucleotides in the mixture are sequentially and randomly added to the 3' terminus of the first modified nucleic acid by the terminal transferase activity, thereby adding a heteropolynucleotide comprising nucleotides in the mixture to the 3' end of the first modified nucleic acid and generating a second modified nucleic acid comprising, 5' to 3', the homopolynucleotide and the heteropolynucleotide.

E7.2. The method of any one of embodiments E1 to E6, comprising:
  (a) prior to contacting the nucleic acid with the mixture of two or more different nucleotides, contacting the nucleic acid with a terminal transferase activity and a first composition comprising single nucleotide monomers under conditions in which the monomers are added to the 3' terminus of the nucleic acid by the terminal transferase activity, thereby adding a mark homopolynucleotide comprising the monomers to the 3' end of the nucleic acid and generating a marked nucleic acid;
  (b) contacting the marked nucleic acid with a terminal transferase activity and the mixture of two or more different nucleotides under conditions in which nucleotides in the mixture are sequentially and randomly added to the 3' terminus of the flagged nucleic acid by the terminal transferase activity, thereby adding an index heteropolynucleotide comprising nucleotides in the mixture to the 3' end of the marked nucleic acid and generating an indexed nucleic acid comprising, 5' to 3', the mark homopolynucleotide and the index heteropolynucleotide; and
  (c) contacting the indexed nucleic acid with a terminal transferase activity and a second composition comprising single nucleotide monomers different than the single nucleotide monomers in the first composition under conditions in which the monomers in the second composition are added to the 3' terminus of the indexed nucleic acid by the terminal transferase activity, thereby adding a flag homopolynucleotide comprising the monomers in the second composition to the 3' end of the indexed nucleic acid and generating a modified nucleic acid comprising, 5' to 3', the mark homopolynucleotide, the index heteropolynucleotide and the flag homopolynucleotide.

E7.3. The method of any one of embodiments E1 to E6, comprising:
  (a) prior to contacting the nucleic acid with the mixture of two or more different nucleotides, contacting the nucleic acid with a terminal transferase activity and a first composition comprising single nucleotide monomers under conditions in which the monomers are added to the 3' terminus of the nucleic acid by the terminal transferase activity, thereby adding a first homopolynucleotide comprising the monomers to the 3' end of the nucleic acid and generating a first modified nucleic acid;
  (b) contacting the first modified nucleic acid with a terminal transferase activity and the mixture of two or more different nucleotides under conditions in which nucleotides in the mixture are sequentially and randomly added to the 3' terminus of the first modified nucleic acid by the terminal transferase activity, thereby adding a heteropolynucleotide comprising nucleotides in the mixture to the 3' end of the first modified nucleic acid and generating a second modified nucleic acid comprising, 5' to 3', the first homopolynucleotide and the heteropolynucleotide; and
  (c) contacting the second modified nucleic acid with a terminal transferase activity and a second composition comprising single nucleotide monomers different than the single nucleotide monomers in the first composition under conditions in which the monomers in the second composition are added to the 3' terminus of the second modified nucleic acid by the terminal transferase activity, thereby adding a second homopolynucleotide comprising the monomers in the second composition to the 3' end of the second modified nucleic acid and generating a third modified nucleic acid comprising, 5' to 3', the first homopolynucleotide, the heteropolynucleotide and the second homopolynucleotide.

E7.4. The method of any one of embodiments E1 to E6, comprising contacting the indexed nucleic acid (or modified nucleic acid) with a terminal transferase activity and a composition comprising single nucleotide monomers under conditions in which the monomers are added to the 3' terminus of the indexed nucleic acid (or modified nucleic acid) by the terminal transferase activity,
  thereby adding a flag homopolynucleotide comprising the monomers to the 3' end of the indexed nucleic acid (or modified nucleic acid) and generating a flagged nucleic acid comprising, 5' to 3', the index heteropolynucleotide and the flag homopolynucleotide.

E7.5. The method of any one of embodiments E1 to E6, comprising contacting the indexed nucleic acid (or modified nucleic acid) with a terminal transferase activity and a composition comprising single nucleotide monomers under conditions in which the monomers are added to the 3' terminus of the indexed nucleic acid (or modified nucleic acid) by the terminal transferase activity, thereby adding a homopolynucleotide comprising the monomers to the 3' end of the indexed nucleic acid (or modified nucleic acid) and generating an additionally modified nucleic acid comprising, 5' to 3', the heteropolynucleotide and the homopolynucleotide.

E7.6. The method of any one of embodiments E7 to E7.5, wherein each homopolynucleotide independently (i) consists of one nucleotide, or (ii) is a tandem homopolynucleotide comprising a first homopolynucleotide consisting of a first nucleotide and a second homopolynucleotide joined directly to the first homopolynucleotide that consists of a second nucleotide different than the first nucleotide.

E7.7. The method of embodiment E7.6, wherein the tandem homopolynucleotide is generated by (i) contacting the nucleic acid with the terminal transferase activity and a first composition comprising single nucleotide monomers under conditions in which the first homopolynucleotide is generated, and (ii) contacting the nucleic acid with the terminal transferase activity and a second composition comprising single nucleotide monomers different than the single nucleotide monomers in the first composition under conditions in which the second homopolynucleotide is generated.

E8. The method of any one of embodiments E1 to E7.7, wherein the nucleic acid is double-stranded or partially single-stranded and partially double-stranded.

E8.1. The method of any one of embodiments E1 to E7.7, wherein the nucleic acid is single-stranded.

E8.2. The method of embodiment E8.1, wherein the nucleic acid is the first single-stranded NA of embodiments A1 to A55.

E8.3. The method of embodiment E8.1, wherein the nucleic acid is the second single-stranded NA of embodiments A1 to A55.

E8.4. The method of any one of embodiments E1 to E8.3, wherein the nucleic acid comprises a candidate polynucleotide.

E8.5. The method of embodiment E8.4, wherein the candidate polynucleotide is located 5' of the heteropolynucleotide, the homopolynucleotide, the first homopolynucleotide and the second homopolynucleotide.

E9. The method of any one of embodiments E1 to E8.5, wherein the heteropolynucleotide is about 5 nucleotide bases to about 30 nucleotide bases or more in length.

E9.1. The method of any one of embodiments E1 to E8, wherein the homopolynucleotide is about 10 nucleotide base to about 35 nucleotide bases or more in length.

E10. The method of any one of embodiments E1 to E9, comprising terminating the terminal transferase activity after the heteropolynucleotide and/or the homopolynucleotide is added to the candidate nucleic acid molecule.

E11. The method of embodiment E10, comprising exposing the terminal transferase activity to heat and/or a chemical denaturant in an amount sufficient to terminate the terminal transferase activity.

E12. The method of any one of embodiments E1 to E11, comprising removing the nucleotides in the mixture or composition, or inactivating the nucleotides in the mixture or composition from the nucleic acid.

E13. The method of embodiment E12, comprising binding the nucleic acid comprising the heteropolynucleotide to a solid phase and separating the nucleic acid from the nucleotides.

E14. The method of embodiment E7 or E13, wherein the single nucleotide monomers consist of one nucleotide triphosphate species.

E15. The method of embodiment E14, wherein the one nucleotide triphosphate species is chosen from adenosine triphosphate (ATP), guanosine triphosphate (GTP), cytidine triphosphate (CTP) and thymidine triphosphate (TTP).

E16. The method of any one of embodiments E1 to E15, comprising amplifying the nucleic acid comprising the heteropolynucleotide.

E17. The method of embodiment E16, wherein the nucleic acid comprises a homopolynucleotide, and the amplifying comprises annealing a second single-stranded nucleic acid comprising a binding polynucleotide complementary to, or substantially complementary to, the homopolynucleotide, or portion thereof, in the nucleic acid.

E18. A method for modifying a nucleic acid, comprising:
(a) contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid;
(b) contacting the first modified nucleic acid with a terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid comprising, 5' to 3', the heteropolynucleotide and the homopolynucleotide; and
(c) contacting the second modified nucleic acid with a second single-stranded nucleic acid comprising a binding polynucleotide complementary to, or substantially complementary to, the homopolynucleotide of the second modified nucleic acid under extension conditions, and optionally under amplification conditions.

E18.1. The method of embodiment E17 and E18, wherein the second single-stranded nucleic acid comprises a first priming tag polynucleotide.

E18.2. The method of any one of embodiments E16 to E18.1, with the proviso that the method does not include contacting nucleic acid with a ligase activity.

E19. The method of any one of embodiments E1 to E18.2, comprising contacting the nucleic acid comprising the heteropolynucleotide with a second single-stranded nucleic acid and a ligase activity under conditions in which the nucleic acid comprising the heteropolynucleotide and the second single-stranded nucleic acid ligate, thereby generating a ligated nucleic acid.

E20. The method of embodiment E19, wherein the second single-stranded nucleic acid comprises a binding polynucleotide complementary to, or substantially complementary to, a polynucleotide in the nucleic acid prior to the nucleic acid being modified by the heteropolynucleotide and/or the homopolynucleotide.

E21. The method of embodiment E20, wherein the second single-stranded nucleic acid comprises a binding polynucleotide complementary to, or substantially complementary to, the candidate polynucleotide or portion thereof.

E22. The method of embodiment E19, wherein the nucleic acid comprises a homopolynucleotide and the second single-stranded nucleic acid comprises a binding polynucleotide complementary to, or substantially complementary to, the homopolynucleotide, or portion thereof, in the nucleic acid.

E22.1. A method for modifying a nucleic acid, comprising:
- (a) contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid;
- (b) contacting the first modified nucleic acid with a terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid comprising, 5' to 3', the heteropolynucleotide and the homopolynucleotide; and
- (c) contacting the second modified nucleic acid with a second single-stranded nucleic acid comprising a binding polynucleotide complementary to, or substantially complementary to, the homopolynucleotide in the second modified nucleic acid and a ligase activity under conditions in which the 3' end of the second modified nucleic acid and the 5' end of the second single-stranded nucleic acid ligate, thereby generating a ligated nucleic acid.

E22.2. A method for modifying a nucleic acid, comprising:
- (a) contacting a nucleic acid with a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid;
- (b) contacting the first modified nucleic acid with a terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid comprising, 5' to 3', the heteropolynucleotide and the homopolynucleotide; and
- (c) contacting the second modified nucleic acid with nucleotides, a polymerase and a second single-stranded nucleic acid comprising a binding polynucleotide complementary to, or substantially complementary to, the homopolynucleotide in the second modified nucleic acid under linear amplification conditions, thereby generating first amplicons; and
- (d) contacting the first amplicons with a ligase activity under conditions in which the 3' end and 5' end of the first amplicons are ligated and circularized first amplicons are generated.

E22.3. The method of any one of embodiments E19 to E22.2, wherein the homopolynucleotide is a tandem homopolynucleotide.

E22.4. The method of any one of embodiments E19 to E22.3, wherein the second single-stranded nucleic acid comprises a first priming tag polynucleotide.

E22.5. The method of embodiment E22.4, comprising amplifying the ligated nucleic acid.

E23. The method of any one of embodiments E19 to E22.5, wherein the second single-stranded nucleic acid comprises a cleavable nucleotide.

E24. The method of embodiment E23, wherein the cleavable nucleotide is deoxyinosine.

E25. The method of embodiment E23 or E24, comprising contacting the ligated nucleic acid or circularized first amplicons with a cleaving agent that cleaves the ligated nucleic acid or circularized first amplicons at the cleavable nucleotide, thereby generating linearized nucleic acid.

E26. The method of embodiment E25, wherein the cleaving agent is Endonuclease V.

E27. The method of embodiment E25 or E26, comprising contacting the linearized nucleic acid with a ligase activity under conditions that circularize the linearized nucleic acid, thereby generating a circularized nucleic acid.

E28. The method of embodiment E27, comprising amplifying the circularized nucleic acid or portion thereof.

E29. The method of embodiment E28, wherein the second single-stranded nucleic acid comprises a first priming tag polynucleotide.

E30. The method of embodiment E29, wherein the second single-stranded nucleic acid comprises a first priming tag polynucleotide and a second priming tag polynucleotide different than the first priming tag polynucleotide.

E31. The method of embodiment E30, comprising generating linearized nucleic acid from the ligated nucleic acid or circularized first amplicons.

E31.1. The method of embodiment E31, wherein the second single-stranded nucleic acid comprises a synthetic spacer between the first priming tag polynucleotide and the second priming tag polynucleotide.

E31.2. The method of embodiment E31.1, comprising contacting the ligated nucleic acid or circularized first amplicons with nucleotides and a polymerase under conditions in which the polymerase does not read through the synthetic spacer, thereby generating the linearized nucleic acid.

E31.3. The method of embodiment E31, wherein the second single-stranded nucleic acid comprises a cleavable nucleotide between the first priming tag polynucleotide and the second priming tag polynucleotide.

E31.4. The method of embodiment E31.3, comprising contacting the ligated nucleic acid or circularized first amplicons with an agent that cleaves the cleavable nucleotide, thereby generating the linearized nucleic acid.

E32. the method of any one of embodiments E25 to E31.4, comprising contacting the linearized nucleic acid with nucleotides, a polymerase and amplification primers under amplification conditions, thereby generating amplified linearized nucleic acid.

E33. A method for analyzing nucleic acid, comprising:
- (a) contacting a nucleic acid with terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid (i.e., an indexed nucleic acid);

(b) inactivating the terminal transferase activity and the nucleotides in the mixture after (a) after a first predetermined period of time;

(c) contacting the first modified nucleic acid with terminal transferase activity and a composition comprising single nucleotide monomers under conditions in which the monomers are added to the 3' terminus of the first modified nucleic acid by the terminal transferase activity, thereby adding a homopolynucleotide comprising the monomers to the 3' end of the first modified nucleic acid and generating a second modified nucleic acid;

(d) inactivating the terminal transferase activity after (c) after a second predetermined period of time;

(e) contacting the second modified nucleic acid with a first primer oligonucleotide that can anneal to the homopolynucleotide and comprises at its 5' end a first sequence, a mixture of nucleotides and a polymerase under linear amplification conditions, thereby amplifying the second modified nucleic acid and generating first amplicons;

(f) contacting the first amplicons with a second primer oligonucleotide comprising a second sequence that anneals in a sequence-specific manner to the first amplicons, a third primer oligonucleotide comprising on its 3' end the first sequence, a mixture of nucleotides and a polymerase under exponential amplification conditions, thereby generating second amplicons;

(g) inactivating or removing the nucleotides that are unused and primer oligonucleotides that are unused after (f); and (h) determining sequences of the second amplicons.

E34. The method of embodiment E33, wherein second amplicons from different reactions are pooled after (g) and prior to (h).

E35. The method of embodiment E33 or E34, wherein (a) through (g) are performed in a single container.

E36. The method of any one of embodiments E33 to E35, wherein the second primer oligonucleotide can anneal to a polynucleotide locus present in a subset of the first amplicons.

E37. The method of any one of embodiments E33 to E36, wherein the third primer oligonucleotide can anneal to complements of the first amplicons.

E38. The method of embodiment E36, wherein the polynucleotide locus is part of, or adjacent to, a region of interest.

E39. The method of any one of embodiments E33 to E38, wherein the second primer oligonucleotide and/or the third primer oligonucleotide includes one or more polynucleotides that facilitate a sequencing process that determines the sequences of the second amplicons in (h).

E40. The method of any one of embodiments E33 to E39, wherein the sequences of the second amplicons are determined in (h) by a highly multiplexed sequencing (HMS) process or NGS process.

E41. The method of any one of embodiments E1 to E40, wherein the nucleic acid comprises a plurality of nucleic acid molecules, there are about $4^5$ to about $4^{30}$ or more different heteropolynucleotides, and there is one of the heteropolynucleotides added to each of the plurality of nucleic acid molecules.

F1. A composition comprising a terminal transferase enzyme and a mixture comprising one or two or more different nucleotides.

F2. The composition of embodiment F1, comprising a salt and/or buffer.

F3. The composition of embodiment F1 or F2, comprising a terminal transferase enzyme co-factor.

F4. The composition of embodiment F3, wherein the co-factor is chosen from cobalt, manganese or magnesium.

F5. The composition of any one of embodiments F1 to F4, wherein the mixture comprises three or more different nucleotides.

F6. The composition of any one of embodiments F1 to F5, wherein the mixture comprises four different nucleotides.

F7. The composition of any one of embodiments F1 to F6, wherein the different nucleotides in the mixture are different deoxynucleotide triphosphates.

F8. The composition of embodiment F7, wherein the different nucleotides in the mixture are chosen from adenosine triphosphate (ATP), guanosine triphosphate (GTP), cytidine triphosphate (CTP) and thymidine triphosphate (TTP).

F9. The composition of any one of embodiments F1 to F8, comprising a nucleic acid having a 3' end to which the terminal transferase enzyme can add one or more nucleotides from the mixture of different nucleotides, thereby generating a modified nucleic acid comprising a heteropolynucleotide comprising two or more nucleotides from the mixture of different nucleotides.

F9.1. The composition of embodiment F9, wherein the nucleic acid comprises a candidate polynucleotide located 5' of the heteropolynucleotide.

F10. The composition of embodiment F9, wherein the nucleic acid is double-stranded or partially single-stranded and partially double-stranded.

F11. The composition of embodiment F9, wherein the nucleic acid is single-stranded.

F12. The composition of any one of embodiments F9 to F11, wherein there are about $4^5$ to about $4^{30}$ or more different heteropolynucleotides.

F13. The composition of any one of embodiments F1 to F12, comprising a composition comprising single nucleotide monomers.

F14. The composition of embodiment F13, wherein the single nucleotide monomers are nucleotide triphosphates.

F15. The composition of embodiment F14, wherein the single nucleotide monomers are chosen from adenosine triphosphate (ATP), guanosine triphosphate (GTP), cytidine triphosphate (CTP) and thymidine triphosphate (TTP).

H1. A kit comprising a terminal transferase enzyme and a mixture comprising two or more different nucleotides.

H2. The kit of embodiment H1, comprising a salt and/or buffer.

H3. The kit of embodiment H1 or H2, comprising a terminal transferase enzyme co-factor.

H4. The kit of embodiment H3, wherein the co-factor is chosen from cobalt, manganese or magnesium.

H5. The kit of any one of embodiments H1 to H4, wherein the mixture comprises two or more different nucleotides.

H6. The kit of any one of embodiments H1 to H5, wherein the mixture comprises three different nucleotides or four different nucleotides.

H7. The kit of any one of embodiments H1 to H6, wherein the different nucleotides in the mixture are different deoxynucleotide triphosphates.

H8. The kit of embodiment H7, wherein the different nucleotides in the mixture are chosen from adenosine triphosphate (ATP), guanosine triphosphate (GTP), cytidine triphosphate (CTP) and thymidine triphosphate (TTP).

H9. The kit of any one of embodiments H1 to H8, comprising a composition comprising single nucleotide monomers.

H9.1. The kit of embodiment H9, wherein the single monomers are nucleotide triphosphates.

H10. The kit of embodiment H9 or H9.1, wherein the single nucleotide monomers are chosen from adenosine triphosphate (ATP), guanosine triphosphate (GTP), cytidine triphosphate (CTP) and thymidine triphosphate (TTP).

H11. The kit of any one of embodiments H1 to H10, comprising instructions for appending two or more different nucleotides from the mixture to a 3' end of a nucleic acid to generate a modified nucleic acid comprising a heteropolynucleotide that comprises two or more nucleotides from the mixture.

H11.1. The kit of any one of embodiments H1 to H11, comprising instructions for appending two or more single nucleotide monomers from the composition to a 3' end of a nucleic acid to generate a modified nucleic acid that comprises a homopolynucleotide comprising two or more nucleotides from the composition.

H12. The kit of embodiment H11, wherein the instructions describe a method of any one of embodiments E1 to E40.

H13. The kit of embodiment H11 or H12, wherein the nucleic acid is double-stranded or partially single-stranded and partially double-stranded.

H14. The kit of embodiment H11 or H12, wherein the nucleic acid is single-stranded.

H15. The kit of any one of embodiments H11 to H14, wherein the nucleic acid comprises a candidate polynucleotide located 5' of the heteropolynucleotide and/or the homopolynucleotide.

H16. The kit of any one of embodiments H11 to H15, wherein about $4^5$ to about $4^{30}$ different heteropolynucleotides are generated.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow.

What is claimed is:

1. A method for producing an indexed single-stranded nucleic acid molecule, comprising:
    (a) contacting a first single-stranded nucleic acid (ssNA) molecule comprising a 5'-end that is optionally dephosphorylated, a target sequence, and a 3'-end, with (1) a polypeptide having a terminal transferase activity, and (2) dNTPs and/or NTPs comprising two or more different nucleotides species, under reaction conditions wherein a random sequence of the two or more different nucleotides species nucleotide residues is added to the 3' end of the first ssNA molecule so as to create a unique molecular index having two or more different nucleotides species;
    (b) contacting the first ssNA molecule with a second ssNA molecule comprising a 5'-phosphate moiety that is optionally adenylated, a 5' leader sequence, a target binding sequence that is complementary to at least a portion of the target sequence, and optionally the second ssNA molecule comprises a 3' tail, and optionally the second ssNA molecule has a blocked 3'-end,
    (c) hybridizing or annealing the first and second ssNA molecules under conditions wherein at least a portion of the target sequence and target binding sequence hybridize or anneal to each other by base pair complementarity; and
    (d) contacting the hybridized or annealed molecules with a single-stranded nucleic acid ligase activity to ligate the 3'-end of the first ssNA molecule with the 5'phosphate moiety of the second ssNA molecule to produce a ligated, indexed single ssNA molecule.

2. The method of claim 1, wherein the target sequence comprises 18-27 or 28-35 nucleotides.

3. The method of claim 1, wherein the first ssNA molecule comprises a 3'-tail sequence.

4. The method of claim 1, wherein the first ssNA molecule further comprises a 3'-end extended with one or more T residues.

5. The method of claim 1, wherein the first ssNA molecule further comprises a 5' target leader sequence.

6. The method of claim 1, wherein the first ssNA molecule further comprises a residue or sequence of interest 3' from the target sequence or 5' from the target sequence.

7. The method of claim 1, wherein the second ssNA molecule further comprises a G residue at its 5'-end.

8. The method of claim 1, wherein the target sequence and the target binding sequence, when hybridized or annealed, has a melting temperature of about 60° C.

9. The method of claim 1, wherein the 5' leader sequence of the second ssNA molecule comprises a molecular index sequence.

10. The method of claim 9, wherein the method comprises a plurality of first ssNA molecules and each second ssNA molecule comprises a different molecular index sequence.

11. The method of claim 9, wherein the 5' leader sequence of the second ssNA molecule comprises a molecular index sequence and a primer binding sequence.

12. The method of claim 1, further comprising contacting the unligated first and second ssNA molecules, and the ligated, indexed molecules, with a polypeptide having a single-stranded exonuclease activity to digest single-stranded molecules, and then optionally inactivating said polypeptide having a single-stranded exonuclease activity, optionally by heat inactivating said polypeptide having a single-stranded exonuclease activity.

13. The method of claim 1, wherein the target binding sequence of the second ssNA molecule comprises one or more nucleotides selected from the group consisting of uracil, inosine, abasic and a modified nucleotide.

14. The method of claim 13, further comprising
(a) contacting the molecules with a single-stranded exonuclease activity to digest single-stranded molecules, optionally inactivating said exonuclease activity, optionally heat inactivating said exonuclease activity,
(b) contacting the remaining molecules with an enzyme having an activity that removes the one or more nucleotides selected from the group consisting of uracil, inosine, abasic and a modified nucleotide, and removing the one or more nucleotides,
(c) hybridizing or annealing the resultant molecules with a primer oligonucleotide that is complementary to the primer binding sequence,
wherein optionally the primer comprises a 5' extension, and
(d) contacting the resultant molecules with a polymerase activity to amplify the resultant molecules.

15. The method of claim 1, wherein the first ssNA molecule is prepared from a biological specimen.

16. A method for producing a single-stranded nucleic acid molecule, the method comprising contacting a first single-stranded nucleic acid (ssNA) molecule comprising a phosphorylated 5'-end, a target sequence, and a 3'-end, with (1) a polypeptide having a terminal transferase activity, and (2) dNTPs, NTPs or a mix of dNTPs and NTPs, under reaction conditions wherein a random sequence of nucleotide residues is added to the 3' end of the first ssNA molecule to generate a first 3' tail sequence, thus producing an indexed nucleic acid;
contacting the first ssNA molecule with a single-stranded nucleic acid ligase activity to ligate the 3'-end of the first ssNA molecule with it's 5' phosphate moiety to produce a single closed circular ssNA molecule, and
amplifying a portion of the single closed circular ssNA molecule in such a way that the molecular index and portions of interest of the native molecule are copied.

17. A method for modifying a nucleic acid, comprising:
(a) contacting a nucleic acid with a polypeptide having a terminal transferase activity and a mixture of two or more different nucleotides under conditions in which nucleotides in the mixture are sequentially and randomly added to the 3' terminus of the nucleic acid by the terminal transferase activity, thereby adding a heteropolynucleotide comprising nucleotides in the mixture to the 3' end of the nucleic acid and generating a first modified nucleic acid;
(b) contacting the first modified nucleic acid with a polypeptide having a terminal transferase activity and a composition comprising a single species of nucleotide monomers under conditions in which the monomers are added to the 3' terminus of the first modified nucleic acid by the polypeptide having a terminal transferase activity, thereby adding a homopolynucleotide comprising the monomers to the 3' end of the first modified nucleic acid and generating a second modified nucleic acid comprising, 5' to 3', the heteropolynucleotide and the homopolynucleotide; and
(c) contacting the second modified nucleic acid with a second single-stranded nucleic acid comprising a binding polynucleotide complementary to, or substantially complementary to, the homopolynucleotide in the second modified nucleic acid and a ligase activity under conditions in which the 3' end of the second modified nucleic acid and the 5' end of the second single-stranded nucleic acid ligate, thereby generating a ligated nucleic acid.

18. The method of claim 1, wherein the 5' phosphate moiety of the second ssNA molecule is adenylated.

19. The method of claim 1, wherein the method further comprises:
(1) heat inactivating the polypeptide having a terminal transferase activity and/or removing or inactivating the dNTPs and/or NTPs before adding a 3'-tail sequence by use of a polypeptide having a terminal transferase activity, or
(2) heat inactivating the polypeptide having a terminal transferase activity and/or removing or inactivating the dNTPs and/or NTPs before optionally adding a 3'-tail sequence by use of a polypeptide having a terminal transferase activity.

20. The method of claim 14, wherein the activity that removes the one or more nucleotides is selected from the group consisting of a uracil-DNA glycosylase, an Endonuclease V, a APE 1, a Endonuclease III, a TMA Endonuclease III and an Endonuclease VIII.

21. The method of claim 14, wherein after removing the one or more nucleotides, inactivating said uracil-DNA glycosylase, Endonuclease V, APE 1, Endonuclease III, or Endonuclease VIII activity,
and optionally heat inactivating said uracil-DNA glycosylase, Endonuclease V, APE 1, Endonuclease III, or Endonuclease VIII activity.

22. The method of claim 16, further comprising adding a second 3'-tail sequence by use of a polypeptide having a terminal transferase activity and ribonucleotides.

23. The method of claim 16, wherein the 5'-end of the first ssNA molecule is adenylated.

* * * * *